US009247706B2

(12) United States Patent
Dewey et al.

(10) Patent No.: US 9,247,706 B2
(45) Date of Patent: Feb. 2, 2016

(54) COMPOSITIONS AND METHODS FOR MINIMIZING NORNICOTINE SYNTHESIS IN TOBACCO

(75) Inventors: Ralph E. Dewey, Apex, NC (US); Ramsey S. Lewis, Apex, NC (US)

(73) Assignee: North Carolina State University, Raleigh, NC (US)

( * ) Notice: Subject to any disclaimer, the term of this patent is extended or adjusted under 35 U.S.C. 154(b) by 681 days.

(21) Appl. No.: 13/521,766

(22) PCT Filed: Jan. 13, 2011

(86) PCT No.: PCT/US2011/021088
§ 371 (c)(1),
(2), (4) Date: Aug. 13, 2012

(87) PCT Pub. No.: WO2011/088180
PCT Pub. Date: Jul. 21, 2011

(65) Prior Publication Data
US 2013/0037040 A1 Feb. 14, 2013

Related U.S. Application Data

(60) Provisional application No. 61/295,671, filed on Jan. 15, 2010.

(51) Int. Cl.
*A01H 5/12* (2006.01)
*A24B 15/18* (2006.01)
(Continued)

(52) U.S. Cl.
CPC .............. *A01H 5/12* (2013.01); *C12N 9/0073* (2013.01); *C12N 15/8243* (2013.01)

(58) Field of Classification Search
CPC .......................... C12N 15/8243; C12N 15/8218
See application file for complete search history.

(56) References Cited

U.S. PATENT DOCUMENTS 4,693,976 A 9/1987 Schilperoort et al.
4,732,856 A 3/1988 Federoff
(Continued)

FOREIGN PATENT DOCUMENTS

EP 0 120 516 A3 10/1984
EP 0 267 159 A3 5/1988
(Continued)

OTHER PUBLICATIONS

Julio et al. (Reducing the content of nornicotine in tobacco via targeted mutation breeding, 21 Mol Breeding, 369-381 (2008)).*
(Continued)

*Primary Examiner* — Russell Kallis
*Assistant Examiner* — Weihua Weihua
(74) *Attorney, Agent, or Firm* — Alston & Bird LLP

(57) ABSTRACT

Compositions and methods for reducing the level of nornicotine and N'-nitrosonornicotine (NNN) in tobacco plants and plant parts thereof are provided. The compositions comprise isolated polynucleotides and polypeptides for a root-specific nicotine demethylases, CYP82E10, and variants thereof, that are involved in the metabolic conversion of nicotine to nornicotine in these plants. Compositions of the invention also include tobacco plants, or plant parts thereof, comprising a mutation in a gene encoding a CYP82E10 nicotine demethylase, wherein the mutation results in reduced expression or function of the CYP82E10 nicotine demethylase. Seed of these tobacco plants, or progeny thereof, and tobacco products prepared from the tobacco plants of the invention, or from plant parts or progeny thereof, are also provided. Methods for reducing the level of nornicotine, or reducing the rate of conversion of nicotine to nornicotine, in a tobacco plant, or plant part thereof are also provided. The methods comprise introducing into the genome of a tobacco plant a mutation within at least one allele of each of at least three nicotine demethylase genes, wherein the mutation reduces expression of the nicotine demethylase gene, and wherein a first of these nicotine demethylase genes encodes a root-specific nicotine demethylase involved in the metabolic conversion of nicotine to nornicotine in a tobacco plant or a plant part thereof. The methods find use in the production of tobacco products that have reduced levels of nornicotine and its carcinogenic metabolite, NNN, and thus reduced carcinogenic potential for individuals consuming these tobacco products or exposed to secondary smoke derived from these products.

19 Claims, 8 Drawing Sheets

(51) Int. Cl.
*C12N 9/02* (2006.01)
*C12N 15/82* (2006.01)

(56) References Cited

U.S. PATENT DOCUMENTS

| | | |
|---|---|---|
| 4,762,785 A | 8/1988 | Comai |
| 4,801,540 A | 1/1989 | Hiatt et al. |
| 4,940,838 A | 7/1990 | Schilperoort et al. |
| 4,945,050 A | 7/1990 | Sanford et al. |
| 5,004,863 A | 4/1991 | Umbeck |
| 5,013,658 A | 5/1991 | Dooner et al. |
| 5,034,323 A | 7/1991 | Jorgensen et al. |
| 5,104,310 A | 4/1992 | Saltin |
| 5,107,065 A | 4/1992 | Shewmaker et al. |
| 5,141,131 A | 8/1992 | Miller et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,302,523 A | 4/1994 | Coffee et al. |
| 5,352,605 A | 10/1994 | Fraley et al. |
| 5,378,619 A | 1/1995 | Rogers |
| 5,384,253 A | 1/1995 | Krzyzek et al. |
| 5,463,174 A | 10/1995 | Moloney et al. |
| 5,464,763 A | 11/1995 | Schilperoort et al. |
| 5,464,765 A | 11/1995 | Coffee et al. |
| 5,469,976 A | 11/1995 | Burchell |
| 5,472,869 A | 12/1995 | Krzyzek et al. |
| 5,583,021 A | 12/1996 | Dougherty et al. |
| 5,595,733 A | 1/1997 | Carswell et al. |
| 5,614,399 A | 3/1997 | Quail et al. |
| 5,641,664 A | 6/1997 | D'Halluin et al. |
| 5,668,295 A | 9/1997 | Wahab et al. |
| 5,679,558 A | 10/1997 | Göbel et al. |
| 5,684,241 A | 11/1997 | Nakatani et al. |
| 5,712,135 A | 1/1998 | D'Halluin et al. |
| 5,713,376 A | 2/1998 | Berger |
| 5,766,900 A | 6/1998 | Shillito et al. |
| 5,929,304 A | 7/1999 | Radin et al. |
| 6,002,070 A | 12/1999 | D'Halluin et al. |
| 6,074,877 A | 6/2000 | D'Halluin et al. |
| 6,907,887 B2 | 6/2005 | Conkling |
| 6,953,040 B2 | 10/2005 | Atchley et al. |
| 7,032,601 B2 | 4/2006 | Atchley et al. |
| 7,700,834 B2 | 4/2010 | Xu et al. |
| 7,700,851 B2 | 4/2010 | Xu |
| 7,812,227 B2 | 10/2010 | Xu |
| 7,855,318 B2 | 12/2010 | Xu |
| 7,884,263 B2 | 2/2011 | Dewey et al. |
| 8,058,504 B2 | 11/2011 | Xu |
| 8,124,851 B2 | 2/2012 | Dewey et al. |
| 8,319,011 B2 | 11/2012 | Xu et al. |
| 2002/0042934 A1 | 4/2002 | Staub et al. |
| 2004/0103449 A1 | 5/2004 | Xu |
| 2004/0111759 A1 | 6/2004 | Xu |
| 2004/0117869 A1 | 6/2004 | Xu |
| 2004/0162420 A1 | 8/2004 | Xu |
| 2005/0132444 A1 | 6/2005 | Xu |
| 2005/0160493 A9 | 7/2005 | Ratcliffe et al. |
| 2005/0178398 A1 | 8/2005 | Breslin et al. |
| 2005/0223442 A1 | 10/2005 | Xu |
| 2005/0244521 A1 | 11/2005 | Strickland et al. |
| 2006/0037096 A1 | 2/2006 | Xu |
| 2006/0037623 A1 | 2/2006 | Lawrence |
| 2006/0041949 A1 | 2/2006 | Xu |
| 2006/0157072 A1 | 7/2006 | Albino et al. |
| 2006/0185686 A1 | 8/2006 | Lawrence |
| 2006/0191548 A1 | 8/2006 | Strickland et al. |
| 2007/0149408 A1 | 6/2007 | Thomas et al. |
| 2007/0199097 A1 | 8/2007 | Xu et al. |
| 2007/0292871 A1 | 12/2007 | Xu |
| 2008/0076126 A1 | 3/2008 | Xu |
| 2008/0202541 A1* | 8/2008 | Dewey et al. ............ 131/347 |
| 2008/0245377 A1 | 10/2008 | Marshall et al. |
| 2009/0119788 A1 | 5/2009 | Mallmann et al. |
| 2009/0205072 A1 | 8/2009 | Dewey et al. |
| 2010/0012137 A1* | 1/2010 | Xu ........................ A01H 5/12 131/352 |
| 2010/0218270 A1 | 8/2010 | Xu et al. |
| 2010/0235938 A1* | 9/2010 | Xu ...................... C07K 14/415 800/260 |
| 2010/0235945 A1 | 9/2010 | Xu et al. |
| 2010/0235952 A1 | 9/2010 | Xu et al. |
| 2011/0048437 A1 | 3/2011 | Xu |
| 2011/0078817 A1 | 3/2011 | Xu |
| 2011/0174322 A1 | 7/2011 | Dewey et al. |
| 2011/0263328 A1 | 10/2011 | Yamashita et al. |
| 2012/0117933 A1 | 5/2012 | Dewey et al. |
| 2012/0118308 A1 | 5/2012 | Dewey et al. |

FOREIGN PATENT DOCUMENTS

| | | |
|---|---|---|
| EP | 0 292 435 B1 | 11/1988 |
| EP | 0 320 500 B1 | 6/1989 |
| EP | 0 116 718 | 5/1990 |
| EP | 0 159 418 B1 | 5/1990 |
| EP | O176 112 B1 | 5/1990 |
| EP | 0 131 624 BI | 9/1992 |
| EP | 0 627 752 B1 | 7/1997 |
| EP | 1 033 405 A3 | 9/2000 |
| EP | 0 290 799 B9 | 11/2003 |
| WO | WO 87/06614 A1 | 11/1987 |
| WO | WO 92/09696 A1 | 6/1992 |
| WO | WO 93/21335 A2 | 10/1993 |
| WO | WO 94/01930 A1 | 1/1994 |
| WO | WO 00/67558 A1 | 11/2000 |
| WO | WO 02/072758 A2 | 9/2002 |
| WO | WO 02/100199 A2 | 12/2002 |
| WO | WO 03/078577 A2 | 9/2003 |
| WO | WO 2004/035745 A2 | 4/2004 |
| WO | WO 2005/038018 A2 | 4/2005 |
| WO | WO 2005/038033 A2 | 4/2005 |
| WO | WO 2005/046363 A2 | 5/2005 |
| WO | WO 2005/111217 A2 | 11/2005 |
| WO | WO 2005/116199 A2 | 12/2005 |
| WO | WO 2006/022784 A1 | 3/2006 |
| WO | WO 2006/091194 A1 | 8/2006 |
| WO | WO 2006/120570 A2 | 11/2006 |
| WO | WO 2008/070274 A2 | 6/2008 |
| WO | WO 2008/076802 A2 | 6/2008 |
| WO | WO 2009/064771 A2 | 5/2009 |
| WO | WO 2011/088180 A1 | 7/2011 |
| WO | WO 2012/118779 A1 | 9/2012 |

OTHER PUBLICATIONS

Chakrabarti, M., et al. "Inactivation of the cytochrome P450 gene CYP82E2 by degenerative mutations was a key event in the evolution of the alkaloid profile of modern tobacco." New Phytologist 175.3 (2007): 565-574.*

Lewis, R.S., et al. "Three nicotine demethylase genes mediate nornicotine biosynthesis in Nicotiana tabacum L.: functional characterization of the CYP82E10 gene." Phytochemistry 71.17 (2010): 1988-1998.*

Sisson, Verne A., and R. F. Severson. "Alkaloid composition of the Nicotiana species." Beiträge zur Tabakforschung/Contributions to Tobacco Research 14.6 (1990): 327-339.*

Jack, A., et al., "Relative Stability of Nicotine to Nornicotine Conversion in Three Burley Cultivars," 18 pages, 36 slides (basis for JACK, A., et al., published in CORESTCongress Abstract AP2, Kyoto (2004) Agro Phyto Groups; 32 pages (unpaginated, abstract appearing on p. 11)).

Mann, T. J., et al., "Inheritance of the Conversion of Nicotine to Nornicotine in Varieties of Nicotiana tabacum L. and Related Amphiploids," Crop Science, 1964, pp. 349-353, vol. 4.

U.S. Appl. No. 60/337,684, Xu.
U.S. Appl. No. 60/347,444, Xu.
U.S. Appl. No. 60/363,684, Xu.
U.S. Appl. No. 60/418,933, Xu.
U.S. Appl. No. 60/485,368, Xu.
U.S. Appl. No. 60/503,989, Xu.

(56) References Cited

OTHER PUBLICATIONS

U.S. Appl. No. 60/566,235, Xu.
U.S. Appl. No. 60/607,357, Xu.
U.S. Appl. No. 60/646,764, Xu.
U.S. Appl. No. 60/665,097, Xu.
U.S. Appl. No. 60/665,451, Xu.
Adams et al., "Genes duplicated by polyploidy show unequal contributions to the transcriptome and organ-specific reciprocal silencing," *PNAS*, 100(8):4649-4654 (2003).
Allen et al., "RNAi-mediated replacement of morphine with the nonnarcotic alkaloid reticulin in opium poppy," *Nature Biotechnology*, 22(12):1559-1566 (2004).
Alonso et al., "*A Hox* gene mutation that triggers nonsense-mediated RNA decay and affects alternative splicing during *Drosophila* development," *Nucleic Acids Research*, 31(14):3873-3880 (2003).
Arciga-Reyes et al., "UPF1 is required for nonsense-mediated mRNA decay (NMD) and RNAi in *Arabidopsis*" *The Plant Journal*, 47:480-489 (2006).
Arndt et al., "Colocalization of antisense RNAs and ribozymes with their target mRNAs," *Genome*, 40:785-797 (1997).
ARS-GRIN: PI 551280, "*Nicotiana tabacum*," http://www.ars-grin.gov/cgi-bin/npgs/acc/display.pl?1446216, accessed Feb. 2009).
Bak et al., Transgenic Tobacco and *Arabidopsis* Plants Expressing the Two Multifunctional Sorghum Cytochrome P450 Enzymes, CYP79A1 and CYP71E1, Are Cyanogenic and Accumulate Metabolites Derived from Intermediates in Dhurrin.
Bartoszewski et al., "Cloning of a Wound Inducible *Lycopersicon esculentum* Cytochrome P450 Gene and Lack of Regeneration of Transgenic Plants with Sense or Antisense Constructs," *J. Am. Soc. Hort. Sci.*, 127(4):535-539 (2002).
Baseggio et al., "Size and genomic location of the pMGA multigene family of *Mycoplasma gallisepticum*," *Microbiology*, 142:1429-1435 (1996).
Batard et al., "Increasing Expression of P450 and P450-Reductase Proteins from Monocots in Heterologous Systems," *Arch. Biochem. Biophys.*, 379:161-169 (2000).
Baulcombe, "Fast Forward Genetics Based on Virus-Induced Gene Silencing," *Current Opinion in Plant Biology*, 2:109-113 (1999).
Bolitho et al., "Antisense apple ACC-oxidase RNA reduces ethylene production in transgenic tomato fruit," *Plant Science*, 122:91-99 (1997).
Bosher et al., "RNA interference: genetic wand and genetic watchdog," *Nat. Cell Biol.*, 2:E31-E36 (2000).
Bosl et al., "The role of noise and positive feedback in the onset of autosomal dominant diseases," *BMC Systems Biology*, 4:1-15 (2010).
Boyette et al., "Results of year 2000 TSNA sampling program in flue-cured tobacco," *Recent Advances in Tobacco Science*, 27:17-22 (2001).
Branch, "A good antisense molecule is hard to find," *TIBS*, 23:45-50 (1998).
Brignetti et al., "Viral pathogenicity determinants are suppressors of transgene silencing in *Nicotiana benthamiana*," *EMBO J.*, 17(22):6739-6746 (1998).
Burns et al., "Large-scale analysis of gene expression, protein localization, and gene disruption in *Saccharomyces cerevisiae*," *Genes Dev.*, 8:1087-1105 (1994).
Burton et al., Changes in Chemical Composition of Burley Tobacco During Senescence and Curing. 2. Acylated Pyridine Alkaloids, American Chemical Society, pp. 579-583 (1988).
Burton et al., "Distribution of Tobacco Constituents in Tobacco Leaf Tissue. 1. Tobacco-Specific Nitrosamines, Nitrate, Nitrite, and Alkaloids," *J. Agric. Food Chem.*, 40:1050-1055.
Burton et al., "Changes in Chemical Composition of Burley Tobacco during Senescence and Curing. 2. Acylated Pyridine Alkaloids," *J. Agric. Food Chem.*, 38(3):579-584 (1998).
Bush et al., "Formation of tobacco-specific nitrosamines in air-cured tobacco," *Rec. Adv. Tob. Sci*, 27:23-46 (2001).
Byers et al., "Killing the messenger: new insights into nonsense-mediated mRNA decay" *The Journal of Clinical Investigation*, 109(1):3-6 (2002).

Byzova et al., "Transforming petals into sepaloid organs in *Arabidopsis* and oilseed rape: implementation of the hairpin RNA-mediated gene silencing technology in an organ-specific manner," *Planta*, 218:379-387 (2004).
Callis et al., "Introns increase gene expression in cultured maize cells," *Genes and Dev.*, 1:1183-1200 (1987).
Carron et al., "Genetic modification of condensed tannin biosynthesis in *Lotus corniculatus*. 1. Heterologous antisense dihydroflavonol reductase down-regulates tannin accumulation in "hairy root" cultures," *Theoretical and Applied Genetics*, 87(8): 1006.
Caruthers, "Chapter 1: New Methods for Chemically Synthesizing Deoxyoligonucleotides," Methods of DNA and RNA Sequencing, Weissman (ed.), Praeger Publishers, New York, pp. 1-22 (1983).
Chai et al., "Reducing the maize amylopectin content through RNA interference manipulation," *Zhi Wu Sheng Li Yu Fen Zi Sheng Wu Xue Xue Buo*, 31:625-630 (2005) (English Abstract only).
Chakrabarti et al., "CYP82E4-mediated nicotine to nornicotine conversion in tobacco is regulated by a senescence-specific signaling pathway," *Plant Mol. Biol.*, 66: 415-427 (2008).
Chang et al., "Predicting and Testing Physical Locations of Genetically Mapped Loci on Tomato Pachytene Chromosome," *Genetics*, 176:2131-2138 (2007).
Chao et al., "A silent mutation induces exon skipping in the phenylalanine hydroxylase gene in phenylketonuria," *Hum. Genet.*, 108:14-19 (2001).
Chappell, "Biochemistry and Molecular Biology of the Isoprenoid Biosynthetic Pathway in Plants," *Annu. Rev. Plant Physiol. Plant Mol. Biol.*, 46:521-547 (1995).
Chapple, "Molecular-Genetic Analysis of Plant Cytochrome P450-Dependent Monooxygenases," *Annu. Rev. Plant Physiol. Plant Mol. Biol.*, 49:311-343 (1998).
Chelvarajan et al., "Study of Nicotine Demethylation in *Nicotiana otophora*," *J. Agric. Food Chem.*, 41:858-862 (1993).
Chen et al., "Toxicological analysis of low-nicotine and nocotine-free cigarettes," Toxicology, 249: (2008).
Cheung et al., "A Floral Transmitting Tissue-Specific Glycoprotein Attracts Pollen Tubes and Stimulates Their Growth," *Cell*, 82:383-393 (1995).
Chintapakorn, et al., "Antisense-Mediated Down-Regulation of Putrescine N-Methyltransferase Activity in Transgenic *Nicotiana tabacum L*. can Lead to Elevated Levels of Anatabine at the Expense of Nicotine," *Plant Molecular Biology*, 53:87-105.
Cho et al., "Transcriptome Analysis and Physical Mapping of Barley Genes in Wheat-Barley Chromosome Addition Lines," *Genetics*, 172:1277-1285 (2006).
Chou et al., "Chromosome Rearrangements in *Arabidopsis thaliana* Generated Through Cre-lox Site Specific Recombination," Plant and Animal Genome VII Conference, Abstract No. P133.
Chuang et al., "Specific and heritable genetic interference by double-stranded RNA in *Arabidopsis thaliana*," *PNAS*, 97(9):4985-4990 (2000).
Cogoni et al., "Post-transcriptional gene silencing across kingdoms," *Curr. Opin. Genet. Dev.*, 10:638-643 (2000).
Colbert et al., "High-throughput screening for induced point mutations," *Plant Physiology*, 126:480-484 (2001).
Collier et al., "A Method for Specific Amplification and PCR Sequencing of Individual Members of Multigene Families: Application to the Study of Steroid 21-Hydroxylase Deficiency," *PCR Methods and Applications*, 1:181-186 (1992).
Colliver et al., "Differential modification of flavonoid and isoflavonoid biosynthesis with an antisense chalcone synthase construct in transgenic *Lotus corniculatus*," *Plant Mol. Biol.*, 35(4):509-522 (1997).
Crookshanks et al., "The potato tuber transcriptome: analysis of 6077 expressed sequence tags," *FEBS Lett.*, 506:123-126 (2001).
Davuluri et al., "Fruit-specific RNAi-mediated suppression of DET1 enhances carotenoid and favonoid content in tomatoes," *Nat. Biotechnol.*, 23:890-895 (2005).
Dekeyser et al., "Transient Gene Expression in Intact and Organized Rice Tissues," *Plant Cell*, 2:591-602 (1990).
Dewey et al., Meeting Abstract dated Sep. 27, 2005, 1 page.

(56) References Cited

OTHER PUBLICATIONS

Dewey et al., Power point presentation titled "Functional characterization of the nicotine N-Demethylase gene of tobacco," Philip Morris USA, 21 pages, 2006.
Donato et al., "Fluorescence-Based Assays in Intact Cells Expressing Individual Activities for Screening Nine Cytochrome P450 (P450) Human P450 Enzymes," *Drug Metab. Dispos.*, 32(7):699-706 (2004).
D'Souza et al., "Missense and silent tau gene mutations cause frontotemporal dementia with parkinsonism-chromosome 17 type, by affecting multiple alternative RNA splicing regulatory elements" *PNAS*, 96:5598-5603 (1999).
EBI Accession AV557806, dated Jun. 16, 2000, 2 pages.
Einset, "Differential expression of antisense in regenerated tobacco plants transformed with an antisense version of a tomato ACC oxidase gene," *Plant Cell Tissue and Organ Culture*, 46(2): 137-141 (1996).
Elkind et al., "Abnormal plant development and down-regulation of phenylpropanoid biosynthesis in transgenic tobacco containing a heterologous phenylalanine ammonia-lyase gene," *PNAS*, 87(22):9057-61 (1990).
EMBL Database Report for Accession No. EU182719, Dec. 2, 2007.
Escobar et al., "RNAi-mediated oncogene silencing confers resistance to crown gall tumorigenesis," *PNAS*, 98: 13437-13442 (2001).
European Search Report completed on Feb. 10, 2010, in European Application No. EP 07 86 5628, 4 pages.
European Search Report completed on Mar. 31, 2011, in European Application No. EP 10 01 5540, 8 pages.
Falcon-Perez et al., "Functional Domain Analysis of the Yeast ABC Transporter Ycf1p by Site-directed Mutagenesis," *J. Biol. Chem.*, 274(33):23584-23590 (1999).
Fang et al., "Multiple cis regulatory elements for maximal expression of the cauliflower mosaic virus 35S promoter in transgenic plants," *Plant Cell*, 1:141-150 (1989).
Fannin et al., "Nicotine demethylation in *Nicotiana*," *Med. Sci. Res.*, 20:807-808 (1992).
Faske et al., "Transgenic Tobacco Plants Expressing Pea Chloroplast Nmdh cDNA in Sense and Antisense Orientation," *Plant Physiol*, 115(2): 705-715 (1997).
Fedoroff et al., "Cloning of the bronze locus in maize by a simple and generalizable procedure using the transposable controlling element Activator (AC)," *PNAS*, 81:3825-3829 (1984).
Fire et al., "Potent and specific genetic interference by double-stranded RNA in *Caenorhabditis elegans*," *Nature*, 391:806-811 (1998).
Force et al., "Preservation of Duplicate Genes by Complementary, Degenerative Mutations," *Genetics*, 151:1531-1545 (1999).
Forsthoefel et al., "T-DNA Insertion Mutagenesis in *Arabidopsis*: Prospects and Perspectives," *Aust. J. Plant Physiol.*, 19:353-366 (1992).
Frank et al., "Cloning of Wound-Induced Cytochrome P450 Monooxygenases Expressed in Pea," *Plant Physiol.*, 110:1035-1046 (1996).
Freeman et al., "Quantitative RT-PCR: Pitfalls and Potential," *BioTechniques*, 26:112-125 (1999).
Fromm et al., "An octopine synthase enhancer element directs tissue-specific expression and binds ASF-1, a factor from tobacco nuclear extracts," *Plant Cell*, 1:977-984 (1989).
Gavilano, "Isolation, Cloning and Characterization of Novel Tobacco Cytochrome P450 Genes Involved in Secondary Metabolism," Plant Biology Meeting, American Society of Plant Biologists, Abstract No. 992, 1 page (2004).
Gavilano et al. "Genetic Engineering of *Nicotiana tabacum* for Reduced Nornicotine Content" *J. Agric. Food Chem.*, 54:9071-9078 (2006).
Gavilano et al., "Isolation and Characterization of the Cytochrome P450 Gene CYP82E5v2 that Mediates Nicotine to Nornicotine Conversion in the Green Leaves of Tobacco," *Plant Cell Physiol.*, 48(11):1567-1574 (2007).
GenBank Accession No. CAA64635, dated Sep. 12, 1996, 2 pages.
GenBank Accession No. BAA35080, dated Sep. 26, 2000, 2 pages.
GenBank Accession No. AAK62347, dated Jun. 14, 2001, 2 pages.
GenBank Accession No. AAK62343, dated Feb. 11, 2002, 2 pages.
GenBank Accession No. AAK62346, dated Feb. 11, 2002, 2 pages.
GenBank Accession No. AEK08729 dated Feb. 23, 2005, 2 pages.
GenBank Accession No. AAK62342, Sep. 20, 2005, 2 pages.
GenBank Accession No. ABA07804, dated Oct. 13, 2005, 2 pages.
GenBank Accession No. ABA07805, dated Oct. 13, 2005, 2 pages.
GenBank Accession No. ABA07807, dated Oct. 13, 2005, 2 pages.
GenBank Accession No. DQ131885, dated Oct. 13, 2005, 2 pages.
GenBank Accession No. DQ131886, dated Oct. 13, 2005, 2 pages.
GenBank Accession No. DQ131888, dated Oct. 13, 2005, 2 pages.
GenBank Accession No. DQ219341, dated Oct. 1, 2006, 2 pages.
GenBank Accession No. DQ219342, dated Oct. 1, 2006, 2 pages.
GenBank Accession No. DQ219343, dated Oct. 1, 2006, 2 pages.
GenBank Accession No. DQ219344, dated Oct. 1, 2006, 2 pages.
GenBank Accession No. DQ219345, dated Oct. 1, 2006, 2 pages.
GenBank Accession No. DQ219346, dated Oct. 1, 2006, 2 pages.
GenBank Accession No. DQ219347, dated Oct. 1, 2006, 2 pages.
GenBank Accession No. DQ219348, dated Oct. 1, 2006, 2 pages.
GenBank Accession No. DQ219349, dated Oct. 1, 2006, 2 pages.
GenBank Accession No. DQ219350, dated Oct. 1, 2006, 2 pages.
GenBank Accession No. DQ219351, dated Oct. 1, 2006, 2 pages.
GenBank Accession No. DQ219352, dated Oct. 1, 2006, 2 pages.
GenBank Accession No. DQ350312, dated Dec. 31, 2006, 2 pages.
GenBank Accession No. DQ350313, dated Dec. 31, 2006, 2 pages.
GenBank Accession No. DQ350314, dated Dec. 31, 2006, 2 pages.
GenBank Accession No. DQ350315, dated Dec. 31, 2006, 2 pages.
GenBank Accession No. DQ350316, dated Dec. 31, 2006, 2 pages.
GenBank Accession No. DQ350317, dated Dec. 31, 2006, 2 pages.
GenBank Accession No. DQ350318, dated Dec. 31, 2006, 2 pages.
GenBank Accession No. DQ350319, dated Dec. 31, 2006, 2 pages.
GenBank Accession No. DQ350320, dated Dec. 31, 2006, 2 pages.
GenBank Accession No. DQ350321, dated Dec. 31, 2006, 2 pages.
GenBank Accession No. DQ350322, dated Dec. 31, 2006, 2 pages.
GenBank Accession No. DQ350323, dated Dec. 31, 2006, 2 pages.
GenBank Accession No. DQ350324, dated Dec. 31, 2006, 2 pages.
GenBank Accession No. DQ350325, dated Dec. 31, 2006, 2 pages.
GenBank Accession No. DQ350326, dated Dec. 31, 2006, 2 pages.
GenBank Accession No. DQ350327, dated Dec. 31, 2006, 2 pages.
GenBank Accession No. DQ350328, dated Dec. 31, 2006, 2 pages.
GenBank Accession No. DQ350329, dated Dec. 31, 2006, 2 pages.
GenBank Accession No. DQ350330, dated Dec. 31, 2006, 2 pages.
GenBank Accession No. DQ350331, dated Dec. 31, 2006, 2 pages.
GenBank Accession No. DQ350332, dated Dec. 31, 2006, 2 pages.
GenBank Accession No. DQ350333, dated Dec. 31, 2006, 2 pages.
GenBank Accession No. DQ350334, dated Dec. 31, 2006, 2 pages.
GenBank Accession No. DQ350335, dated Dec. 31, 2006, 2 pages.
GenBank Accession No. DQ350336, dated Dec. 31, 2006, 2 pages.
GenBank Accession No. DQ350337, dated Dec. 31, 2006, 2 pages.
GenBank Accession No. DQ350338, dated Dec. 31, 2006, 2 pages.
GenBank Accession No. DQ350339, dated Dec. 31, 2006, 2 pages.
GenBank Accession No. DQ350340, dated Dec. 31, 2006, 2 pages.
GenBank Accession No. DQ350341, dated Dec. 31, 2006, 2 pages.
GenBank Accession No. DQ350342, dated Dec. 31, 2006, 2 pages.
GenBank Accession No. DQ350343, dated Dec. 31, 2006, 2 pages.
GenBank Accession No. DQ350344, dated Dec. 31, 2006, 2 pages.
GenBank Accession No. DQ350345, dated Dec. 31, 2006, 2 pages.
GenBank Accession No. DQ350346, dated Dec. 31, 2006, 2 pages.
GenBank Accession No. DQ350347, dated Dec. 31, 2006, 2 pages.
GenBank Accession No. DQ350348, dated Dec. 31, 2006, 2 pages.
GenBank Accession No. DQ350349, dated Dec. 31, 2006, 2 pages.
GenBank Accession No. DQ350350, dated Dec. 31, 2006, 2 pages.
GenBank Accession No. DQ350351, dated Dec. 31, 2006, 2 pages.
GenBank Accession No. DQ350352, dated Dec. 31, 2006, 2 pages.
GenBank Accession No. DQ350353, dated Dec. 31, 2006, 2 pages.
GenBank Accession No. DQ350354, dated Dec. 31, 2006, 2 pages.
GenBank Accession No. DQ350355, dated Dec. 31, 2006, 2 pages.
GenBank Accession No. DQ350356, dated Dec. 31, 2006, 2 pages.
GenBank Accession No. DQ350357, dated Dec. 31, 2006, 2 pages.
GenBank Accession No. DQ350358, dated Dec. 31, 2006, 2 pages.
GenBank Accession No. DQ350359, dated Dec. 31, 2006, 2 pages.
GenBank Accession No. DQ350360, dated Dec. 31, 2006, 2 pages.

(56) References Cited

OTHER PUBLICATIONS

GenBank Accession No. DQ350361, dated Dec. 31, 2006, 2 pages.
GenBank Accession No. DQ350362, dated Dec. 31, 2006, 2 pages.
GenBank Accession No. DQ350363, dated Dec. 31, 2006, 2 pages.
GenBank Accession No. DQ205656, dated Jan. 18, 2007, 2 pages.
GenBank Accession No. ABA07806, dated Mar. 7, 2007, 2 pages.
GenBank Accession No. DQ131887, dated Mar. 7, 2007, 2 pages.
Ghosh, "Polyamines and plant alkaloids," *Indian J. Exp. Biol.*, 38:1086-1091 (2000).
Goldrick et al., "Molecular Genetic Analysis of the User Group Associated with Two Mouse Light Chain Genetic Markers," *J. Exp. Med.*, 162:713-728 (1985).
Graham-Lorence et al., "P450s: Structural similarities and functional differences," *FASEB J.*, 10:206-214 (1996).
Guo et al., "Protein Tolerance to Random Amino Acid Change," *PNAS*, 101(25):9205-9210 (2004).
Hao et al., "Mechanism of Nicotine N-Demethylation in Tobacco Cell Suspension Cultures," *Phytochemistry*, 41(2):477-482 (1995).
Hao et al., "Nicotine N-Demethylase in Cell-Free Preparations from Tobacco Cell Cultures," *Phytochemistry*, 42(2):325-329 (1996).
Hao et al., "Evidence in Favour of an Oxidative N-Demethylation of Nicotine to Nornicotine in Tobacco Cell Cultures," *Journal Plant Physiology*, 152:420-426 (1998).
Haseloff et al., "Simple RNA enzymes with new and highly specific endoribonuclease activities," *Nature*, 334:585-591 (1998).
Hayes et al., "Blotting techniques for the study of DNA, RNA, and proteins," *BMJ*, 299(14):965-968 (1989).
Hecht et al., "The relevance of tobacco-specific nitrosamines to human cancer," *Cancer Surveys*, 8(2):273-294 (1989).
Hecht, "Biochemistry, Biology, and Carcinogenicity of Tobacco-Specific N-Nitrosamines," *Chemical Research in Toxicology*, 11(6):559-603 (1998).
Helene et al., "Control of Gene Expression by Triple Helix-Forming Oligonucleotides," *Ann. N.Y. Acad. Sci.*, 660:27-36 (1992).
Helene, "The anti-gene strategy: control of gene expression by triplex-forming-oligonucleotides," *Anti-Cancer Drug Des.*, 6:569-584 (1991).
Helliwell et al., "High-throughput vectors for efficient gene silencing in plants," *Funct. Plant Biol.*, 29:1217-1225 (2002).
Henikoff et al., "Single-Nucleotide Mutations for Plant Functional Genomics," *Annu. Rev. Plant Biol.*, 54:375-401 (2003).
Herbik et al., "Isolation, characterization and cDNA cloning of nicotianamine synthase from barley," *Eur J Biochem*, 265(1): 231-9 (1999).
Hibino et al., "Increase of Cinnamaldehyde Groups in Lignin of Transgenic Tobacco Plants Carrying an Antisense Gene for Cinnamyl Alcohol Dehydrogenase," *Biosci. Biotec. Biochem*, 59:929-931 (1995).
Hildering et al., "Chimeric Structure of the Tomato Plant After Seed Treatment with EMS and X-Rays," The Use of Induced Mutations in Plant Breeding, Pergamon Press, pp. 317-320 (1965).
Hill et al., "Functional analysis of conserved histidines in ADP-glucose pyrophosphorylase from *Escerichia coli*," *Biochem. Biophys. Res. Commun.*, 244:573-577 (1998) (Abstract only).
Hoekema et al., "A binary plant vector strategy based on separation of the vir- and T-region of the *Agrobacterium tumefaciens* Ti-plasmid," *Nature*, 303:179-180 (1983).
Hoffmann et al., "Tobacco-specific N-nitrosamines and *Areca*-derived N-nitrosamines: chemistry, biochemistry, carcinogenicity, and relevance to humans," *Journal of Toxicology and Environmental Health*, 41:1-52 (1994).
Huang et al., "Insights into Regulation and Function of the Major Stress-Induced hsp70 Molecular Chaperone In Vivo: Analysis of Mice with Targeted Gene Disruption of the *hsp70.1* or *hsp70.3* Gene," *Mol Cell Biol*, 21(24):8575-8591 (2001).
Ingelbrecht et al., "Posttranscriptional silencing of reporter transgenes in tobacco correlates with DNA methylation," *PNAS*, 91:10502-10506 (1994).
International Preliminary Report on Patentability in PCT/US07/087386 mailed 25 Jun. 2009, 6 pages.
International Search Report and the Written Opinion of the International Searching Authority, or the Declaration mailed on May 4, 2012, in International Application No. PCT/US2012/026864 (13 pages).
International Search Report and the Written Opinion of the International Searching Authority, or the Declaration mailed on Jul. 4, 2012, in International Application No. PCT/US2012/026795 (15 pages).
International Search Report mailed on Apr. 23, 2014, in International Patent Application No. PCT/US2014/011035.
Invitation to Pay Additional Fees issued on Jun. 23, 2014, in International Patent Application No. PCT/US2014/019381, 8 pages.
Isshiki et al., "Nonsense-mediated decay of mutant *waxy* mRNA in rice," *Plant Physiology*, 125:1388-1395 (2001).
Jack et al., "Relative stability of nicotine to nornicotine conversion in three burley cultivars," Coresta Congress, Kyoto, Agro-Phyto groups, Abstract AP2 (2004).
Johnston et al., "Dosage-sensitive function of retinoblastoma related and convergent.epigenetic control are required during the *Arabidopsis* life cycle," *PLoS Genet*, 6(6):e1000988 (2010).
Jorgensen et al., "Chalcone synthase cosuppression phenotypes in petunia flowers: comparison of sense vs. antisense constructs and single-copy vs. complex T-DNA sequences," *Plant Mol. Biol.*, 31:957-973 (1996).
Julio et al. "Reducing the content of nornicotine in tobacco via targeted mutation breeding," *Mol. Breeding*, 21:369-381 (2008).
Julio et al., "Targeted Mutation Breeding as a tool for tobacco crop improvement," presentation made in Oct. 2008.
Kafri et al., "The regulatory utilization of genetic redundancy through responsive backup circuits," *PNAS*, 103(31):11653-11658 (2006).
Kempin et al., "Targeted disruption in *Arabidopsis*," *Nature*, 389:802-803 (1997).
Keskin et al., "A new, structurally nonredundant, diverse data set of protein-protein interfaces and its implications," *Protein Science*, 13:1043-1055 (2004).
Kim et al., "*Arabidopsis* CYP85A2, a Cytochrome P450, Mediates the Baeyer-Villiger Oxidation of Castasterone to Brassinolide in Brassinosteroid Biosynthesis," *Plant Cell*, 17:2397-2412 (2005).
Klahre et al., "High molecular weight RNAs and small interfering RNAs induce systemic posttranscriptional gene silencing in plants," *PNAS*, 99:11981-11986 (2002).
Klink et al., "The Efficacy of RNAi in the Study of the Plant Cytoskeleton," *J. Plant Growth Regul.*, 19:371-384 (2000).
Koornneef, "Chapter 1: Classical mutagenesis in higher plants," *Molecular Plant Biology*, Gilmartin and Bowler, ed., Oxford University Press, pp. 1-11 (2002).
Koshinsky et al., "Cre-lox site-specific recombination between *Arabidopsis* and tobacco chromosomes," *Plant J.*, 23(6):715-722 (2000).
Kusaba et al., "*Low glutelin content1*: A Dominant Mutation That Suppresses the *Glutelin* Multigene Family via RNA Silencing in Rice," *Plant Cell*, 15:1455-1467 (2003).
Kynast et al., "Dissecting the maize genome by using chromosome addition and radiation hybrid lines," *PNAS*, 101(26):9921-9926 (2004).
Lazar et al., "Transforming Growth Factor a Mutation of Aspartic Acid 47 and Leucine 48 Results in Different Biological Activities," *Mol. Cell. Biol.*, 8(3):1247-1252 (1988).
Levin et al., "Methods of double-stranded RNA-mediated gene inactivation in *Arabidopsis* and their use to define an essential gene in methionine biosynthesis," *Plant Mol. Biol.*, 44:759-775 (2000).
Liu et al., "High-Stearic and High-Oleic Cottonseed Oils Produced by Hairpin RNA-Mediated Post-Transcriptional Gene Silencing," *Plant Physiol.*, 129:1732-1743 (2002).
Liu et al., "Identification and characterization of HTD2: a novel gene negatively regulating tiller bud outgrowth in rice," *Planta*, 230(4):649-658 (2009).
Liu et al "Genetic and transformation studies reveal negative regulation of ERS1 ethylene receptor signaling in *Arabidopsis*," *BMC Plant Biol*, 10:60-73 (2010).
Maher, "DNA Triple-Helix Formation: An Approach to Artificial Gene Repressors?" *BioEssays*, 14(12):807-815 (1992).

(56) References Cited

OTHER PUBLICATIONS

Maniatis et al., "Regulation of inducible and tissue-specific gene expression," *Science*, 236:1237-1245 (1987).

Mansoor et al. "Engineering novel traits in plants through RNA interference," *Trends in Plant Science*, 11(11):1-7 (2006).

Maquat, "Nonsense-mediated mRNA decay," *Curr. Biol.*, 12(6):R196-R197 (2002).

Matthew, "RNAi for plant functional genomics," *Comparative and Functional Genomics*, 5:240-244 (2004).

McDougall et al., "Detection of Viral DNA and RNA by In Situ Hybridization," *J. Histochem. Cytochem.*, 34:33-38 (1986).

McKinney et al., "Sequence-based identification of T-DNA insertion mutations in *Arabidopsis*: actin mutants *act2-1* and *act4-1*," *Plant J.*, 8(4):613-622 (1995).

Mesnard et al., "Evidence for the involvement of tetrahydrofolate in the demethylation of nicotine by *Nicotiana plumbaginifolia* cell-suspension cultures," *Planta*, 214:911-919 (2002).

Mette et al., "Transcriptional silencing and promoter methylation triggered by double-stranded RNA," *EMBO J.*, 19(19):5194-5201 (2000).

Mol et al., "Regulation of plant gene expression by antisense RNA," *FEBS Lett.*, 268(2):427-430 (1990).

Napoli et al., "Introduction of a Chimeric Chalcone Synthase Gene into Petunia Results in Reversible Co-Suppression of Homologous Genes in trans," *Plant Cell*, 2:279-289 (1990).

Nawrath et al., "Salicylic Acid Induction-Deficient Mutants of *Arabidopsis* Express *PR-2* and *PR-5* and Accumulate High Levels of Camalexin after Pathogen Inoculation," *Plant Cell*, 11:1393-1404 (1999).

Needleman et al., "A General Method Applicable to the Search for Similarities in the Amino Acid Sequence of Two Proteins," *J. Mol. Biol.*, 48:443-453 (1970).

Nelson et al., "Comparative Genomics of Rice and *Arabidopsis*. Analysis of 727 Cytochrome P450 Genes and Pseudogenes from a Monocot and a Dicot," *Plant Physiol.*, 135:756-772.

Nelson et al., "Comparison of cytochrome P450 (*CYP*) genes from the mouse and human genomes, including nomenclature recommendations for genes, pseudogenes and alternative-splice variants," *Pharmacogenetics*, 14:1-18 (2004).

Ng et al., "Specific Detection and Confirmation of *Campylobacter jejuni* by DNA Hybridization and PCR," *Appl. Environ. Microbiol.*, 63(11):4558-4563 (1997).

Nishihara et al., "Flavanoid components and flower color change in transgenic tobacco plants by suppression of chalcone isomerase gene," *FEBS Lett.*, 579:6074-6078 (2005).

Odell et al., "Identification of DNA sequences required for activity of the cauliflower mosaic virus 35S promoter," *Nature*, 313:810-812 (1985).

Office Action mailed on Oct. 18, 2006, in U.S. Appl. No. 10/293,252.
Office Action mailed on Oct. 30, 2006, in U.S. Appl. No. 10/686,947.
Office Action mailed on Nov. 14, 2006, in U.S. Appl. No. 10/387,346.
Office Action mailed on Nov. 14, 2006, in U.S. Appl. No. 10/340,861.
Office Action mailed on May 4, 2007, in U.S. Appl. No. 10/943,507.
Office Action mailed on Jun. 12, 2007, in U.S. Appl. No. 10/934,944.

Ogita et al., "Application of RNAi to confirm theobromine as the major intermediate for caffeine biosynthesis in coffee plants with potential for construction of decaffeinated varieties," *Plant Mol. Biol.*, 54:931-941 (2004).

Ohshima et al., "Nucleotide sequence of the *PR-1* gene of *Nicotiana tabacum*," *FEBS Letters*, 225:243-246 (1987).

Oliver et al, "Inhibition of tobacco NADH-hydroxypyruvate reductase by expression of a heterologous antisense RNA derived from a cucumber cDNA: Implications for the mechanism of action of antisense RNAs," *Mol Gen Genet*, 239(3):425-34 (1993).

Pearson et al., "Improved tools for biological sequence comparison," *PNAS*, 85:2444- 2448 (1988).

Peele et al., "Formation of Tobacco-specific Nitrosamines in Flue-cured Tobacco," CORESTA Meeting, Agro-Phyto Groups, Suzhou, China (1999).

Pickett et al., "Seeing Double: Appreciating Genetic Redundancy," *Plant Cell*, 7:1347-1356 (1995).

Plant Variety Protection Office (USDA-AMS, Beltsville, MD, http://www.ars-grin.gov/cgi-bin/npgs/htmllpvp.pl?Tobbaco, accessed Feb. 2009).

Puchta et al., "Two different but related mechanisms are used in plants for the repair of genomic double-strand breaks by homologous recombination," *PNAS*, 93:5055-5060 (1996).

Qin et al., "Cre recombinase-mediated site-specific recombination between plant chromosomes," *PNAS*, 91:1706-1710 (1994).

Qiu et al. "A computational study of off-target effects of RNA interference." *Nucleic Acids Research*, 33(6)1834-1847 (2005).

Ralston et al., "Cloning, Heterologous Aristolochene-1,3-Dihydroxylase from Expression, and Functional Characterization of 5-epi-Tobacco (*Nicotiana tabacum*)," *Arch. Biochem. Biophys.*, 393(2):222-235 (2001).

Reid et al., "Studies on the Fermentation of Tobacco 1. The Microflora of Cured and Fermenting Cigar-leaf Tobacco," Bulletin 356, Pennsylvania Agricultural Experiment Station, State College, PA, 18 pages (1938).

Rodermel et al., "Nuclear-Organelle Interactions: Nuclear Antisense Gene Inhibits Ribulose Biphosphate Carboxylase Enzyme Levels in Transformed Tobacco Plants," *Cell*, 55:673-681(1988).

Rohr et al., "Tandem inverted repeat system for selection of effective transgenic RNAi strains of *Chlamydomonas*," *Plant J.*, 40:611-621 (2004).

Ruiz et al., "Nicotine-free and salt-tolerant tobacco plants obtained by grafting to salinity-resistant rootstocks of tomato," *Physiologia Plantarum*, 24:(4):465-475 (2005).

Salehuzzaman et al., "Isolation and characterization of a cDNA encoding granule-bound starch synthase in cassava (*Manihot esculenta* Crantz) and its antisense expression in potato," *Plant Mol Biol*, 23(5):947-62 (1993).

Schenk et al., "Coordinated plant defense responses in *Arabidopsis* revealed by microarray analysis," *PNAS*, 97(21):11655-11660 (2000).

Schnable et al., "Genetic recombination in plants," *Curr. Opin. Plant Biol.*, 1:123-129 (1998).

Schopfer et al., "Identification of elicitor-induced cytochrome P450s of soybean (*Glycine max* L.) using differential display of mRNA," *Mol. Gen. Genet.*, 258:315-322 (1998).

Seal et al., "Isolation of a Pseudomonas solanacearum-Specific DNA Probe by Subtraction Hybridization and Construction of Species-Specific Oligonucleotide Primers for Sensitive Detection by the Polymerase Chain Reaction," *Appl. Environ. Microbiol*.

Sequence 6912f1 obtained from the Internet at http://mrg.pscsiken.go.ip/nicotiana/menu/069.html on Dec. 6, 2007, 1 page.

Shah et al., "Expression of Silent Mutations in Disease Phenotype," Abstract for presentation at 11th International Congress of Human Genetics, 1 page, (2006).

Shen et al., "Resistance Gene Candidates Identified by PCR with Degenerate Oligonucleotide Primers Map to Clusters of Resistance Genes in Lettuce," *Molecular Plant-Microbe Interactions*, 11(8):815-823 (1998).

Shew et al. (Eds.), "Compendium of Tobacco Diseases," published by American Phytopathology Society, 99 pages (1991).

Siminszky et al., "Conversion of nicotine to nornicotine in *Nicotiana tabacum* is mediated by CYP82E4, a cytochrome P450 monooxygenase," *PNAS*, 102(41):14919-14924 (2005).

Sinvany-Villalobo et al., "Expression in Multigene Families Analysis of Chloroplast and Mitochondrial Proteases," *Plant Physiol*, 135:1336-1345 (2004).

Skarnes, "Entrapment Vectors: A New Tool for Mammalian Genetics," *Bio/Technology*, 8:827-831 (1990).

Smith et al., "Comparison of Biosequences," *Adv. Appl. Math.*, 2:482-489 (1981).

Smith et al., "Total silencing by intron-spliced hairpin RNAs," *Nature*, 407:319-320 (2000).

Spradling et al., "Gene disruptions using P transposable elements: An integral component of the *Drosophila* genome project," *PNAS*, 92:10824-10830 (1995).

(56) References Cited

OTHER PUBLICATIONS

Stalberg et al., "Deletion analysis of a 2S seed storage protein promoter of *Brassica napus* in transgenic tobacco," *Plant Mol. Biol.*, 23:671-683 (1993).
Sundaresan et al., "Patterns of gene action in plant development revealed by enhancer trap and gene trap transposable elements," *Genes Dev.*, 9:1797-1810 (1995).
Sureka et al., "Positive Feedback and Noise Activate the Stringent Response Regulator Rel in Mycobacteria," *PLoS One*, 3(3):e1771 (2008).
Takeda et al., "Differentiation between Wild and Vaccine-Derived Strains of Poliovirus by Stringent Microplate Hybridization of PCR Products," *J. Clin. Microbiol.*, 32:202-204 (1994).
Takemoto et al., "Molecular Cloning of a Defense-Response-Related Cytochrome P450 Gene from Tobacco," *Plant Cell Physiol.*, 40(12):1232-1242 (1999).
Takken et al. "A functional cloning strategy, based on a binary PVX-expression vector, to isolate HR-inducing cDNAs of plant pathogens." *The Plant Journal*, 24(2): 275-283 (2000).
Tang et al., "Using RNAi to improve plant nutritional value: from mechanism to application," *TRENDS in Biotechnology*, 22(9):463-469 (2004).
Tavernarakis et al., "Heritable and inducible genetic interference by double-stranded RNA encoded by transgenes," *Nat. Genet.*, 24:180-183 (2000).
Temple et al., "Modulation of glutamine synthetase gene expression in tobacco by the introduction of an alfalfa glutamine synthetase gene in sense and antisense orientation: molecular and biochemical analysis," *Mol Gen Genet*, 236(2-3):315-25 (1993).
Thomas et al., "Size constraints for targeting post-transcriptional gene silencing and for RNA directed methylation in *Nicotiana benthamiana* using a potato virus X vector," *Plant J.*, 25(4):417-425 (2001).
Thornton et al., "From structure to function: Approaches and limitations," *Nature Structural Biology, Structural Genomics Supplement*, pp. 991-994 (2000).
Till et al., "Discovery of induced point mutations in maize genes by TILLING," *BMC Plant Biology*, 4:12 (2004).
Toscano et al., "A silent mutation (2939G>A, exon 6; CYP2D6*59) leading to impaired expression and function of CYP2D6," *Pharmacogenet. Genomics*, 16(10):767-770 (2006).
Travella, et al. "RNA Interference-Based Gene Silencing as an Efficient Tool for Functional Genomics in Hexaploid Bread Wheat." *Plant Physiology*, 142:6-20 (2006).
Trevanion et al., "NADP-Malate Dehydrogenase in the C4 Plant *Flaveria bidentis*," *Plant Physiol*, 113(4):1153-1165 (1997).
Turner et al., "Post-transcriptional gene-silencing and RNA interference: genetic immunity, mechanisms and applications," *J. Chem. Technol. Biotechnol.*, 75:869-882 (2000).
United States, "Tobacco in the United States," Miscellaneous Publication No. 867, U.S. Dept. of Agriculture, Agricultural Marketing Service, 27 pages (1979).
Vaistij et al., "Spreading of RNA Targeting and DNA Methylation in RNA Silencing Requires Transcription of the Target Gene and a Putative RNA-Dependent RNA Polymerase," *Plant Cell*, 14:857-867 (2002).
Van der Krol et al., "An anti-sense chalcone synthase gene in transgenic plants inhibits flower pigmentation," *Nature*, 333:866-869 (1988).
Van der Krol et al., "Antisense genes in plants: an overview," *Gene*, 72:45-50 (1988).
Vaucheret et al., "Post-transcriptional gene silencing in plants," *J. Cell Sci.*, 114:3083-3091 (2001).
Veena et al., "Glyoxalase I from *Brassica juncea*: molecular cloning, regulation and its overexpression confer tolerance in transgenic tobacco under stress," *Plant Journal*, 17(4):385-395 (1999).
Verdaguer et al., "Functional organization of the cassava vein mosaic virus (CsVMV) promoter," *Plant Mol. Biol.*, 37(6):1055-1067 (1998).
Verkerk, "Chimerism of the tomato plant after seed irradiation with fast neutrons," *Neth. J. Agric. Sci.*, 19:197-203 (1971).
Voss et al., "The role of enhancers in the regulation of cell-type-specific transcriptional control," *Trends Biochem. Sci.*, 11(7):287-289 (1986).
Wang et al., "Suppression of a P450 hydroxylase gene in plant trichome glands enhances natural product-based aphid resistance," *Nat. Biotechnol.*, 19:371-374 (2001).
Wang et al., "Isolation and characterization of the *CYP71D16* trichome-specific promoter from *Nicotania tabacum* L," *J. Exp. Botany*, 53(376):1891-1897 (2002).
Wang et al., "Elucidation of the functions of genes central to diterpene metabolism in tobacco trichomes using posttranscriptional gene silencing," *Planta*, 216:686-691 (2003).
Waterhouse et al., "Virus resistance and gene silencing in plants can be induced by simultaneous expression of sense and antisense RNA," *PNAS*, 95:13959-13964 (1998).
Weigel et al., "A developmental switch sufficient for flower initiation in diverse plants," *Nature*, 377:495-500 (1995).
Weising et al., "Foreign Genes in Plants: Transfer, Structure, Expression, and Applications," *Ann. Rev. Genetics*, 22:421-477 (1988).
Werck-Reichhart et al., "Cytochromes P450: a success story," *Genome Biology*, 1(6):reviews3003.1-3003.9 (2000).
Werck-Reichhart et al., "Cytochromes P450," The *Arabidopsis Book*, American Society of Plant Biologists, 28 pages (2002).
Wernsman et al., "Time and site of nicotine conversion in tobacco," *Tobacco Science*, 167(22):226-228 (1968).
Wernsman et al., "Relative Stability of Alleles at the Nicotine Conversion Locus of Tobacco," *Tobacco Science*, 14:34-36 (1970).
Wernsman et al., "Chapter Seventeen: Tobacco." *Cultivar Development. Crop Species*., W. H. Fehr (ed.), MacMillan Publishing Go., Inc., New York, N.Y., pp. 669-698 (1987).
Wesley et al., "Construct design for efficient, effective and high-throughput gene silencing in plants," *The Plant Journal*, 27(6): 581-590 (2001).
Wetmur, "DNA Probes: Applications of the Principles of Nucleic Acid Hybridization" *Critical Reviews in Bio. and Mol. Biol.*, 26:227-259, (1991).
Whitbred et al., "Molecular Characterization of *CYP73A9* and *CYP82A1* P450 Genes Involved in Plant Defense in Pea," *Plant Physiol.*, 124:47-58 (2000).
Written Opinion of the International Searching Authority mailed on Apr. 23, 2014, in International Patent Application No. PCT/US2014/011035.
Wu et al. "Herbivory Rapidly Activates MAPK Signaling in Attacked and Unattacked Leaf Regions but Not between Leaves of *Nicotiana attenuata*." *The Plant Cell*, 19:1096-1122 (2007).
Xiong et al., "Different effects on ACC oxidase gene silencing triggered by RNA interference in transgenic tomato," *Plant Cell*, 23:639-646 (2004).
Xu et al. "Computational Estimation and Experimental Verification of Off-Target Silencing during Posttranscriptional Gene Silencing in Plants," *Plant Physiology*, 142:429-440 (2006).
Xu et al., "Biochemical and molecular characterizations of nicotine demethylase in tobacco," *Physiologia Plantarum*, 129(2):307-319 (2007).
Zwart et al., "Rapid Screening for Freshwater Bacterial Groups by Using Reverse Line Blot Hybridization," *Appl. Environ. Microbiol.*, 69(10):5875-5883 (2003).
Chakrabarti, M., et al., "Inactivation of the cytochrome P450 gene *CYP82E2* by degenerative mutations was a key event in the evolution of the alkaloid profile of modern tobacco," *New Phytologist*, 2007, vol. 175, pp. 565-574.
Database EMBL, "CHO_OF040xc14fl.ab1 CHO_OF Nicotiana tabacum genomic 5', genomic survey sequence," Database accession No. ET701936, 2008, 1 page.
Database EMBL, "CHO_OF3490xi05rl.ab1 CHO_OF3 Nicotiana tabacum genomic 3', genomic survey sequence," Database accession No. FH058766, 2008, 1 page.
Database EMBL, "CHO_OF4790xg08f1.ab1 CHO_OF4 Nicotiana tabacum genomic 5', genomic survey sequence," Database accession No. FH555036, 2008, 1 page.

(56) References Cited

OTHER PUBLICATIONS

Database EMBL, "Nicotiana tabacum cDNA, clone: TBK02GR0013__1__H12, 5'-end sequence," Database accession No. FS405337, 2009, 1 page.

Database EMBL, "Nicotiana tabacum cultivar DH98-325-6 nicotine N-demethylase (CYP82E10) gene, complete cds," Database accession No. HM802352, 2010, pp. 1-2.

Gavilano, L, et al., "Functional Analysis of Nicotine Demethylase Genes Reveals Insights into the Evolution of Modern Tobacco," *The Journal of Biological Chemistry*, 2007, vol. 282(1), pp. 249-256.

Lewis, R., et al., "RNA interference (RNAi)-induced suppression of nicotine demethylase activity reduces levels of key carcinogen in cured tobacco leaves," *Plant Biotechnology Journal*, 2008, vol. 6, pp. 346-354.

Lewis, R., et al., "Three nicotine demethylase genes mediate nornicotine biosynthesis in *Nicotiana tabactan* L.: Functional characterization of the *CYP82E10* gene," *Phytochemistry*, 2010, vol. 71, pp. 1988-1998.

Nelson, "P450:CYP82," Metabolomics.JP, https://metabolomics.jp/mediawiki/index.php?title=P450:CYP82&printable1=yes, 2009, pp. 1-14.

* cited by examiner

FIGURE 1A

```
  1 ttttcaattttttgttacttttgtatttatcatattattatgcatagccctaaattatcta 61 taaaagggaagttggtgatagtttgattcccaagtgcttttctaaaaatccataATGGTT
                                                            M  V   2

121 TCTCCCGTAGAAGCCATCGTAGGACTAGTAACTCTTACACTTCTCTTCTACTTCATACGG
     S  P  V  E  A  I  V  G  L  V  T  L  T  L  L  F  Y  F  I  R  22

181 ACCAAAAAATCTCAAAAACCTTCAAAACCATTACCACCGAAAATCCCCGGAGGGTGGCCG
     T  K  K  S  Q  K  P  S  K  P  L  P  P  K  I  P  G  G  W  P  42

241 GTAATCGGCCATCTTTTCTATTTCGATGACGACAGCGACGACCGTCCATTAGCACGAAAA
     V  I  G  H  L  F  Y  F  D  D  D  S  D  D  R  P  L  A  R  K  62

301 CTCGGAGACTTAGCTGACAAATACGGCCCGGTTTTCACTTTTCGGCTAGGCCTTCCGCTT
     L  G  D  L  A  D  K  Y  G  P  V  F  T  F  R  L  G  L  P  L  82

361 GTGTTAGTTGTAAGCAGTTACGAAGCTATAAAAGACTGCTTCTCTACAAATGATGCCATT
     V  L  V  V  S  S  Y  E  A  I  K  D  C  F  S  T  N  D  A  I  102

421 TTCTCCAATCGTCCAGCTTTTCTTTATGGCGAATACCTTGGCTACAATAATGCCATGCTA
     F  S  N  R  P  A  F  L  Y  G  E  Y  L  G  Y  N  N  A  M  L  122

481 TTTTTGACAAAATACGGACCTTACTGGCGAAAAAATAGAAAATTAGTCATTCAGGAAGTT
     F  L  T  K  Y  G  P  Y  W  R  K  N  R  K  L  V  I  Q  E  V  142

541 CTCTGTGCTAGTCGTCTCGAAAAAATTGAAGCACGTGAGATTTGGTGAAATTCAGACGAGC
     L  C  A  S  R  L  E  K  L  K  H  V  R  F  G  E  I  Q  T  S  162

601 ATTAAGAATTTATACACTCGAATTGATGGAAATTCGAGTACGATAAATCTAACCGATTGG
     I  K  N  L  Y  T  R  I  D  G  N  S  S  T  I  N  L  T  D  W  182

661 TTAGAAGAATTGAATTTTGGTCTGATCGTGAAAATGATCGCTGGGAAAAATTATGAATCC
     L  E  E  L  N  F  G  L  I  V  K  M  I  A  G  K  N  Y  E  S  202

721 GGTAAAGGAGATGAACAAGTGGAGAGATTTAGGAAAGCGTTTAAGGATTTTATAATTTTA
     G  K  G  D  E  Q  V  E  R  F  R  K  A  F  K  D  F  I  I  L  222

781 TCAATGGAGTTTGTGTTATGGGATGCTTTTCCAATTCCATTGTTCAAATGGGTGGATTTT
     S  M  E  F  V  L  W  D  A  F  P  I  P  L  F  K  W  V  D  F  242

841 CAAGGCCATGTTAAGGCCATGAAAAGGACATTTAAGGATATAGATTCTGTTTTTCAGAAT
     Q  G  H  V  K  A  M  K  R  T  F  K  D  I  D  S  V  F  Q  N  262

901 TGGTTAGAGGAACATGTCAAGAAAAAAGAAAAAATGGAGGTTAATGCAGAAGGAAATGAA
     W  L  E  E  H  V  K  K  K  E  K  M  E  V  N  A  E  G  N  E  282

961 CAAGATTTCATTGATGTGGTGCTTTCAAAAATGAGTAATGAATATCTTGATGAAGGCTAC
     Q  D  F  I  D  V  V  L  S  K  M  S  N  E  Y  L  D  E  G  Y  302
```

FIGURE 1B

```
1021 TCTCGTGATACTGTCATAAAAGCAACAGTGTTTgtaagttcatctcattttcatttatt
      S   R   D   T   V   I   K   A   T   V   F                      313

1081 ctttgaggaatagacaggttaatagtaatttaagtaattagattatctaaatactaagga 1141 tgagtaaatatggcaaaaatatagaatgataaatggaaaaggatgataattttttatgcc 1201 cggactaatctaactttgggagttaaagcacttcctaccaatagggacttttcttcaagc 1261 tcgatcttgatgaaactctgtggttaaaaaatgagatatanccaattataattgataga 1321 ataaaactttattactcccattgagcataacaaaacaaaaaaagtaaagggacttcttc 1381 tcttttttagggagaaattctttgattgtttgttaatatagattcatgtttttttttatt 1441 tctaataataattgtgcttgaatcaggtcgcgctgattcttgcttttagcagcaatag 1501 agtcaaagctaatatacatattatttggttttcgaataagttatactgaaattatataat 1561 acgggtattaaataataacatgattatttataggatatgctttttttattgggtaaatat 1621 atttttttaattaaaaatgaaatatacaagtaaggtataaaacactatttgattttaca 1681 ctagataaatttgccctcgtacatctctaagagaagagctgaaataaatgaattttaaat 1741 ttcagaaaaaaataaattcattagtataatgagatgtcgatacttgacaattactatact 1801 aactagaacaaggttcagcagatagtgacgctaacctattttgtattgaattattctaa 1861 tttgtccacagAGTTTAGTCTTGGATGCTGCGGACACAGTTGCTCTTCACATGAATTGGG
                    S   L   V   L   D   A   A   D   T   V   A   L   H   M   N   W   329

1921 GAATGGCATTATTGATAAACAATCAACATGCCTTGAAGAAAGCGCAAGAAGAGATAGATA
      G   M   A   L   L   I   N   N   Q   H   A   L   K   K   A   Q   E   E   I   D   349

1981 AAAAAGTTGGTAAGGATAGATGGGTAGAAGAGAGTGATATTAAGGATTTGGTATACCTCC
      K   K   V   G   K   D   R   W   V   E   E   S   D   I   K   D   L   V   Y   L   369

2041 AAACTATTGTTAAAGAAGTGTTACGATTATATCCACCGGGACCTTTATTAGTACCCCATG
      Q   T   I   V   K   E   V   L   R   L   Y   P   P   G   P   L   L   V   P   H   389

2101 AAAATGTAGAGGATTGTGTTGTTAGTGGATATCACATTCCTAAAGGGACTAGACTATTCG
      E   N   V   E   D   C   V   V   S   G   Y   H   I   P   K   G   T   R   L   F   409

2161 CGAACGTTATGAAATTACAGCGCGATCCTAAACTCTGGTCAAATCCTGATAAGTTCGATC
      A   N   V   M   K   L   Q   R   D   P   K   L   W   S   N   P   D   K   F   D   429
```

FIGURE 1C

```
2221 CAGAGAGATTTTTCGCTGCTGATATTGACTTTCGTGGTCAACACTATGAGTTTATCCCAT
      P   E   R   F   F   A   A   D   I   D   F   R   G   Q   H   Y   E   F   I   P      449

2281 TTGGTTCTGGAAGACGATCTTGTCCGGGGATGACTTATGCAATGCAAGTGGAACACCTAA
      F   G   S   G   R   R   S   C   P   G   M   T   Y   A   M   Q   V   E   H   L      469

2341 CAATCGCACACTTGATCCAGGGTTTCAATTACAAAACTCCAAATGACGAGCCCTTGGATA
      T   I   A   H   L   I   Q   G   F   N   Y   K   T   P   N   D   E   P   L   D      489

2401 TGAAGGAAGGTGCAGGATTAACTATACGTAAGGTAAATCCTATAGAAGTGGTAATTACGC
      M   K   E   G   A   G   L   T   I   R   K   V   N   P   I   E   V   V   I   T      509

2461 CTCGCCTGACACCTGAGCTTTATtaaaatctaagatgttttatcttggttgatcattgtt
      P   R   L   T   P   E   L   Y                                                      517

2521 taatactcctagatagatgggtattcatctatcttttaaaattaattgtcagtacgagt 2581 gtttctaatttggtaagtttgtaacaacaagtaaagaaggattgtgctagtatgta
```

FIGURE 2A

```
                                                                                                                              100
CYP82E10   aaattatcta taaaagggaa gttggtgata gtttgattcc caagtgcttt tctaaaaatc cataaAGGTT TCTCCCGTAG AAGCCATCGT AGGACTAGTA
CYP82E5v2  .......... .......... ....gattcc caagttcttt tctaaaactc cataaATGTT TCTCCCGTAG AAGCCATTGT AGGACTAGTA
CYP82E4v2  .......... ....aaggaa gttgccgata gttatattct caacttccta cataaATGCTT TCTCCCATAG AAGCCATTGT AGGACTAGTA
                                                                                                                              200
CYP82E10   ACTCTTACAC TTCTCTTCTA CTTCATACGG ACCAAAAAAT CTCAAAAACC TTACCACCGA AAATCCCCGG AGGGTGGCCG GTAATCGGCC
CYP82E5v2  ACCCTTACAC TTCTCTTCTA CTTCCTATGG .......... CCCAAAAAAT TTCAAAACCA TTACCACCGA AAATTCCCGG AGGGGGGCCG GTAATCGGCC
CYP82E4v2  ACCTTCACAT TTCTCTTCTT CTTCCTATGG .......... ACAAAAAAAT TTCAAAACCC TTACCACCGA AAATCCCCGG AGGATGGCCG GTAATCGGCC
                                                                                                                              300
CYP82E10   ATCTTTTCTA TTTCGATGAC CTTCGATGAT GACAGCGACG ACCGTCCATT AGCACGAAAA CTCGGAGACT TAGCTGACAA ATACGGCCCG GTTTTCACTT TTCGGCTAGG
CYP82E5v2  ATCTTTTCTA CTTCGATGAT GACGGCGACG ACCGTCCATT AGCTCGAAAA CTCGGAGACT TAGCTGACAA ATACGGCCCG GTTTTCACTT TCCGGCTAGG
CYP82E4v2  ATCTTTTCCA CTTCAATGAC GACGGCGACG ACCGTCCATT AGCTCGAAAA CTCGGAGACT TAGCTGACAA ATACGGCCCC GTTTTCACTT TTCGGCTAGG
                                                                                                                              400
CYP82E10   CCTTCGGCTT GTGTTAGTTG TAAGCAGTTA CGAAGGCTATA AAACACTGCT TCTCTACAAA TGATGCCATT TTCTCCAATC GTCCAGCTTT TCTTTATGGC
CYP82E5v2  CCTTCGGCTT GTGTTAGTTG TAAGCAGTTA CGAAGCTGTA AAAGACTGCT TCTCTACAAA TGACGGCATT TTCTCCAATC GTCCAGCTTT TCTTTACGGT
CYP82E4v2  CCTTCCCCTT GTCTTAGTTG TAAGCAGTTA CGAAGCTGTA AAAGACTGTT TCTCTACAAA TGACGGCCATT TTCTCCAATC GTCCAGCTTT TCTTTACGGC
                                                                                                                              500
CYP82E10   GAATACCTTG GCTACAATAA TGCCATGCTA TTTTTGACAA AATACGGACC TTACTGGCGA AAAAATAGAA AATTAGTCAT TCAGGAAGTT CTCTGTCCTA
CYP82E5v2  GAATACCTTG GCTACAGTAA TGCCATGCTA TTTTTGACAA AATACGGACC TTATTGGCGA AAAAATAGAA AATTAGTCAT TCAGGAAGTT CTCTCTCTA
CYP82E4v2  GATTACCTTG GCTACAATAA TGCCATGCTA TTTTTGCCCA ATTACGGACC TTACTGGCGA AAAAATCGAA AATTAGTTAT TCAGGAAGTT CTCTCCCCTA
                                                                                                                              600
CYP82E10   GTCGTCTTCA AAAATTGAAG CACGTGAGAT TTGGTCAAAT TCACGCGAGC ATTAAGAATT TATACACTCG AATTCGAGTA CGATAAATCT
CYP82E5v2  GTCGTCTTCA AAAATTGAAG CACGTGAGAT TGGGTAAAAT TCAAACGAGC ATTAAGAATT TATACACTCG AATTCGAGTA CGATAAATCT
CYP82E4v2  GTCGTCTCGA AAATTCAAA  CACGTGAGAT TTGCAAGAAT TCAAGCGAGC ATTAAGAATT TATATACTCG AATTCGAGTA CGATAAATTT
                                                                                                                              700
CYP82E10   AACCGATTGG TTAGAAGAAT TGAATTTTGG TCTGATCGTG AAAATGATCG CTGGGAAAAA TTATGAATCG GGTAAGGAG AATGAACAAGT GGAGAGATTT
CYP82E5v2  AACTGATTGG TTAGAAGAAT TGAATTTGG  TCTGATCGTG AAAATGATCG CTGGGAAAAA TTATGAATCG GGTAAGGAGG ATGAACAAGT GGAGAGATTT
CYP82E4v2  AACTGATTGG TTAGAAGAAT TGAATTTGG  TCTGATCGTG AAGATGATCG CTGGGAAAAA TTATGAATCG GGTAAGGAGG ATGAACAAGT GGAGAGATTT
                                                                                                                              800
CYP82E10   AGGAAAGCGT TTAAGGATTT TATAATTTTA TCAATGGAGT TAGATTCTGT TTGTGTTATG CCAATTCCAT TTTAATCAA CCAAATTCCAA AACATGTCAA GGTGGATTTT CAAGGCCATG
CYP82E5v2  AGGAAAGGGT TTAAGGATTT TATAATTTTA TCAATGGAGT TAGATTCTGT TGTGTTATG  CCAATTCCAT TGTCAATCAA CCAATGTCAA AACATGTCAA GGTGGATTTT CAAGGCCATG
CYP82E4v2  AAGAAAGCGT TTAAGGATTT TATGATTTTA TCAATGGAGT TAGATTCTGT TGTGTTATG  CCAATTCCAT TTTAATAA   CCAATTCCAA AACATATTAA TAAAGAGAA AAAATGGAGG TTAATGCACA
                                                                                                                              900
CYP82E10   TTAAGGCCAT GAAAAGGACA TTTAAGGATT TTTAAGATA  GAATACCAT  TTTAAGGATT AATATCTTGA TGAAGGCTAC CTGTCATAA  AGCAACAGTG
CYP82E5v2  TTAAGGCCAT GAAAAGGACA TTTAAGGATT TTTAAGGATT TAATATCTTGA TGAAGGCTAC CTGTCATAA  AGCAACAGTG
CYP82E4v2  TTAAGGCTAT GAAAAGGACT TTTAAAGATA TAAGATTGG AATATCTTGG TGAAGGTTAC CTGTCATTAA AGCAACCGTG
                                                                                                                              1000
CYP82E10   AGGAAATGAA CAAGATTTCA TTGATGTGT  GCTTTCAAAA ATGAGTAATG AATATCTTGA TGAAGGCTAC CTGTCATAA  AGCAACAGTG
CYP82E5v2  AGGGAATGAA CAAGATTTCA TTGATGTGGT GCTTTCAAAA ATGAGTAATG AATATCTTGA TGAAGGTTAC CTGTCATAAA AGCAACAGTG
CYP82E4v2  AGGGAATGAA CAAGATTTCA TTGATGTGGT GCTTTCAAAA ATGAGTAATG AATATCTTGG TGAAGGTTAC CTGTCATTAA AGCAACCGTG
```

```
                                                                                                      2100
CYP82E10   actatactaa  ctagaacaag  gttcagcaga  tagtgacgct  aacctatttt  tgtattgaat  tat.........  tc  taatttgtcc  acagAGTTTA
CYP82E5v2  actatactaa  atagaacaag  gttcggcaga  tagtgacact  aacctacttt  tgtattgaat  tatcctttt   aatttattc   taatttgtct  acagAGTTTG
CYP82E4v2  actatactaa  ctaaaacaag  gtatgtgaat  aattgatatt  ..ccttttt   ..........  tat.......  .........  tc  ttttt....  ccagAGTTTG
                                                                                                      2200

CYP82E10   GTCTTGGATG  CTGCGGACAC  AGTTGCTCTT  CACATGAATT  GGGGAATGGC  ATTATTGATA  AACAATCAAC  ATGCCTTGAA  GAAAGCGCAA  GAAGAGATAG
CYP82E5v2  GTCTTGGATG  CTGCGGACAC  AGTTGCTCTT  CACATGAATT  GGGGAATGGC  ATTACTGATA  AACAATCAAC  ATGCCTTGAA  GAAAGCACAA  GAAGAGATCG
CYP82E4v2  GTCTTGGATG  CAGCAGACAC  AGTTGCTCTT  CACATAAATT  GGGGAATGGC  ATTATTGATA  AACAATCAAA  AGGCCTTGAC  GAAAGCACAA  GAAGAGATAG
                                                                                                      2300

CYP82E10   ATAAAAAAGT  TGGTAAGGAA  AGATGGGTAG  AAGAGAGTGA  TATTAAGGAT  TTGGTATACC  TCCAAACTAT  TGTTAAAGAA  GTGTTACGAT  TATATCCACC
CYP82E5v2  ATAAAAAAGT  TGGTAAGGAA  AGATGGGTAG  AAGAGAGTGA  TATTAAGGAT  TTGGTCTACC  TCCAAGCTAT  TGTTAAAGAA  GTGTTACGAT  TATATCCACC
CYP82E4v2  ACACAAAAGT  TGGTAAGGAC  AGATGGGTGA  AAGAGAGTGA  TATTAAGGAT  TTGGTATACC  TCCAAGCTAT  TGTTAAAGAA  GTGTTACGAT  TATATCCACC
                                                                                                      2400

CYP82E10   GGGACCTTTA  TTAGTACCCC  ATGAAAATGT  GTTGTTAGTG  GATATCACAT  TCCTAAAGGG  GCTGATATTG  TCGCGAACGT  ACTAGACTAT  TATGAAATTA
CYP82E5v2  AGGACCTTTA  TAGTACCTC   ATGAAAATGT  GTTGTTAGTG  GATATCACAT  TCCTAAAGGG  GATGATATTG  TCGCGAACGT  ACTAGACTAT  TATGAAATTG
CYP82E4v2  AGGACCTTTG  TTAGTACCAC  ACGAAAATGT  GTTGTTAGTG  GATATCACAT  TCCTAAAGGG  ACTGATATTG  TCGCAAACGT  ACAAGATTAT  CATGAAACTG
                                                                                                      2500

CYP82E10   CAGGCGGATC  GTCAAATCCT  ATCAAAATGT  AGAGATTGT   ATCCAGAGAG  ATTTTCGCT   ACTTCGTGG   TCAACACTAT  CAGTTTATCC  GAGTTTATCC
CYP82E5v2  CAGGCGGATC  GTCAAATCCT  ATCAAAATGT  AGAGATTGT   ATCCAGAGAG  ATCTCGCT    ACTTCGTGG   TCAACACTAT  GAGTTTATCC  GAGTTTATCC
CYP82E4v2  CAACGTGATC  GTCTGATCCT  ACGAAAATGT  AGAAGATTGT  ATCCAGAGAG  ATTCATTGCT  ACTTCGTGG   ACAAGATTAT  CATGAAACTG  AAGTATATCC
                                                                                                      2600

CYP82E10   CATTGGTTC   TCTTGTCCGG  GGATGACTTA  TGCAATGCAA  GTGGAACACC  TAACAATCGC  ACACTTGATC  CAGGGTTTCA  ATTACAAAAC
CYP82E5v2  CATTGGTTC   TCTTGTCCGG  GGATGACTTA  TGCATTACAA  GTGGAACACC  TAACAATAGC  ACATTTGATC  CAGGGTTTCA  ATTACAAAAC
CYP82E4v2  CGTTTGGTTC  TCTTGTCCAG  GGATGACTTA  TGCATTGCAA  GTGGAACACT  TAACAATGGC  ACATTTGATC  CAAGGTTTCA  ATTACAGAAC
                                                                                                      2700

CYP82E10   TCCAAATGAC  GAGCCCCTTGG  ATATGAAGGA  TTAACTATAC  GTAAGGTAAA  TCCTATAGAA  GTGGTAATTA  CGCCTCGCCT  GACACCTGAG
CYP82E5v2  TCCAAATGAC  GAGCCCTTGG  ATATGAAGGA  TTAACTATAC  GTAAAGTAAA  TCCTGTAGAA  GTGACAATTA  CGGCTCGCCT  GGCACCTGAG
CYP82E4v2  TCCAAATGAC  GAGCCCTTGG  ATATGAAGGA  ATAACTATAC  AGGTGCAGGC  ATAAGGTAAA  CCCTGTGGAA  CTGATAATAG  CGCCTCGCCT  GGCACCTGAG
                                                                                                      2800

CYP82E10   CTTTATTAAa  atctaagatg  ttttatcttg  gttgatcatt  gtttaatact  cctagataga  tgggtattca  tctatctttt  taaaattaat  tgtcagtacg
CYP82E5v2  CTTTATTAAa  accttagatg  ttttatcttg  attgtac..t  aatatatata  gcagaaaa..  ..........  ..........  ..........  ..........
CYP82E4v2  CTTTATTAAa  acctaagatc  tttcatcttg  gttgatcatt  gtataatact  cctaaa...   tgggatattca  tttaccttt   atcaattaat  tgtcagtacg
                                                                            2860

CYP82E10   agtgtttcta  atttggtaag  tttgtaacaa  caagtaaaga  aggattgtgc  tagtatgta.
CYP82E5v2  ..........  ..........  ..........  ..........  ..........  ..........
CYP82E4v2  agtttttcta  atttggtaca  tttgtaataa  taagtaaaga  ataattgtgc  atattgtgta
```

FIGURE 3
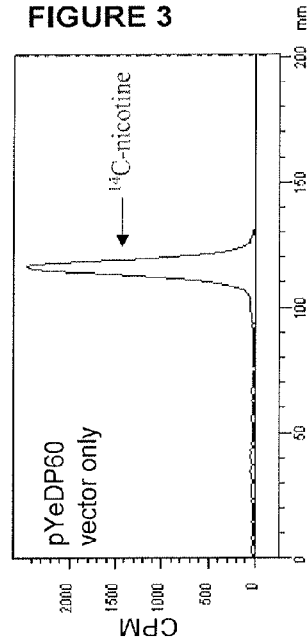
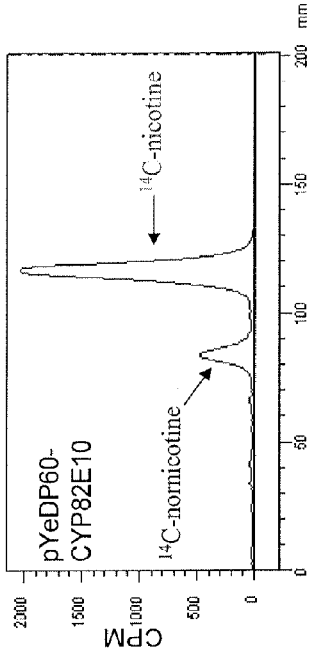
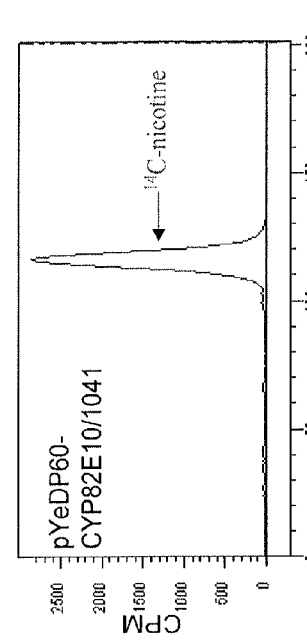
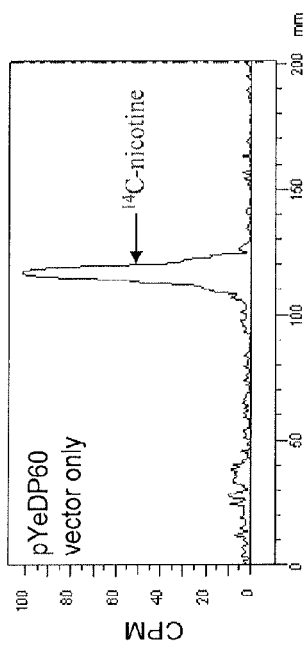
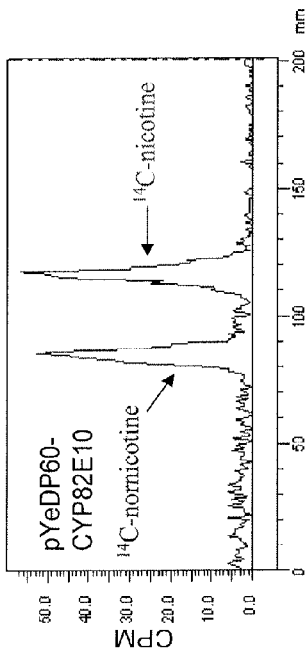
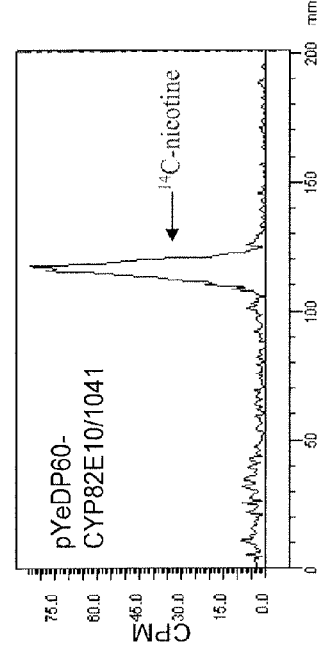

FIGURE 4A
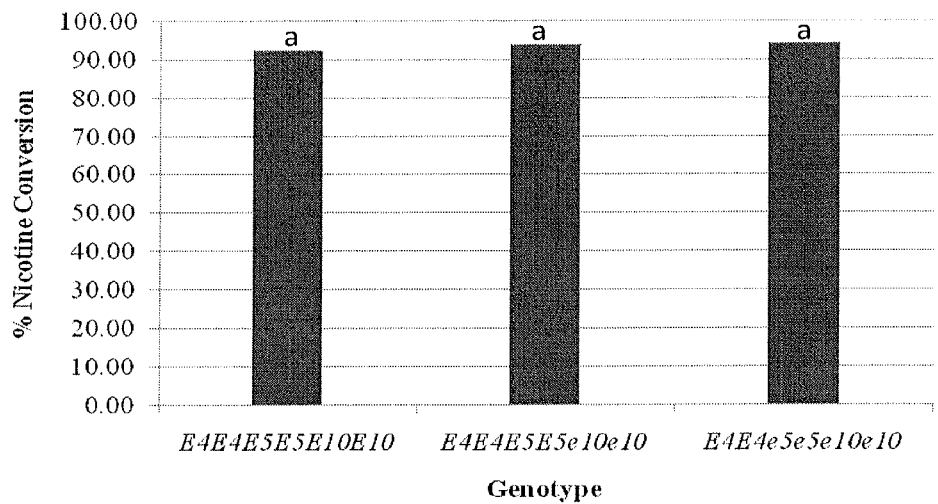
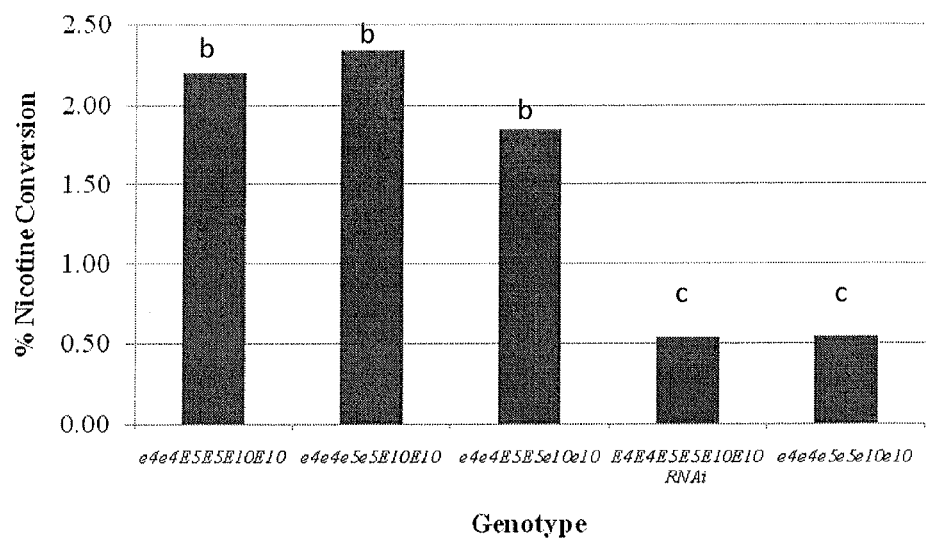
FIGURE 4B

US 9,247,706 B2

COMPOSITIONS AND METHODS FOR MINIMIZING NORNICOTINE SYNTHESIS IN TOBACCO

CROSS-REFERENCE TO RELATED APPLICATIONS

This application is the U.S. National Stage of International Application No. PCT/US2011/021088, filed Jan. 13, 2011, which designates the U.S and was published by the International Bureau in English on Jul. 21, 2011, and which claims the benefit of U.S. Provisional Patent Application No. 61/295,671, filed Jan. 15, 2010; the contents of each of which are hereby incorporated herein in their entirety by reference.

INCORPORATION OF SEQUENCE LISTING

An official copy of the Sequence Listing is submitted electronically via EFS-Web as an ASCII formatted Sequence Listing with a file named "13521766SeqListReplacement-.txt," created on Jan. 20, 2015, having a size of 150 KB and is filed concurrently with the substitute specification. The Sequence Listing contained in this ASCII formatted document is part of the specification and is herein incorporated by reference in its entirety.

FIELD OF THE INVENTION

The invention relates to compositions and methods for minimizing nornicotine synthesis, and hence its metabolite N'-nitrosonornicotine, in tobacco plants and plant parts thereof, particularly compositions and methods for inhibiting expression or function of a root-specific nicotine demethylase in combination with a green leaf and a senescence-induced nicotine demethylase.

BACKGROUND OF THE INVENTION

The predominant alkaloid found in commercial tobacco varieties is nicotine, typically accounting for 90-95% of the total alkaloid pool. The remaining alkaloid fraction is comprised primarily of three additional pyridine alkaloids: nornicotine, anabasine, and anatabine. Nornicotine is generated directly from nicotine through the activity of the enzyme nicotine N-demethylase. Nornicotine usually represents less than 5% of the total pyridine alkaloid pool, but through a process termed "conversion," tobacco plants that initially produce very low amounts of nornicotine give rise to progeny that metabolically "convert" a large percentage of leaf nicotine to nornicotine. In tobacco plants that have genetically converted (termed "converters"), the great majority of nornicotine production occurs during the senescence and curing of the mature leaf (Wernsman and Matzinger (1968) *Tob. Sci.* 12:226-228). Burley tobaccos are particularly prone to genetic conversion, with rates as high as 20% per generation observed in some cultivars.

During the curing and processing of the tobacco leaf, a portion of the nornicotine is metabolized to the compound N-nitrosonornicotine (NNN), a tobacco-specific nitrosamine (TSNA) that has been asserted to be carcinogenic in laboratory animals (Hecht and Hoffmann (1990) *Cancer Surveys* 8:273-294; Hoffmann et al. (1994) *J. Toxicol. Environ. Health* 41:1-52; Hecht (1998) *Chem. Res. Toxicol.* 11:559-603). In flue-cured tobaccos, TSNAs are found to be predominantly formed through the reaction of alkaloids with the minute amounts of nitrogen oxides present in combustion gases formed by the direct-fired heating systems found in traditional curing barns (Peele and Gentry (1999) "Formation of Tobacco-specific Nitrosamines in Flue-cured Tobacco," CORESTA Meeting, Agro-Phyto Groups, Suzhou, China). Retrofitting these curing barns with heat-exchangers virtually eliminated the mixing of combustion gases with the curing air and dramatically reduced the formation of TSNAs in tobaccos cured in this manner (Boyette and Hamm (2001) *Rec. Adv. Tob. Sci.* 27:17-22.). In contrast, in the air-cured Burley tobaccos, TSNA formation proceeds primarily through reaction of tobacco alkaloids with nitrite, a process catalyzed by leaf-borne microbes (Bush et al. (2001) *Rec. Adv. Tob. Sci.* 27:23-46). Thus far, attempts to reduce TSNAs through modification of curing conditions while maintaining acceptable quality standards have not proven to be successful for the air-cured tobaccos.

Aside from serving as a precursor for NNN, recent studies suggest that the nornicotine found in tobacco products may have additional undesirable health consequences. Dickerson and Janda (2002) *Proc. Natl. Acad. Sci. USA* 99: 15084-15088 demonstrated that nornicotine causes aberrant protein glycation within the cell. Concentrations of nornicotine-modified proteins were found to be much higher in the plasma of smokers compared to nonsmokers. This same study also showed that nornicotine can covalently modify commonly prescribed steroid drugs such as prednisone. Such modifications have the potential of altering both the efficacy and toxicity of these drugs. Furthermore, studies have been reported linking the nornicotine found in tobacco products with age-related macular degeneration, birth defects, and periodontal disease (Brogan et al. (2005) *Proc. Natl. Acad. Sci. USA* 102: 10433-10438; Katz et al. (2005) *J. Periodontol.* 76: 1171-1174).

In Burley tobaccos, a positive correlation has been found between the nornicotine content of the leaf and the amount of NNN that accumulates in the cured product (Bush et al. (2001) *Rec. Adv. Tob. Sci,* 27:23-46; Shi et al. (2000) *Tob. Chem. Res. Conf.* 54:Abstract 27). Therefore, strategies that could effectively reduce the nornicotine content of the leaf would not only help ameliorate the potential negative health consequences of the nornicotine per se as described above, but should also concomitantly reduce NNN levels. This correlation was further solidified in the recent study by Lewis et al. (2008) *Plant Biotech. J.* 6: 346-354 who demonstrated that lowering nornicotine levels using an RNAi transgene construct directed against the CYP82E4v2 gene, which encodes a senescence-induced nicotine demethylase, lead to concomitant reductions in the NNN content of the cured leaf. Although this study demonstrated that transgenic technologies can be used to greatly reduce the nornicotine and NNN content of tobacco, a combination of public perception and intellectual property issues make it very difficult for commercialization of products derived from transgenic plants.

Therefore a great need exists for a means to effectively minimize nornicotine accumulation in tobacco that does not rely on the use of transgenics.

SUMMARY OF THE INVENTION

Compositions and methods for minimizing the nornicotine content in tobacco plants and plant parts thereof are provided. Compositions include an isolated root-specific cytochrome P450 polynucleotide designated the CYP82E10 polynucleotide, as set forth in SEQ ID NO:1, and CYP82E10 nicotine demethylase polypeptide encoded thereby, as set forth in SEQ ID NO:2, and variants and fragments thereof, including, but not limited to, polypeptides comprising the sequence set forth in SEQ ID NO:5, 6, 7, 8, 9, 10, 11, 12, or 13, as well as polynucleotides encoding the polypeptide set forth in SEQ ID NO:5, 6, 7, 8, 9, 10, 11, 12, or 13. The CYP82E10 polypeptide of the invention is a nicotine demethylase that is involved in the metabolic conversion of nicotine to nornicotine in the roots of tobacco plants. Isolated polynucleotides of the invention also include a polynucleotide comprising the sequence set forth in SEQ ID NO:3 or 4, and variants and fragments thereof. Compositions of the invention also include tobacco plants, or plant parts thereof, comprising a mutation in a gene encoding a CYP82E10 nicotine demethylase, wherein the mutation results in reduced expression or function of the CYP82E10 nicotine demethylase. In some embodiments, the tobacco plants of the invention further comprise a mutation in a gene encoding a CYP82E4 nicotine demethylase and/or a mutation in a gene encoding a CYP82E5 nicotine demethylase, wherein the mutation within these genes results in reduced expression or function of the CYP82E4 or CYP82E5 nicotine demethylase. Seed of these tobacco plants, or progeny thereof, and tobacco products prepared from the tobacco plants of the invention, or from plant parts or progeny thereof, are also provided.

Methods for reducing the level of nornicotine, or reducing the rate of conversion of nicotine to nornicotine, in a tobacco plant, or plant part thereof are also provided. The methods comprise introducing into the genome of a tobacco plant a mutation within at least one allele of each of at least three nicotine demethylase genes, wherein the mutation reduces expression of the nicotine demethylase gene, and wherein a first of these nicotine demethylase genes encodes a root-specific nicotine demethylase involved in the metabolic conversion of nicotine to nornicotine in a tobacco plant or a plant part thereof. In some embodiments, the root-specific nicotine demethylase is CYP82E10 or variant thereof. In other embodiments, these methods comprise introducing into the genome of a tobacco plant a mutation within at least one allele of a nicotine demethylase gene encoding CYP82E10 or variant thereof, and a mutation within at least one allele of a nicotine demethylase encoding CYP82E4 or variant thereof, and/or a nicotine demetylase encoding CYP82E5 or variant thereof. Methods for identifying a tobacco plant with low levels of nornicotine are also provided, wherein the plant or plant part thereof is screened for the presence of a mutation in a gene encoding CYP82E10 or variant thereof, alone or in combination with screening for the presence of a mutation in a gene encoding CYP82E4 or variant thereof, and/or the presence of a mutation in a gene encoding CYP82E5 or variant thereof.

The following embodiments are encompassed by the present invention.

1. A tobacco plant, or plant part thereof, comprising a mutation in a gene encoding a CYP82E10 nicotine demethylase, wherein said mutation results in reduced expression or function of said CYP82E10 nicotine demethylase.

2. The tobacco plant, or plant part thereof, according to embodiment 1, wherein said CYP82E10 nicotine demethylase is selected from the group consisting of the sequence set forth in SEQ ID NO:2, 5, 6, 7, 8, and 9.

3. The tobacco plant, or plant part thereof, according to embodiment 1 or 2, wherein said mutation results in a modification of said CYP82E10 nicotine demethylase occurring at a position selected from the group consisting of amino acid residues 79, 107, 381, 419, and any combination thereof, wherein said numbering is according to SEQ ID NO:2.

4. The tobacco plant, or plant part thereof, according to embodiment 3, wherein said mutation is selected from the group consisting of:

a) a serine substitution for the glycine residue at position 79;
b) a serine substitution for the proline residue at position 107;
c) a serine substitution for the proline residue at position 381;
d) a serine substitution for the proline residue at position 419; and
e) any combination thereof.

5. The tobacco plant, or plant part thereof, according to any of embodiments 1-4, further comprising a mutation in a gene encoding a CYP82E4 nicotine demethylase, wherein said mutation results in reduced expression or function of said CYP82E4 nicotine demethylase.

6. The tobacco plant, or plant part thereof, according to embodiment 5, wherein said CYP82E4 nicotine demethylase is selected from the sequence set forth in SEQ ID NO:14, 15, 16, 17, 18, 19, and 20.

7. The tobacco plant, or plant part thereof, according to embodiment 5 or 6, wherein said mutation results in a modification of said CYP82E4 nicotine demethylase occurring at a position selected from the group consisting of amino acid residues 329, 364, 376, 381, and 458, wherein said numbering is according to SEQ ID NO:14.

8. The tobacco plant, or plant part thereof, according to embodiment 7, wherein said mutation is selected from the group consisting of:

a) a stop codon substitution for the tryptophan residue at position 329;
b) an asparagine substitution for the lysine residue at position 364;
c) a methionine substitution for the valine residue at position 376;
d) a serine substitution for the proline residue at position 381;
d) a serine substitution for the proline residue at position 458; and
e) any combination thereof.

9. The tobacco plant, or plant part thereof, according to any of embodiments 1-8, further comprising a mutation in a gene encoding a CYP82E5 nicotine demethylase, wherein said mutation results in reduced expression or function of said CYP82E5 nicotine demethylase.

10. The tobacco plant, or plant part thereof, according to embodiment 9, wherein said CYP82E5 nicotine demethylase is selected from the sequence set forth in SEQ ID NO:26, 27, 28, 29, 30, 31, and 32.

11. The tobacco plant, or plant part thereof, according to embodiment 9 or 10, wherein said mutation results in a modification of said CYP82E5 nicotine demethylase occurring at a position selected from the group consisting of amino acid residues 422 and 449, wherein said numbering is according to SEQ ID NO:26.

12. The tobacco plant, or plant part thereof, according to embodiment 11, wherein said mutation is selected from the group consisting of:

a) a stop codon substituted for the tryptophan residue at position 422;
b) a leucine substituted for the proline residue at position 449; and
c) any combination thereof.

13. The tobacco plant, or plant part thereof, according to any of embodiments 9-12, comprising a mutation in said CYP82E10 nicotine demethylase gene and said CYP82E4 nicotine demethylase gene.

14. The tobacco plant, or plant part thereof, according to any of embodiments 1-13, wherein said tobacco plant, or plant part thereof, is homozygous for said mutation.

15. The tobacco plant, or plant part thereof, according to embodiment 14, wherein said CYP82E10 nicotine demethylase comprises a mutation at position 381, said CYP82E4 nicotine demethylase comprises a mutation at position 329, and said CYP82E5 nicotine demethylase comprises a mutation at position 422, wherein said numbering is according to SEQ ID NO:2, 14, and 26, respectively.

16. The tobacco plant, or plant part thereof, according to embodiment 15, wherein said mutation is selected from the group consisting of:
   a) a serine substitution for the proline residue at position 381;
   b) a stop codon substitution for the tryptophan residue at position 329;
   c) a stop codon substitution for the tryptophan residue at position 422; and
   d) any combination thereof.

17. The tobacco plant, or plant part thereof, according to any of embodiments 13-16, wherein said plant or plant part thereof has less than 1.5% conversion of nicotine to nornicotine.

18. The tobacco plant, or plant part thereof, according to embodiment 17, wherein said plant or plant part thereof has no more than 0.5% conversion of nicotine to nornicotine.

19. Seed of the tobacco plant according to any of embodiments 1-18, or progeny thereof.

20. A tobacco product prepared from a tobacco plant, or plant part or progeny thereof, according to any of embodiments 1-19.

21. A method for reducing a carcinogenic potential of a tobacco product, said method comprising preparing said tobacco product from a tobacco plant, or plant part or progeny thereof, according to any of embodiments 1-18.

22. A method for reducing the level of nornicotine, or reducing the rate of conversion of nicotine to nornicotine, in a tobacco plant, or a plant part thereof, said method comprising introducing into the genome of said plant a mutation within at least one allele of each of at least three nicotine demethylase genes, wherein said mutation reduces expression of said nicotine demethylase gene, and wherein a first of said nicotine demethylase genes encodes a root-specific nicotine demethylase involved in the metabolic conversion of nicotine to nornicotine in a tobacco plant or a plant part thereof.

23. The method of embodiment 22, wherein said root-specific nicotine demethylase is a CYP82E10 nicotine demethylase comprising an amino acid sequence selected from the group consisting of:
   a) the amino acid sequence set forth in SEQ ID NO:2, 5, 6, 7, 8, 9, or 10; and
   b) an amino acid sequence having at least 98% sequence identity to the amino acid sequence set forth in SEQ ID NO:2, 5, 6, 7, 8, 9, or 10.

24. The method of embodiment 23, wherein said amino acid sequence for said CYP82E10 nicotine demethylase has a substitution at an amino acid residue in a position selected from the group consisting of residues 79, 107, 381, 419, and any combination thereof, where the numbering is according to SEQ ID NO:2.

25. The method of embodiment 24, wherein said substitution at position 79, 107, 381, or 419 is a serine residue.

26. The method of any one of embodiments 22-25, wherein a second of said nicotine demethylase genes encodes a CYP82E4 nicotine demethylase.

27. The method of embodiment 26, wherein said CYP82E4 nicotine demethylase comprises an amino acid sequence selected from the group consisting of:
   a) the amino acid sequence set forth in SEQ ID NO:14, 15, 16, 17, 18, 19, 20, or 21; and
   b) an amino acid sequence having at least 98% sequence identity to the sequence set forth in SEQ ID NO:14, 15, 16, 17, 18, 19, 20, or 21.

28. The method of embodiment 27, wherein said amino acid sequence for said CYP82E4 nicotine demethylase has a substitution at an amino acid residue in a position selected from the group consisting of residues 329, 364, 381, 458, and any combination thereof, where the numbering is according to SEQ ID NO:14.

29. The method of embodiment 28, wherein said substitution at position 329 is a stop codon, said substitution at position 364 is an asparagine residue, said substitution at position 381 is a serine residue, said substitution at position 458 is a serine residue, or any combination thereof.

30. The method of any one of embodiments 22-29, wherein a third of said nicotine demethylase genes encodes a CYP82E5 nicotine demethylase.

31. The method of embodiment 30, wherein said CYP82E5 nicotine demethylase comprises an amino acid sequence selected from the group consisting of:
   a) the amino acid sequence set forth in SEQ ID NO:26, 27, 28, 29, 30, 31, or 32; and
   b) an amino acid sequence having at least 98% sequence identity to the sequence set forth in SEQ ID NO: 26, 27, 28, 29, 30, 31, or 32.

32. The method of embodiment 31, wherein said amino acid sequence for said CYP82E5 nicotine demethylase has a substitution at an amino acid residue in a position selected from the group consisting of residues 422 and 449, and any combination thereof, where the numbering is according to SEQ ID NO:26.

33. The method of embodiment 32, wherein said substitution at position 422 is a stop codon, said substitution at position 449 is a leucine residue, or any combination thereof.

34. The method of any one of embodiments 22-33, wherein said plant or plant part thereof is homozygous for said mutation.

35. The method of any one of embodiments 22-34, wherein said introducing comprises a breeding protocol.

36. The method of any one of embodiments 22-35, wherein said plant is a Burley, Virginia, flue-cured, air-cured, fire-cured, Oriental, or a dark tobacco plant.

37. The tobacco plant, or plant part thereof, according to any of embodiments 1-18, wherein said tobacco plant is a Burley, Virginia, flue-cured, air-cured, fire-cured, Oriental, or a dark tobacco plant.

38. A method for identifying a tobacco plant with low levels of nornicotine, said method comprising screening a DNA sample from a tobacco plant of interest for the presence of a mutation in SEQ ID NO:1 or 3.

39. The method according to embodiment 38, wherein said tobacco plant is a nonconverter.

40. The method according to embodiment 38 or 39, wherein said screening is carried out using a sequence selected from the group consisting of SEQ ID NOS:1, 3, 35, 36, 37, and 38.

41. The method according to any one of embodiments 38-40, further comprising screening said DNA sample, or another DNA sample from said tobacco plant of interest, for the presence of a mutation in SEQ ID NO:14, the presence of a mutation in SEQ ID NO:26, or the presence of a mutation in SEQ ID NO:14 and SEQ ID NO:26.

42. An isolated polynucleotide comprising a nucleotide sequence selected from the group consisting of:
   a) a nucleotide sequence comprising SEQ ID NO:1, 3, or 4;
   b) a nucleotide sequence comprising a fragment of at least 20 consecutive nucleotides of SEQ ID NO:1, 3, or 4;
   c) a nucleotide sequence having at least 97% sequence identity to the entirety of the sequence set forth in SEQ ID NO:1, wherein said polynucleotide encodes a polypeptide involved in the metabolic conversion of nicotine to nornicotine in a plant;
   d) a nucleotide sequence encoding a polypeptide selected from the group consisting of SEQ ID NOS:2 and 5-13, or a fragment thereof comprising at least 115 contiguous residues;
   e) a nucleotide sequence encoding a polypeptide having at least 98% sequence identity to the sequence set forth in SEQ ID NO:2, 5, 6, 7, 8, 9, 10, 11, 12, or 13; and
   f) a nucleotide sequence that is complementary to the sequence according to any of preceding items (a) through (e).

43. An isolated polypeptide comprising an amino acid sequence selected from the group consisting of:
   a) an amino acid sequence set forth in SEQ ID NO:2, 5, 6, 7, 8, 9, 10, 11, 12, or 13;
   b) an amino acid sequence that is at least 98% identical to an amino acid sequence set forth in SEQ ID NO:2, 5, 6, 7, 8, 9, 10, 11, 12, or 13; and
   c) an amino acid sequence that is a fragment of the amino acid sequence set forth in SEQ ID NO:2, 5, 6, 7, 8, 9, 10, 11, 12, or 13, wherein said fragment comprises at least 115 contiguous residues of the amino acid sequence of SEQ ID NO:2, 5, 6, 7, 8, 9, 10, 11, 12, or 13.

44. A tobacco plant, or plant part thereof that is homozygous for a mutation in a gene encoding a CYP82E10 nicotine demethylase, a gene encoding a CYP82E4 nicotine demethylase, and a gene encoding a CYP82E5 nicotine demethylase, wherein said mutation results in reduced expression or function of said CYP82E10, CYP82E4, and CYP82E5 nicotine demethylase, wherein said CYP82E10 nicotine demethylase comprises a mutation at position 381, said CYP82E4 nicotine demethylase comprises a mutation at position 329, and said CYP82E5 nicotine demethylase comprises a mutation at position 422, wherein said numbering is according to SEQ ID NO:2, 14, and 26, respectively.

45. A mutation in a gene encoding a CYP82E10 nicotine demethylase, wherein said mutation results in reduced expression or function of said CYPe2E10 nicotine demethylase.

46. A plant having a mutation in a CYP82E10 gene that inhibits nicotine demethylase activity in roots, a mutation in a CYP82E4v2 gene that inhibits nicotine demethylase activity in senescent leaves, and a mutation in a CYP83E5 gene that inhibits nicotine demethylase activity in green leaves.

BRIEF DESCRIPTION OF DRAWINGS

FIG. 1A-C shows the DNA (SEQ ID NO:4) and predicted protein sequences of the CYP82E10 nicotine demethylase gene. The protein coding sequences are in uppercase, and 5' and 3' flanking sequences are in lowercase. The intron sequence (SEQ ID NO:3) is lowercase italicized. Numbers for the nucleotide sequence are shown on the left and numbers for the protein sequence are labeled on the right. Nucleotide sequences corresponding to the PCR primers used to specifically amplify exon 1 for mutation screening are underlined (not shown in bold), whereas underlined sequences in bold denote the exon 2-specific primer sites. Individual nucleotide and amino acid residues that were found to be altered in the mutation screen (Table 2) are underlined and in bold.

FIG. 2A-C shows an alignment of genomic sequences for CYP82E10 (SEQ ID NO:4), CYP82E5v2 (SEQ ID NO:38), and CYP82E4v2 (SEQ ID NO:37). Protein-encoding sequences are in upper case type; 5' and 3' untranslated regions are indicated in lower case type; and intron sequences are shown in lower case italicized type. Positions of shared sequence identity are box shaded.

FIG. 3 shows thin layer chromatographic data of nicotine demethylase activities of microsomal membranes from yeast cells expressing CYP82E10, and CYP82E10 possessing the Pro381Ser (P381S) mutation from plant 1041. CPM, counts per minute.

FIGS. 4A and 4B show mean percent nicotine conversion for burley tobacco plants with varying mutant combinations at CYP82E4v2, CYP82E5v2, and CYP82E10 loci. Means with different letters are significantly different at the $P<0.05$ level.

DESCRIPTION OF THE SEQUENCES OF THE SEQUENCE LISTING

The following listing sets forth the sequence information for the Sequence Listing. Standard notation for amino acid substitutions is used. Thus, for example, CYP82E10 P419S indicates the variant protein has a serine substitution for the proline residue at position 419, where the numbering is with respect to the wild-type sequence, in this case, the CYP82E10 sequence set forth in SEQ ID NO:2. As another example, CYP82E4 P38L indicates the variant protein has a leucine substitution for the proline residue at position 38, where the numbering is with respect to the wild-type sequence, in this case, the CYP82E4 sequence set forth in SEQ ID NO:14. As yet another example, CYP82E5 P72L indicates the variant protein has a leucine substitution for the proline residue at position 72, where the numbering is with respect to the wild-type sequence, in this case, the CYP82E5 sequence set forth in SEQ ID NO:26.

SEQ ID NO:1 sets forth a coding sequence for CYP82E10.
SEQ ID NO:2 sets forth the amino acid sequence for CYP82E10.
SEQ ID NO:3 sets forth the nucleotide sequence of an intron of the CYP82E10 gene.
SEQ ID NO:4 sets forth the genomic sequence for CYP82E10.
SEQ ID NO:5 sets forth the amino acid sequence for CYP82E10 L148F.
SEQ ID NO:6 sets forth the amino acid sequence for CYP82E10 G172R.
SEQ ID NO:7 sets forth the amino acid sequence for CYP82E10 A344T.
SEQ ID NO:8 sets forth the amino acid sequence for CYP82E10 A410T.
SEQ ID NO:9 sets forth the amino acid sequence for CYP82E10 R417H.
SEQ ID NO:10 sets forth the amino acid sequence for CYP82E10 P419S.
SEQ ID NO:11 sets forth the amino acid sequence for CYP82E10 G79S.
SEQ ID NO:12 sets forth the amino acid sequence for CYP82E10 P107S.
SEQ ID NO:13 sets forth the amino acid sequence for CYP82E10 P381S.
SEQ ID NO:14 sets forth the amino acid sequence for CYP82E4.

SEQ ID NO:15 sets forth the amino acid sequence for CYP82E4 P38L.

SEQ ID NO:16 sets forth the amino acid sequence for CYP82E4 D171N.

SEQ ID NO:17 sets forth the amino acid sequence for CYP82E4 E201K.

SEQ ID NO:18 sets forth the amino acid sequence for CYP82E4 R169Q.

SEQ ID NO:19 sets forth the amino acid sequence for CYP82E4 G459R.

SEQ ID NO:20 sets forth the amino acid sequence for CYP82E4 T427I.

SEQ ID NO:21 sets forth the amino acid sequence for CYP82E4 V376M.

SEQ ID NO:22 sets forth the amino acid sequence for CYP82E4 W329Stop.

SEQ ID NO:23 sets forth the amino acid sequence for CYP82E4 K364N.

SEQ ID NO:24 sets forth the amino acid sequence for CYP82E4 P381S.

SEQ ID NO:25 sets forth the amino acid sequence for CYP82E4 P458S.

SEQ ID NO:26 sets forth the amino acid sequence for CYP82E5.

SEQ ID NO:27 sets forth the amino acid sequence for CYP82E5 P72L.

SEQ ID NO:28 sets forth the amino acid sequence for CYP82E5 L143F.

SEQ ID NO:29 sets forth the amino acid sequence for CYP82E5 S174L.

SEQ ID NO:30 sets forth the amino acid sequence for CYP82E5 M224I.

SEQ ID NO:31 sets forth the amino acid sequence for CYP82E5 P235S.

SEQ ID NO:32 sets forth the amino acid sequence for CYP82E5 A410V.

SEQ ID NO:33 sets forth the amino acid sequence for CYP82E5 W422Stop.

SEQ ID NO:34 sets forth the amino acid sequence for CYP82E5 P449L.

SEQ ID NO:35 sets forth the forward primer sequence for exon 1 of CYP82E10.

SEQ ID NO:36 sets forth the reverse primer sequence for exon 1 of CYP82E10.

SEQ ID NO:37 sets forth the forward primer sequence for exon 2 of CYP82E10.

SEQ ID NO:37 sets forth the reverse primer sequence for exon 2 of CYP82E10.

SEQ ID NO:38 sets forth the genomic sequence for CYP82E4v2.

SEQ ID NO:39 sets forth the genomic sequence for CYP82E5v2.

DEFINITIONS

The present invention includes compositions and methods for inhibiting expression or function of root-specific nicotine demethylase polypeptides that are involved in the metabolic conversion of nicotine to nornicotine in the roots of a plant, particularly plants of the *Nicotiana* genus, including tobacco plants of various commercial varieties.

As used herein, "inhibit," "inhibition" and "inhibiting" are defined as any method known in the art or described herein, which decreases the expression or function of a gene product of interest (i.e., the target gene product), in this case a nicotine demethylase, such as a root-specific nicotine demethylase of the invention. It is recognized that nicotine demethylase polypeptides can be inhibited by any suitable method known in the art, including sense and antisense suppression, RNAi suppression, knock out approaches such as mutagenesis, and the like. Of particular interest are methods that knock out, or knock down, expression and/or function of these root-specific nicotine demethylases, particularly mutagenic approaches that allow for selection of favorable mutations in the CYP82E10 nicotine demethylase gene.

By "favorable mutation" is intended a mutation that results in a substitution, insertion, deletion, or truncation of the CYP82E10 polypeptide such that its nicotine demethylase activity is inhibited. In some embodiments, the nicotine demethylase activity is inhibited by at least 25%, 30%, 35, 40%, 45, 50%, 55%, or 60% when compared to the activity of the wild-type CYP82E10 polypeptide under the same test conditions. In other embodiments, the nicotine demethylase activity is inhibited by at least 65%, 70%, 75%, 80%, 85%, 90%, or 95%. In preferred embodiments, the favorable mutation provides for complete inhibition (i.e., 100% inhibition), and the nicotine demethylase activity is knocked out (i.e., its activity cannot be measured).

"Inhibiting" can be in the context of a comparison between two plants, for example, a genetically altered plant versus a wild-type plant. The comparison can be between plants, for example, a wild-type plant and one of which lacks a DNA sequence capable of producing a root-specific nicotine demethylase that converts nicotine to nornicotine. Inhibition of expression or function of a target gene product also can be in the context of a comparison between plant cells, organelles, organs, tissues or plant parts within the same plant or between different plants, and includes comparisons between developmental or temporal stages within the same plant or plant part or between plants or plant parts.

"Inhibiting" can include any relative decrement of function or production of a gene product of interest, in this case, a root-specific nicotine demethylase, up to and including complete elimination of function or production of that gene product. When levels of a gene product are compared, such a comparison is preferably carried out between organisms with a similar genetic background. Preferably, a similar genetic background is a background where the organisms being compared share 50% or greater, more preferably 75% or greater, and, even more preferably 90% or greater sequence identity of nuclear genetic material. A similar genetic background is a background where the organisms being compared are plants, and the plants are isogenic except for any genetic material originally introduced using plant transformation techniques or a mutation generated by human intervention. Measurement of the level or amount of a gene product may be carried out by any suitable method, non-limiting examples of which include, but are not limited to, comparison of mRNA transcript levels, protein or peptide levels, and/or phenotype, especially the conversion of nicotine to nornicotine. As used herein, mRNA transcripts can include processed and non-processed mRNA transcripts, and polypeptides or peptides can include polypeptides or peptides with or without any post-translational modification.

As used herein, "variant" means a substantially similar sequence. A variant can have different function or a substantially similar function as a wild-type polypeptide of interest. For a nicotine demethylase, a substantially similar function is at least 99%, 98%, 97%, 95%, 90%, 85%, 80%, 75%, 60%, 50%, 25% or 15% of wild-type enzyme function of converting nicotine to nornicotine under the same conditions or in a near-isogenic line. A wild-type CYP82E10 is set forth in SEQ ID NO:2. A wild-type CYP82E4 is set forth in SEQ ID NO:14. A wild-type CYP82E5 is set forth in SEQ ID NO:26.

Exemplary variants of the wild-type CYP82E10 of the present invention include polypeptides comprising the sequence set forth in SEQ ID NO:5, 6, 7, 8, 9, 10, 11, 12, or 13. The variant set forth in SEQ ID NO:10 (CYP82E10 P419S) advantageously has a favorable mutation that results in the enzyme having only about 25% of the nicotine demethylase activity of the wild-type CYP82E10 polypeptide. The variants set forth in SEQ ID NOs: 11 (CYP82E10 G79S), 12 (CYP82E10 with P107S), and 13 (CYP82E10 with P381S) advantageously have favorable mutations that result in their nicotine demethylase activity being knocked out (i.e., 100% inhibition, and thus a nonfunctional polypeptide). In like manner, exemplary variants of the wild-type CYP82E4 include polypeptides comprising the sequence set forth in SEQ ID NO:15, 16, 17, 18, 19, 20, 21, 22, 23, 24, or 25. The variant set forth in SEQ ID NO:21 (CYP82E4 V376M) advantageously has a favorable mutation that results in the enzyme having only about 50% of the nicotine demethylase activity of the wild-type CYP82E4 polypeptide. The variants set forth in SEQ ID NOs: 22 (CYP82E4 W329Stop), 23 (CYP82E4 K364N), 24 (CYP82E4 P381S), and 25 (CYP82E4 P458S) advantageously have favorable mutations that result in their nicotine demethylase activity being knocked out (i.e., 100% inhibition). Similarly, exemplary variants of the wild-type CYP82E4 include polypeptides comprising the sequence set forth in SEQ ID NO: 27, 28, 29, 30, 31, 32, 33, or 34. The variant set forth in SEQ ID NO:34 (CYP82E5 P449L) advantageously has a favorable mutation that results in inhibition of its nicotine demethylase activity, and the variant set forth in SEQ ID NO:33 advantageously has a favorable mutation that results in its nicotine demethylase activity being knocked out (i.e., 100% inhibition).

As used herein, a "variant polynucleotide" or "variant polypeptide" means a nucleic acid or amino acid sequence that is not wild-type.

A variant can have one addition, deletion or substitution; two or less additions, deletions or substitutions; three or less additions, deletions or substitutions; four or less additions, deletions or substitutions; or five or less additions, deletions or substitutions. A mutation includes additions, deletions, and substitutions. Such deletions or additions can be at the C-terminus, N-terminus or both the C- and N-termini. Fusion polypeptides or epitope-tagged polypeptides are also included in the present invention. "Silent" nucleotide mutations do not change the encoded amino acid at a given position. Amino acid substitutions can be conservative. A conservative substitution is a change in the amino acid where the change is to an amino acid within the same family of amino acids as the original amino acid. The family is defined by the side chain of the individual amino acids. A family of amino acids can have basic, acidic, uncharged polar or nonpolar side chains. See, Alberts et al., (1994) *Molecular biology of the cell* (3rd ed., pages 56-57, Garland Publishing Inc., New York, N.Y.), incorporated herein by reference as if set forth in its entirety. A deletion, substitution or addition can be to the amino acid of another CYP82E family member in that same position. As used herein, a "fragment" means a portion of a polynucleotide or a portion of a polypeptide and hence protein encoded thereby.

As used herein, "plant part" means plant cells, plant protoplasts, plant cell tissue cultures from which a whole plant can be regenerated, plant calli, plant clumps and plant cells that are intact in plants or parts of plants such as embryos, pollen, anthers, ovules, seeds, leaves, flowers, stems, branches, fruit, roots, root tips and the like. Progeny, variants and mutants of regenerated plants are also included within the scope of the present invention, provided that they comprise the introduced polynucleotides of the invention. As used herein, "tobacco plant material" means any portion of a plant part or any combination of plant parts.

DETAILED DESCRIPTION OF THE INVENTION

The present invention is directed to a novel nicotine demethylase gene, CYP82E10 (genomic sequence set forth in SEQ ID NO:4), and its encoded CYP82E10 nicotine demethylase (SEQ ID NO:2), that is involved in root-specific conversion of nicotine to nornicotine in roots of tobacco plants and its use in reducing or minimizing nicotine to nornicotine conversion and thus reducing levels of nornicotine in tobacco plants and plant parts thereof. By "root-specific" is intended it is preferentially expressed within the roots of tobacco plants, as opposed to other plant organs such as leaves or seeds. By introducing selected favorable mutations into this root-specific nicotine demethylase or variants thereof having nicotine demethylase activity, in combination with one or more selected favorable mutations within a gene encoding a green-leaf nicotine demethylase (for example, CYP82E5 set forth in SEQ ID NO:26) or variant thereof having nicotine demethylase activity, and further in combination with one or more selected favorable mutations within a gene encoding a senescence-induced nicotine demethylase (for example, CYP82E4 set forth in SEQ ID NO:14) or variant thereof having nicotine demethylase activity, it is possible to produce nontransgenic tobacco plants having minimal nicotine to nornicotine conversion, where the conversion rate is less than about 1.5%, preferably less than about 1%.

Lowering nornicotine levels in tobacco is highly desirable because this alkaloid serves as a precursor to the well-documented carcinogen N'-nitrosonornicotine (NNN). Two genes encoding proteins having nicotine demethylase activity in tobacco have been previously identified and designated as CYP82E4v2 and CYP82E5v2. The CYP82E4 polypeptide (SEQ ID NO:14) is a senescence-induced nicotine demethylase. The CYP82E4v2 gene (including the coding and intron regions), its role in nornicotine production in tobacco plants, and methods for inhibiting its expression and function are described in U.S. patent application Ser. No. 11/580,765, which published as U.S. Patent Application Publication No. 2008/0202541 A1. The CYP82E5 polypeptide (SEQ ID NO:26) is a green-leaf nicotine demethylase (i.e., its predominant expression is in green leaves). The CYP82E4 gene (including the coding and intron regions), its role in nornicotine production in tobacco plants, and methods for inhibiting its expression and function are described in U.S. patent application Ser. No. 12/269,531, which published as U.S. Patent Application Publication No. 2009/0205072 A1. The contents of these two U.S. patent applications and their respective publications are herein incorporated by reference in their entirety.

Plants homozygous for favorable mutant cyp82e4v2 and cyp82e5v2 alleles (i.e., mutant alleles that knock down, or knock out, expression of these respective nicotine demethylase genes), however, can still metabolize more than 2% of their nicotine to nornicotine, which represent nornicotine levels that can still lead to substantial NNN formation. The discovery of the CYP82E10 nicotine demethylase gene provides a further avenue for minimizing the nicotine to nornicotine conversion rate in tobacco plants, and thus further reducing the levels of nornicotine and thus NNN in tobacco plants and plant materials derived therefrom. Combining favorable mutant cyp82e10 alleles with favorable mutant cyp82e4v2 and cyp82e5v2 alleles provides for tobacco plants possessing more than a 3-fold reduction in nornicotine when compared to that observed for tobacco plants having the cyp82e4v2 mutation alone, or the cyp82e5v2 mutations together. In one embodiment, the present invention provides a homozygous triple mutant combination of nicotine demethylase genes cyp82e4v2, cyp82e5v2, and cyp82e10) that results in nontransgenic tobacco plants that produce very low levels of nornicotine comparable to that only previously achieved via transgenic gene suppression approaches, such as those described in U.S. Patent Application Publication Nos. 2008/0202541 A1 and 2009/0205072 A1.

Nicotine Demethylase Polynucleotides and Polypeptides, and Variants and Fragments Thereof Compositions of the present invention include the CYP82E10 polypeptide and variants and fragments thereof. Such nicotine demethylase polynucleotides and polypeptides are involved in the metabolic conversion of nicotine to nornicotine in plants, including commercial varieties of tobacco plants. In particular, compositions of the invention include isolated polypeptides comprising the amino acid sequences as shown in SEQ ID NOs:2, and 5-13, isolated polynucleotides comprising the nucleotide sequences as shown in SEQ ID NOs:1, 3, and 4, and isolated polynucleotides encoding the amino acid sequences of SEQ ID NOs:2 and 5-13. The polynucleotides of the present invention can find use in inhibiting expression of nicotine demethylase polypeptides or variants thereof that are involved in the metabolic conversion of nicotine to nornicotine in plants, particularly tobacco plants. Some of the polynucleotides of the invention have mutations which result in inhibiting the nicotine demethylase activity of the wild-type nicotine demethylase. The inhibition of polypeptides of the present invention is effective in lowering nornicotine levels in tobacco lines where genetic conversion occurs in less than 30%, 50%, 70%, 90% of the population, such as flue-cured tobaccos. The inhibition of polypeptides of the present invention is effective in lowering nornicotine levels in tobacco populations where genetic conversion occurs in at least 90%, 80%, 70%, 60%, 50% of a plant population. A population preferably contains greater than about 25, 50, 100, 500, 1,000, 5,000, or 25,000 plants where, more preferably at least about 10%, 25%, 50%, 75%, 95% or 100% of the plants comprise a polypeptide of the present invention.

The nicotine demethylase polynucleotides and encoded polypeptides of the present invention include a novel cytochrome P450 gene, designated the CYP82E10 nicotine demethylase gene, that is newly identified as having a role in the metabolic conversion of nicotine to nornicotine in roots of tobacco plants. Transgenic approaches such as sense, antisense, and RNAi suppression may be used to knock down expression of this nicotine demethylase, in a manner similar to that described for the CYP82E4 and CYP82E5 nicotine demethylases, as described in U.S. Patent Application Publication Nos. 2008/0202541 A1 and 2009/0205072 A1, the disclosures of which are herein incorporated by reference in their entirety. The preferred approach is one that introduces one or more favorable mutations into this gene, as this approach advantageously provides nontransgenic tobacco plants having reduced nicotine to nornicotine conversion rates, and thus reduced levels of nornicotine and NNN. Such approaches include, but are not limited to, mutagenesis, and the like, as described elsewhere herein below.

The invention encompasses isolated or substantially purified polynucleotide or protein compositions of the present invention. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30% 20%, 10%, 5%, or 1% (by dry weight) of chemical precursors or non-protein-of-interest chemicals.

Fragments of the disclosed polynucleotides and polypeptides encoded thereby are also encompassed by the present invention. Fragments of a polynucleotide may encode protein fragments that retain the biological activity of the native protein and hence are involved in the metabolic conversion of nicotine to nornicotine in a plant. Alternatively, fragments of a polynucleotide that are useful as hybridization probes or PCR primers generally do not encode fragment proteins retaining biological activity. Furthermore, fragments of the disclosed nucleotide sequences include those that can be assembled within recombinant constructs for use in gene silencing with any method known in the art, including, but not limited to, sense suppression/cosuppression, antisense suppression, double-stranded RNA (dsRNA) interference, hairpin RNA interference and intron-containing hairpin RNA interference, amplicon-mediated interference, ribozymes, and small interfering RNA or micro RNA, as described in the art and herein below. Thus, fragments of a nucleotide sequence may range from at least about 20 nucleotides, about 50 nucleotides, about 70 nucleotides, about 100 nucleotides about 150 nucleotides, about 200 nucleotides, 250 nucleotides, 300 nucleotides, and up to the full-length polynucleotide encoding the proteins of the invention, depending upon the desired outcome. In one aspect, the fragments of a nucleotide sequence can be a fragment between 100 and about 350 nucleotides, between 100 and about 325 nucleotides, between 100 and about 300 nucleotides, between about 125 and about 300 nucleotides, between about 125 and about 275 nucleotides in length, between about 200 to about 320 contiguous nucleotides, between about 200 and about 420 contiguous nucleotides in length between about 250 and about 450 contiguous nucleotides in length. Another embodiment includes a recombinant nucleic acid molecule having between about 300 and about 450 contiguous nucleotides in length.

A fragment of a nicotine demethylase polynucleotide of the present invention that encodes a biologically active portion of a CYP82E10 polypeptide of the present invention will encode at least 15, 25, 30, 50, 75, 100, 125, 150, 175, 200, 250, 300, 350, 400, 450, or 500 contiguous amino acids, or up to the total number of amino acids present in a full-length nicotine demethylase polypeptide of the invention (e.g., 517 amino acids for SEQ ID NOs:2 and 5-13). A biologically active portion of a nicotine demethylase polypeptide can be prepared by isolating a portion of one of the CYP82E10 polynucleotides of the present invention, expressing the encoded portion of the CYP82E10 polypeptide (e.g., by recombinant expression in vitro), and assessing the activity of the encoded portion of the CYP82E10 polypeptide, i.e., the ability to promote conversion of nicotine to nornicotine, using assays known in the art and those provided herein below.

Polynucleotides that are fragments of a CYP82E10 nucleotide sequence of the present invention comprise at least 16, 20, 50, 75, 100, 150, 200, 250, 300, 350, 400, 450, 500, 550, 600, 650, 700, 800, 900, 950, 1000, 1050, 1100, 1150, 1200, 1250, 1300, 1350, 1400, 1450, 1500, 1550, 1600, 1650, or 1700 contiguous nucleotides, or up to the number of nucleotides present in a full-length CYP82E10 polynucleotide as disclosed herein (e.g., 1551 for SEQ ID NO: 1; 2636 for SEQ ID NO:4). Polynucleotides that are fragments of a CYP82E10 nucleotide sequence of the present invention comprise fragments from about 20 to about 1700 contiguous nucleotides, from about 50 to about 1600 contiguous nucleotides, from about 75 to about 1500 contiguous nucleotides, from about 100 to about 1400 nucleotides, from about 150 to about 1300 contiguous nucleotides, from about 150 to about 1200 contiguous nucleotides, from about 175 to about 1100 contiguous nucleotides, about 200 to about 1000 contiguous nucleotides, about 225 to about 900 contiguous nucleotides, about 500 to about 1600 contiguous nucleotides, about 775 to about 1700 contiguous nucleotides, about 1000 to about 1700 contiguous nucleotides, or from about 300 to about 800 contiguous nucleotides from a CYP82E10 polynucleotide as disclosed herein. In one aspect, fragment polynucleotides comprise a polynucleotide sequence containing the polynucleotide sequence from the nucleotide at about position 700 to about position 1250 of a CYP82E10 coding sequence, at about position 700 to about position 1250 of a CYP82E10 genomic sequence, at about position 10 to about position 900 of a CYP82E10 intron sequence, or at about position 100 to about position 800 of a CYP82E10 intron sequence.

Variants of the disclosed polynucleotides and polypeptides encoded thereby are also encompassed by the present invention. Naturally occurring variants include those variants that share substantial sequence identity to the CYP82E10 polynucleotides and polypeptides disclosed herein as defined herein below. In another embodiment, naturally occurring variants also share substantial functional identity to the CYP82E10 polynucleotides disclosed herein. The compositions and methods of the invention can be used to target expression or function of any naturally occurring CYP82E10 that shares substantial sequence identity to the disclosed CYP82E10 polypeptides. Such CYP82E10 polypeptides can possess the relevant nicotine demethylase activity, i.e., involvement in the metabolic conversion of nicotine to nornicotine in plants, or not. Such variants may result from, for example, genetic polymorphism or from human manipulation as occurs with breeding and selection, including mutagenesis approaches. Biologically active variants of a CYP82E10 protein of the invention, for example, variants of the polypeptide set forth in SEQ ID NO:2 and 5-13, will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the wild-type protein as determined by sequence alignment programs and parameters described elsewhere herein, and can be characterized by their functional involvement in the metabolic conversion of nicotine to nornicotine in plants, or lack thereof. A biologically active variant of a protein of the invention may differ from that protein by as few as 1-15 amino acid residues, as few as 10, as few as 9, as few as 8, as few as 7, as few as 6, as few as 5, as few as 4, as few as 3, as few as 2, or as few as 1 amino acid residue. A biologically inactive variant of a protein of the invention may differ from that protein by as few as 1-15 amino acid residues, as few as 10, as few as 9, as few as 8, as few as 7, as few as 6, as few as 5, as few as 4, as few as 3, as few as 2, or as few as 1 amino acid residue.

Variants of a particular polynucleotide of the present invention include those naturally occurring polynucleotides that encode a CYP82E10 polypeptide that is involved in the metabolic conversion of nicotine to nornicotine in the roots of plants. Such polynucleotide variants can comprise a deletion and/or addition of one or more nucleotides at one or more sites within the native polynucleotide disclosed herein and/or a substitution of one or more nucleotides at one or more sites in the native polynucleotide. Because of the degeneracy of the genetic code, conservative variants for polynucleotides include those sequences that encode the amino acid sequence of one of the CYP82E10 polypeptides of the invention. Naturally occurring variants such as these can be identified with the use of well-known molecular biology techniques, as, for example, with polymerase chain reaction (PCR) and hybridization techniques as are known in the art and disclosed herein. Variant polynucleotides also include synthetically derived polynucleotides, such as those generated, for example, by using site-directed mutagenesis but which still share substantial sequence identity to the naturally occurring sequences disclosed herein, and thus can be used in the methods of the invention to inhibit the expression or function of a nicotine demethylase that is involved in the metabolic conversion of nicotine to nornicotine, including the nicotine demethylase polypeptides set forth in SEQ ID NOS:2, 5, 6, 7, 8, 9, and 10. Generally, variants of a particular polynucleotide of the invention, for example, the polynucleotide sequence of SEQ ID NO:3 or the polynucleotide sequence encoding the amino acid sequence set forth in SEQ ID NO:2, and 5-13, will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the present invention (also referred to as the reference polynucleotide) can also be evaluated by comparison of the percent sequence identity between the polypeptide encoded by the reference polynucleotide and the polypeptide encoded by a variant polynucleotide. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

Furthermore, the polynucleotides of the invention can be used to isolate corresponding root-specific nicotine demethylase sequences, particularly CYP82E10 sequences, from other members of the *Nicotiana* genus. PCR, hybridization, and other like methods can be used to identify such sequences based on their sequence homology to the sequences set forth herein. Sequences isolated based on their sequence identity to the nucleotide sequences set forth herein or to variants and fragments thereof are encompassed by the present invention. Such sequences include sequences that are orthologs of the disclosed sequences.

According to the present invention, "orthologs" are genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for a nicotine demethylase polypeptide that is involved in the nicotine-to-nornicotine metabolic conversion and which hybridize under stringent conditions to the CYP82E10 sequence disclosed herein, or to variants or fragments thereof, are encompassed by the present invention. Such sequences can be used in the methods of the present invention to inhibit expression of nicotine demethylase polypeptides that are involved in the metabolic conversion of nicotine to nornicotine in plants.

Using PCR, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed, Cold Spring Harbor Laboratory Press, Plainview, N.Y.). Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially mismatched primers, and the like.

Hybridization techniques involve the use of all or part of a known polynucleotide as a probe that selectively hybridizes to other corresponding polynucleotides present in a population of cloned genomic DNA fragments or cDNA fragments (i.e., genomic or cDNA libraries) from a chosen organism.

Hybridization may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In a specific embodiment, stringency conditions include hybridization in a solution containing 5×SSC, 0.5% SDS, 5×Denhardt's, 0.45 ug/ul Poly A RNA, 0.45 ug/ul calf thymus DNA and 50% formamide at 42° C., and at least one post-hybridization wash in a solution comprising from about 0.01× SSC to about 1×SSC. The duration of hybridization is from about 14 to about 16 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However; severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$ those of ordinary skill will understand that variations in the stringency of hybridization and/or wash solutions are inherently described. If the desired degree of mismatching results in a $T_m$, of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Hybridization probes may be genomic DNA fragments, cDNA fragments, RNA fragments, or other oligonucleotides, and may be labeled with a detectable group such as $^{32}P$, or any other delectable marker. For example, probes for hybridization can be made by labeling synthetic oligonucleotides based on the CYP82E10 polynucleotides sequences of the present invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the CYP82E10 polynucleotide sequences disclosed herein, or one or more portions thereof, may be used as probes capable of specifically hybridizing to corresponding root-specific nicotine demethylase polynucleotides and messenger RNAs. To achieve specific hybridization under a variety of conditions, such probes include sequences that are unique among the CYP82E10 polynucleotide sequences or unique to one of the CYP82E10 polynucleotide sequences, including upstream regions 5' to the coding sequence and downstream regions 3' to the coding sequence and an intron region (for example, SEQ ID NO:3), and are optimally at least about 10 contiguous nucleotides in length, more optimally at least about 20 contiguous nucleotides in length, more optimally at least about 50 contiguous nucleotides in length, more optimally at least about 75 contiguous nucleotides in length, and more optimally at least about 100 contiguous nucleotides in length. Such probes may be used to amplify corresponding CYP82E10 polynucleotides. This technique may be used to isolate additional coding sequences or mutations from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

As used herein, with respect to the sequence relationships between two or more polynucleotides or polypeptides, the term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, the term "comparison window" makes reference to a contiguous and specified segment of a polynucleotide sequence, where the polynucleotide sequence in the comparison window may comprise additions or deletions (i.e., gaps) compared to the deference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50. wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used (See www.ncbi.nlna.nih.gov). Alignment may also be performed manually by inspection.

In some embodiments, the sequence identity/similarity values provided herein are calculated using the BLASTX (Altschul et al. (1997) supra), Clustal W (Higgins et al. (1994) *Nucleic Acids Res.* 22:4673-4680), and GAP (University of Wisconsin Genetic Computing Group software package) algorithms using default parameters. The present invention also encompasses the use of any equivalent program thereof for the analysis and comparison of nucleic acid and protein sequences. By "equivalent program" is intended any sequence comparison program that, for any two sequences in question, generates an alignment having identical nucleotide or amino acid residue matches and an identical percent sequence identity when compared to the corresponding alignment generated by BLASTX. Clustal W, or GAP.

For purposes of the foregoing discussion of variant nucleotide and polypeptide sequences encompassed by the present invention, the term "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for malting this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

The term "percentage of sequence identity" as used herein means the value determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Thus, CYP82E10 polynucleotide and polypeptide sequences can be identified using the sequences provided herein. Such methods include obtaining a polynucleotide or polypeptide sequence at least 80%, 85%, 90%, 95%, 98%, 99% sequence identity with the polynucleotide sequence of SEQ ID NO: 1, 3, or 4 or a complement or fragment thereof, or a polypeptide sequence of SEQ ID NO: 2, or 5-13. A preferred embodiment includes a polypeptide corresponding to SEQ ID NO:2 that has a serine at position 79, 107, or 381 of the CYP82E10 polypeptide, where the numbering corresponds to SEQ ID NO:2.

Methods for Inhibiting Expression or Function of a Nicotine Demethylase

Methods of reducing the concentration, content, and/or activity of a CYP82E10 polypeptide of the present invention in a *Nicotiana* plant or plant part, particularly the root tissue, are provided. Many methods may be used, alone or in combination, to reduce or eliminate the activity of the CYP82E10 polypeptide of the present invention (SEQ ID NO:2), and variants thereof that retain nicotine demethylases activity (for example, SEQ ID NOs:7, 8, 9, and 10). In addition, combinations of methods may be employed to reduce or eliminate the activity of two or more different nicotine demethylases, more particularly the root-specific CYP82E10 nicotine demethylase and one or both of the green-leaf CYP82E5 and senescence-induced CYP82E4 nicotine demethylases. In a particular embodiment, the CYP82E5 is a polypeptide with at least one amino acid mutation in the sequence of SEQ ID NO: 26 that negatively affects conversion in green leaves and the CYP82E4 has the sequence set forth in SEQ ID NO:14 with at least one amino acid mutation that negatively affects conversion in senescent leaves.

In accordance with the present invention, the expression of a CYP82E10 nicotine demethylase of the present invention is inhibited if the protein level of the CYP82E10 polypeptide is statistically lower than the protein level of the same CYP82E10 polypeptide in a plant that has not been genetically modified or mutagenized to inhibit the expression of that CYP82E10 polypeptide, and where these plants have been cultured and harvested using the same protocols. In particular embodiments of the invention, the protein level of the CYP82E10 polypeptide in a modified plant according to the invention is less than 95%, less than 90%, less than 80%, less than 70%, less than 60%, less than 50%, less than 40%, less than 30%, less than 20%, less than 10%, or less than 5% of the protein level of the same CYP82E10 polypeptide in a plant that is not a mutant or that has not been genetically modified to inhibit the expression of that CYP82E10 polypeptide and which has been cultured and harvested using the same protocols. The expression level of the CYP82E10 polypeptide may be measured directly, for example, by assaying for the level of the CYP82E10 transcript or CYP82E10 polypeptide expressed in the tobacco plant or plant part, or indirectly, for example, by measuring the conversion of nicotine to nornicotine in the tobacco plant or plant part. Methods for monitoring the expression level of a protein are known in the art, and include, but are not limited to, Northern blot analysis and RNA differentiation assays. Methods for determining the activity of a targeted CYP82E10 polypeptide in converting nicotine to nornicotine are known in the art and described elsewhere herein below, and include, but are not limited to, alkaloid analysis using gas chromatography.

The present invention provides methods for reducing the level of nornicotine, or reducing the rate of conversion of nicotine to nornicotine, in a tobacco plant, or plant part thereof. The methods comprise introducing into the genome of a tobacco plant a mutation within at least one allele of each of at least three nicotine demethylase genes, wherein the mutation reduces expression of the nicotine demethylase gene, and wherein a first of these nicotine demethylase genes encodes a root-specific nicotine demethylase involved in the metabolic conversion of nicotine to nornicotine in a tobacco plant or a plant part thereof. In some embodiments, the root-specific nicotine demethylase is CYP82E10 or variant thereof. In other embodiments, these methods comprise introducing into the genome of a tobacco plant a mutation within at least one allele of a nicotine demethylase gene encoding CYP82E10 or variant thereof, and a mutation within at least one allele of a nicotine demethylase encoding CYP82E4 or variant thereof, and/or a nicotine demetyylase encoding CYP82E5 or variant thereof.

A number of approaches have been used to combine mutations in one plant including sexual crossing. A plant having a favorable mutation in a CYP82E10 gene that inhibits the nicotine demethylases activity in roots can be crossed with a plant having a favorable mutation in a CYP82E4v2 gene that inhibits the nicotine demethylase activity in senescent leaves, or be crossed with a plant having a favorable mutation in a CYP83E5v2 gene that inhibits nicotine demethylase activity in green leaves to produce a plant having reduced nicotine to nornicotine conversion. In preferred embodiments, crosses are made in order to introduce a favorable mutation within a CYP82E10, CYP82E4v2, and CYP82E5v2 gene within the same plant. In this manner, a plant having a favorable mutation in a CYP82E10 gene that inhibits the nicotine demethylases activity in roots is crossed with a plant having a favorable mutation in a CYP82E4v2 gene that inhibits the nicotine demethylase activity in senescent leaves and a favorable mutation in a CYP83E5v2 gene that inhibits nicotine demethylase activity in green leaves. Alternatively, a plant having a favorable mutation in a CYP82E4v2 gene that inhibits the nicotine demethylase activity in senescent leaves is crossed with a plant having a favorable mutation in a CYP82E10 gene that inhibits the nicotine demethylase activity in roots and a favorable mutation in a CYP83E5v2 gene that inhibits nicotine demethylase activity in green leaves. In yet another embodiment, a plant having a favorable mutation in a CYP82E5v2 gene that inhibits the nicotine demethylase activity in green leaves is crossed with a plant having a favorable mutation in a CYP82E10 gene that inhibits the nicotine demethylase activity in roots and a favorable mutation in a CYP83E4v2 gene that inhibits nicotine demethylase activity in senescent leaves. By introducing a favorable mutation into each of these nicotine demethylases genes it is possible to produce a plant having reduced nicotine to nornicotine conversion rates with conversion levels lower than about 0.2%, 0.3%, 0.4%, 0.5%, 0.6%, or 0.7%.

In a more preferred embodiment, a plant having one or more favorable mutations that results in a modification of the CYP82E10 polypeptide at position 79, 107, 381, or 419 (where the numbering is according to SEQ ID NO:2) can be crossed with a plant having one or more favorable mutations that results in a modification of the CYP82E4 polypeptide at position 329, 364, 376, 381, or 458 and/or having one or more favorable mutations that results in a modification of the CYP82E5 polypeptide at position 422 or 449 to produce a plant with conversion levels lower than 0.2%, 0.3%, 0.4%, 0.5%, 0.6%, or 0.7%. A particularly preferred conversion level of nicotine to nornicotine can be between 0.05%-0.4%, between 0.1-0.6%, between 0.1%-0.3%, between 0.1%-0.5%, between 0.1%-0.4%, between 0.1%-0.7%, between 0.1%-1.0%, between 0.1%-1.1%, between 0.1%-1.2%, between 0.1%-1.3%, between 0.1%-1.4%, or between 0.1%-1.5%. Any mutation of a polynucleotide of the present invention that results in a truncation of the CYP82E10, CYP83E4, or CYP83E5 polypeptide before a conserved heme-binding motif will inhibit the enzyme and can be used in a cross described above. The domains of cytochrome P450 proteins are known in the art. See, for example, Xu et al. (2007) *Physiologia Plantarum* 129:307-319, hereby incorporated by reference. By crossing plants having a nonfunctional or inhibited CYP82E10 gene with plants having a nonfunctional or inhibited CYP82E4v2 gene, a nonfunctional or inhibited CYP82E5v2 gene, or nonfunctional or inhibited CYP82E4v2 and CYP82E5v2 genes, nornicotine levels can be reduced in a tobacco plant.

The activity of a CYP82E10, CYP82E4, or CYP82E5 nicotine demethylase polypeptide in converting nicotine to nornicotine in a tobacco plant or plant part is inhibited according to the present invention if this conversion activity is statistically lower than conversion activity of the same nicotine demethylase polypeptide in a tobacco plant or plant part that has not been genetically modified to inhibit the conversion activity of that nicotine demethylase polypeptide and which has been cultured and harvested using the same protocols. In particular embodiments, activity of a nicotine demethylase polypeptide in converting nicotine to nornicotine in a modified tobacco plant or plant part according to the invention is inhibited if the activity is less than 95%, less than 90%, less than 80% less than 70%, less than 60%, less than 50%, less than 40%, less than 30%, less than 20% less than 10%, less than 5%, less than 2%, or less than 1% of the conversion activity of the same nicotine demethylase polypeptide in a tobacco plant that has not been genetically modified to inhibit the expression of that nicotine demethylase polypeptide and has been cultured and harvested using the same protocols. The activity of a nicotine demethylase polypeptide in converting nicotine to nornicotine in a tobacco plant or plant part is eliminated according to the invention when it is not detectable by the assay methods described elsewhere herein. Methods of determining the activity of a nicotine demethylase polypeptide in converting nicotine to nornicotine in a tobacco plant using gas chromatography are disclosed in the examples here in below.

In some embodiments, the favorable mutation is introduced into a tobacco plant or plant part using a mutagenesis approach, and the introduced mutation is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

A modified tobacco plant containing a favorable mutation in a nicotine demethylase described herein has a reduced level of conversion of nicotine to nornicotine. In particular embodiments, conversion of nicotine to nornicotine in a modified tobacco plant or plant part according to the invention is less than 95%, less than 90%, less than 80% less than 70%, less than 60%, less than 50%, less than 40%, less than 30%, less than 20% less than 10%, less than 5%, less than 2%, or less than 1% of the conversion in a tobacco plant that that has not been genetically modified to inhibit the expression of that nicotine demethylase polypeptide and which has been cultured and harvested using the same protocols. In some embodiments, the modified tobacco plant is a converter tobacco plant. In other embodiments, the modified tobacco plant is a nonconverter tobacco plant. In some embodiments, the modified tobacco plant has a conversion rate lower than the rate observed in commercial non-converter tobacco plants.

According to the present invention, changes in levels, ratios, activity, or distribution of CYP82E10 polypeptides of the present invention, or changes in tobacco plant or plant part phenotype, particularly reduced accumulation of nornicotine and its carcinogenic metabolite, NNN, could be measured by comparing a subject plant or plant part to a control plant or plant part, where the subject plant or plant part and the control plant or plant part have been cultured and/or harvested using the same protocols. As used herein, a subject plant or plant part is one in which genetic alteration, for example, by mutagenesis, has been affected as to the nicotine demethylase polypeptide of interest, or is a tobacco plant or plant part that is descended from a tobacco plant or plant part so altered and which comprises the alteration. A control plant or plant part provides a reference point for measuring changes in phenotype of the subject plant or plant part. The measurement of changes in phenotype can be measured at any time in a plant or plant part, including during plant development, senescence, or after curing. In other embodiments, the measurement of changes in phenotype can be measured in plants grown under any conditions, including from plants grown in growth chamber, greenhouse, or in a field. In one embodiment, changes in phenotype can be measured by determining the nicotine to nornicotine conversion rate. In a preferred embodiment, conversion can be measured by dividing the percentage of nornicotine (as a percentage of the total tissue weight) by the sum of the percentage nicotine and nornicotine (as percentages of the total tissue weight) and multiplying by 100.

According to the present invention, a control plant or plant part may comprise a wild-type tobacco plant or plant part, i.e., of the same genotype as the starting material for the genetic alteration that resulted in the subject plant or plant part. A control plant or plant part may also comprise a tobacco plant or plant part of the same genotype as the starting material but that has been transformed with a null construct (i.e., with a construct that has no known effect on the trait of interest, such as a construct comprising a selectable marker gene). In all such cases, the subject plant or plant part and the control plant or plant part are cultured and harvested using the same protocols.

In some embodiments, the activity of a nicotine demethylase polypeptide of the present invention may be reduced or eliminated by disrupting the gene encoding the nicotine demethylase polypeptide. The invention encompasses mutagenized plants that carry mutations in nicotine demethylase genes, where the mutations reduce expression of the nicotine demethylase gene or inhibit the activity of an encoded nicotine demethylase polypeptide of the present invention.

In other embodiments, the activity of a nicotine demethylase polypeptide of the present invention is reduced or eliminated by disrupting the gene encoding the nicotine demethylase polypeptide. The gene encoding the nicotine demethylase polypeptide may be disrupted by any method known in the art, for example, by transposon tagging or by mutagenizing plants using random or targeted mutagenesis and selecting for plants that have reduced nicotine demethylase activity or mutations in CYP82E10, alone or in combination with mutations in CYP82E4 or CYP82E5.

Transposon tagging may be used to reduce or eliminate the activity of one or more CYP82E10 nicotine demethylase polypeptides of the present invention. Transposon tagging comprises inserting a transposon within an endogenous nicotine demethylase gene to reduce or eliminate expression of the nicotine demethylase polypeptide.

Methods for the transposon tagging of specific genes in plants are well known in the art. See, for example, Maes et al. (1999) *Trends Plant Sci.* 4:90-96; Dharmapuri and Sonti (1999) *FEMS Micerobiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-9b; Fitzmaurice et al. (1999) *Genetics* 153:1919-1928).

Additional methods for decreasing or eliminating the expression of endogenous genes in plants are also known in the art and can be similarly applied to the instant invention. These methods include other forms of mutagenesis, using mutagenic or carcinogenic compounds including ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima et al. (1998) *Virology* 213:472-481; Okubara et al. (1994) *Genetics* 137:867-874; and Quesada et al. (2000) *Genetics* 154:421-4315; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See McCallum et al (2000) *Nat. Biotechnol.* 18:455-457, herein incorporated by reference.

Mutations that impact gene expression or that interfere with the function of the encoded nicotine demethylase protein can be determined using methods that are well known in the art. Insertional mutations in gene exons usually result in null-mutants. Mutations in conserved residues can be particularly effective in inhibiting the metabolic function of the encoded protein. Conserved residues of plant nicotine demethylase polypeptides suitable for mutagenesis with the goal to eliminate activity of a nicotine demethylase polypeptide in converting nicotine to nornicotine in a tobacco plant or plant part have been described. See FIG. 1A-C of U.S. Patent Application Publication No. 2009/0205072 A1, herein incorporated by reference in its entirety, where the residues that differ from the other P450 polypeptides are shaded in grey. The conserved residue is that which is not shaded in grey at each position. Such mutants can be isolated according to well-known procedures.

In another embodiment of this invention, dominant mutants can be used to trigger RNA silencing due to gene inversion and recombination of a duplicated gene locus. See, for example, Kusaba et al. (2003) *Plant Cell* 15:1455-1467.

In another embodiment of the invention, the compositions of the invention find use in screening methods to identify nonconverter plants for use in breeding programs. In this manner, the nucleotide sequences of the invention can be used to screen native germplasms for nonconverter plants having a stable mutation in the CYP82E10 gene identified herein. These nonconverter plants identified by the methods of the invention can be used to develop breeding lines.

In addition to the nucleotide sequences encoding the CYP82E10 polypeptides described herein, compositions of the invention include an intron sequence in the CYP82E10 gene sequence that can be used in screening methods. While not bound by any mechanism of action, the CYP82E10 gene(s) may represent the only member(s) of the cytochrome P450 family involved in the metabolic conversion of nicotine to nornicotine in roots of tobacco. For certain applications it would be useful to have a means of diagnostically differentiating this specific member of the cytochrome P450 gene family from the rest of the closely related sequences within this family. For example, it is possible that within the naturally existing tobacco germplasm (or in mutagenized populations), accessions may exist in which this gene is naturally dysfunctional and may therefore may be valuable as a permanently nonconverter resource. Such dysfunctional sequences may include those encoding the polypeptides set forth in SEQ ID NO: 11, 12, or 13. A method to specifically assay for such genotypes (e.g. deletion mutants, rearrangements, and the like) could serve as a powerful tool. The present invention includes primers designed to specifically amplify exon 1 and exon 2 of CYP82E10 where one of the two primer pairs corresponds to the intron between the exons. Examples of primers useful to amplify the exons of CYP82E10 include SEQ ID NO: 35 with SEQ ID NO: 36 and SEQ ID NO: 37 with SEQ ID NO: 38. These same primers can be used for sequence analysis of the products.

Because the intron regions of genes are typically less conserved than exons, it is predicted that the use of an intron-specific probe would better enable one to distinguish the gene(s) corresponding to the CYP82E10 gene from the other members of the CYP82E family. The use of a CYP82E10 intron-specific probe, and/or the PCR primers used to generate products provide powerful tools in assays to determine whether any naturally occurring, or mutagenized, tobacco plants possess deletions or rearrangements that may render the gene inactive. Such a plant can then be used in breeding programs to create tobacco lines that are incapable of converting.

Tobacco Plants, Plant Parts, and Products Having Reduced Nornicotine and NNN Content The CYP82E10 polynucleotides of the invention, and variants and fragments thereof, can be used in the methods of the present invention to inhibit expression or function of CYP82E10 nicotine demethylases that are involved in the metabolic conversion of nicotine to nornicotine in a plant. In this manner, favorable mutations can be introduced into the CYP82E10 gene of interest. The methods of the invention do not depend on a particular method for introducing the favorable mutation into the CYP82E10 nicotine demethylase gene.

The compositions and methods of the invention can be used to reduce the nornicotine content, particularly in the leaves and stems, of any plant of the genus *Nicotiana* including, but not limited to, the following species: *acuminata, affinis, alata, attenuate, bigelovii, clevelandii, excelsior, forgetiana, glauca, glutinosa, langsdorffii, longiflora, obtusifolia, palmeri, paniculata, plumbaginifolia, qudrivalvis, repanda, rustica, suaveolens, sylvestris, tabacum, tomentosa, trigonophylla,* and x *sanderae.* The present invention can also be practiced using any varieties of a plant of the genus *Nicotiana,* including but not limited to *Nicotiana acuminata multiflora, Nicotiana alata grandiflora, Nicotiana bigelovii quadrivalvis, Nicotiana bigelovii wallacei, Nicotiana obtusifolia obtusifolia, Nicotiana obtusifolia plameri, Nicotiana quadrivalvis bigelovii, Nicotiana quadrivalvis quadrivalvis, Nicotiana quadrivalvis wallacei,* and *Nicotiana trigonophylla palmeri,* as well as varieties commonly known as flue or bright varieties, Burley varieties, dark varieties and oriental/Turkish varieties. In some embodiments, the tobacco plant of interest is a Burley, Virginia, flue-cured, air-cured, fire-cured, Oriental, or a dark tobacco plant.

The tobacco plants and varieties described herein are suitable for conventional growing and harvesting techniques, such as cultivation in manure rich soil or without manure, bagging the flowers or no bagging, or topping or no topping. The harvested leaves and stems may be used in any traditional tobacco product including, but not limited to, pipe, cigar and cigarette tobacco, and chewing tobacco in any form including leaf tobacco, shredded tobacco, or cut tobacco.

Thus the present invention provides a tobacco plant, or plant part thereof, comprising a mutation in a gene encoding a CYP82E10 nicotine demethylase, wherein said mutation results in reduced expression or function of said CYP82E10 nicotine demethylases, and a reduced amount of nornicotine and N'-nitrosonornicotine. As used herein, the term "a reduced amount" or "a reduced level" is intended to refer to an amount of nornicotine and/or N'-nitrosonornicotine in a plant of the present invention or a plant part or tobacco product thereof that is less than what would be found in a plant of the genus *Nicotiana* or a plant part or tobacco product from the same variety of tobacco, processed (i.e., cultured and harvested) in the same manner, that has not been genetically modified for reduced nornicotine and/or N'-nitrosonornicotine. The amount of nornicotine may be reduced by about 10% to greater than about 90%, including greater than about 20%, about 30%, about 40%, about 50%, about 60%, about 70%, and about 80%. The conversion of nicotine to nornicotine can be less than 0.3%, less than 0.5%, less than 0.7%, between 0.1%-0.5%, between 0.1%-0.4%, between 0.1%-0.7%, or between 0.1%-1.0% in plants, plant parts, and products of the present invention, and more specifically in plants, plant parts having mutations in CYP82E10, CYP82E4v2, and CYP825v2.

The term "tobacco products" as used herein include, but are not limited to, smoking materials (e.g., any cigarette, including a cigarillo, a non-ventilated or vented recess filter cigarette, a cigar, pipe tobacco), smokeless products (e.g., snuff, chewing tobacco, biodegradable inserts (e.g., gum, lozenges, dissolving strips)). See, for example, U.S. Patent 2005/0019448, herein incorporated by reference. The present invention also encompasses a range of tobacco product blends that can be made by combining conventional tobacco with differing amounts of the low nornicotine and/or N'-nitrosonornicotine tobacco described herein. In further embodiments, the plant or plant part of the genus *Nicotiana* as described above is cured tobacco.

In some embodiments of the present invention, the tobacco product reduces the carcinogenic potential of tobacco smoke that is inhaled directly with consumption of a tobacco product such as cigars, cigarettes, or pipe tobacco, or inhaled as secondary smoke (i.e., by an individual that inhales the tobacco smoke generated by an individual consuming a tobacco product such as cigars, cigarettes, or pipe tobacco). The cured tobacco described herein can be used to prepare a tobacco product, particularly one that undergoes chemical changes due to heat, comprising a reduced amount of nornicotine and/or N'-nitrosonornicotine in the smoke stream that is inhaled directly or inhaled as secondary smoke. In the same manner, the tobacco products of the invention may be useful in the preparation of smokeless tobacco products such as chewing tobacco, snuff and the like.

The tobacco products derived from the tobacco plants of the present invention thus find use in methods for reducing the carcinogenic potential of these tobacco products, and reducing the exposure of humans to the carcinogenic nitrosamine NNN, particularly for individuals that are users of these tobacco products. The following examples are offered by way of illustration and not by way of limitation.

EXPERIMENTAL

The citations mentioned in the following discussion are provided at the close of the Experimental section.

Background

The knowledge that CYP82E4v2 represents the nicotine demethylase locus responsible for the high nornicotine accumulation observed in Converter plants (Siminszky et al., 2005), opened the door for nontransgenic, as well as transgenic, approaches toward overcoming the conversion problem and lowering the nornicotine content of the senescent, cured leaf. Specifically, it became possible for researchers to generate tobacco populations that had been exposed to a chemical mutagen, and select for individuals possessing nonfunctional alleles at the CYP82E4v2 locus. In fact, three independent groups have already generated nonconverting tobacco lines based on this strategy (Dewey et al., 2007; Xu et al., 2007b; Julio et al., 2008).

As previously reported, a tobacco plant designated 775 was identified from an EMS-mutagenized population of Burley line DH98-325-6 and shown to possess a knockout mutation within the CYP82E4v2 gene (Dewey et al., 2007). In the summer of 2008, plants homozygous for the 775 mutation were grown at the Upper Coastal Plains research station in Rocky Mount, N.C., and air-cured according to standard industry practice. Alkaloid analysis of these materials was conducted using the "LC Protocol" described by Jack et al. (2007). As shown in Table 1, plants possessing the 775 mutation averaged 2.6% nicotine to nornicotine conversion, In contrast, >60% conversion was observed in the parental line DH98-325-6, a strong converter genotype. Nearly identical results were reported by Julio et al. (2008), who recorded conversion percentages ranging from 2.82 to 3.37 for plants homozygous for a cyp82e4v2 knockout mutant within the strong converter burley genotype BB16NN (parental conversion rates ranged between 68-98%). Thus, debilitating mutations in CYP82E4v2 alone appear to be effective in eliminating the problems arising from the unstable genetic phenomenon associated with the generation of Converter plants.

TABLE 1

Alkaloid profiles for experimental materials evaluated in 2008 field experiment. Percentage values represent an average.

| Genotype | Gene Targeted | Mutation[b] | Amino Acid Change | % Nicotine[c] | % Nornicotine | % Anabasine | % Anatabine | % Conversion[d] |
|---|---|---|---|---|---|---|---|---|
| DH98-325-6 control (15)[a] | Control | — | — | 1.228 | 2.014 | 0.016 | 0.125 | 62.4 |
| TN90LC (14) | Control | — | — | 4.680 | 0.157 | 0.022 | 0.155 | 3.2 |
| DH98-325-6 RNAi 300-08 #1 (15) | CYP82E4v2 and related | — | — | 3.351 | 0.040 | 0.016 | 0.101 | 1.2 |
| DH98-325-6 RNAi 300-02 #1 (15) | CYP82E4v2 and related | — | — | 3.741 | 0.026 | 0.017 | 0.106 | 0.7 |
| DH98-325-6 #775 Homo. (15) | CYP82E4v2 | G986A | W329Stop | 2.941 | 0.077 | 0.013 | 0.093 | 2.6 |

TABLE 1-continued

Alkaloid profiles for experimental materials evaluated in 2008 field experiment. Percentage values represent an average.

| Genotype | Gene Targeted | Mutation[b] | Amino Acid Change | % Nicotine[c] | % Nornicotine | % Anabasine | % Anatabine | % Conversion[d] |
|---|---|---|---|---|---|---|---|---|
| DH98-325-6 #1013 Homo. (14) | CYP82E5v2 | G1266A | W422Stop | 1.005 | 1.876 | 0.012 | 0.097 | 65.2 |
| DH98-325-6 Double Homozygous Mutant (9) | | Double | Double | 3.160 | 0.076 | 0.015 | 0.117 | 2.3 |

[a]Number in parentheses indicates total number of plants analyzed.
[b]Numbering relative to start codon of cDNA sequence.
[c]Percentages were calculated on a dry tobacco weight basis.
[d]Percentage nicotine conversion equals [% nornicotine/(% nornicotine + % nicotine)] × 100.

Although the utilization of tobacco plants possessing the 775, or comparable, mutations in CYP82E4v2 can be an effective means of eliminating the introduction of Converter plants within tobacco populations, a low, but significant amount of nornicotine remains in these plants. Given that nicotine to nornicotine conversion rates as low as 0.45% were observed in transgenic plants expressing an RNAi-based construct directed against CYP82E4v2 (Lewis et al., 2008), it was apparent that at least one other gene with high DNA sequence homology to CYP82E4v2 must be responsible for the majority of the nornicotine synthesis that is observed within both Nonconverter plants and Converter plants possessing an inactivated CYP82E4v2 gene. This possibility was further supported by the discovery of CYP82E5v2, a gene that shares 92.7% DNA sequence identity with CYP82E4v2 that was also shown to encode a functional nicotine demethylase enzyme (Dewey et al., 2007; Gavilano and Siminszky, 2007). The CYP82E5v2 nicotine demethylase gene is expressed at low levels in green tobacco leaves of Converter and Nonconverter plants alike, in contrast to CYP82E4v2 which is expressed at very high levels, but only in the leaves of Converter plants during senescence and air-curing.

As outlined in Dewey et al. (2007), screening of an EMS-mutagenized DH98-325-6 tobacco population lead to the identification of an individual (plant 1013) possessing a knockout mutation in CYP82E5v2. To determine the impact of the non-functional cyp82e5v2 allele on nornicotine accumulation, crosses were made that combined the mutations from plants 775 and 1013. Molecular genotyping of numerous $F_2$ individuals derived from the $F_1$ progeny of the initial cross resulted in the identification of nine individuals that were homozygous for both mutations (e4e4/e5e5). These nine plants were also included in the 2008 field trial. Despite the fact the CYP82E5v2 has been shown to encode a functional nicotine demethylase enzyme (Dewey et al., 2007; Gavilano and Siminszky, 2007), combining the dysfunctional cyp82e5v2 mutation with the knockout cyp82e4v2 mutation had remarkably little impact on leaf nornicotine levels. As shown in Table 1, plants homozygous for the double mutation (e4e4/e5e5) averaged 2.3% nicotine conversion, compared with an average of 2.6% conversion for plants possessing only the cyp82e4v2 mutation (e4e4). The modest difference in mean conversion between the two genotypes was not statistically significant (P=0.118). In contrast, one of the CYP82E4v2 RNAi-silenced transgenic lines that was included in this study averaged 0.7% conversion, an amount significantly lower (P<0.001) than that obtained from either the e4e4 or e4e4/e5e5 genotypes. Thus, another gene with high homology to CYP82E4v2 must exist within the tobacco genome that contributes toward nornicotine production in the plant.

EXAMPLE 1

Isolation and Characterization of the cyp82e10 Nicotine Demethylase Gene

To identify other genes in the tobacco genome that have the potential of encoding nicotine demethylase enzymes, homology searches using the BLASTN and BLASTX algorithms (Altschul et al., 1990, 1997) were directed against the N. tabacum expressed sequenced tagged (EST) databases in GenBank, using the DNA and protein sequences of CYP82E4v2 as the respective query sequences. In addition to identifying cDNA sequences corresponding to previously characterized members of the CYP82E superfamily (such as CYP82E2, CYP82E3 and CYP82E5v2), seven ESTs were discovered that did not align perfectly with any previously characterized member of this gene family. Interestingly, all seven of the ESTs originated from either root-specific cDNA libraries, or cDNA libraries made up of mixed tissues that included roots. This observation suggested that the new CYP82E gene is expressed specifically in root tissue, a property that could explain why this particular member of the CYP82E P450 superfamily has eluded detection previously, as prior efforts have focused on the characterization of CYP82E genes expressed in leaf tissue. Because no individual EST sequence was long enough to cover the entire coding region of this novel gene, PCR primers were designed that enabled amplification of the entire cDNA sequence from first-strand cDNA that had been generated from RNA isolated from tobacco root tissue. In addition, primers were used to amplify the corresponding genomic region of the gene that includes a central, large intron. This novel CYP82E cDNA shares 92.4% nucleotide identity with the tobacco CYP82E4v2 cDNA, and a 91.1% predicted identity at the amino acid level. In keeping with the guidelines for P450 gene nomenclature, this new gene was designated CYP82E10. Of all the characterized members of the CYP82E superfamily, CYP82E10 displays that highest sequence similarity with CYP82E5v2, sharing 96.5% nucleotide identity at the cDNA level and 95.7% predicted amino acid sequence identity. The DNA sequence of CYP82E10 and its predicted protein sequence are shown in FIG. 1.

Figure 2B:
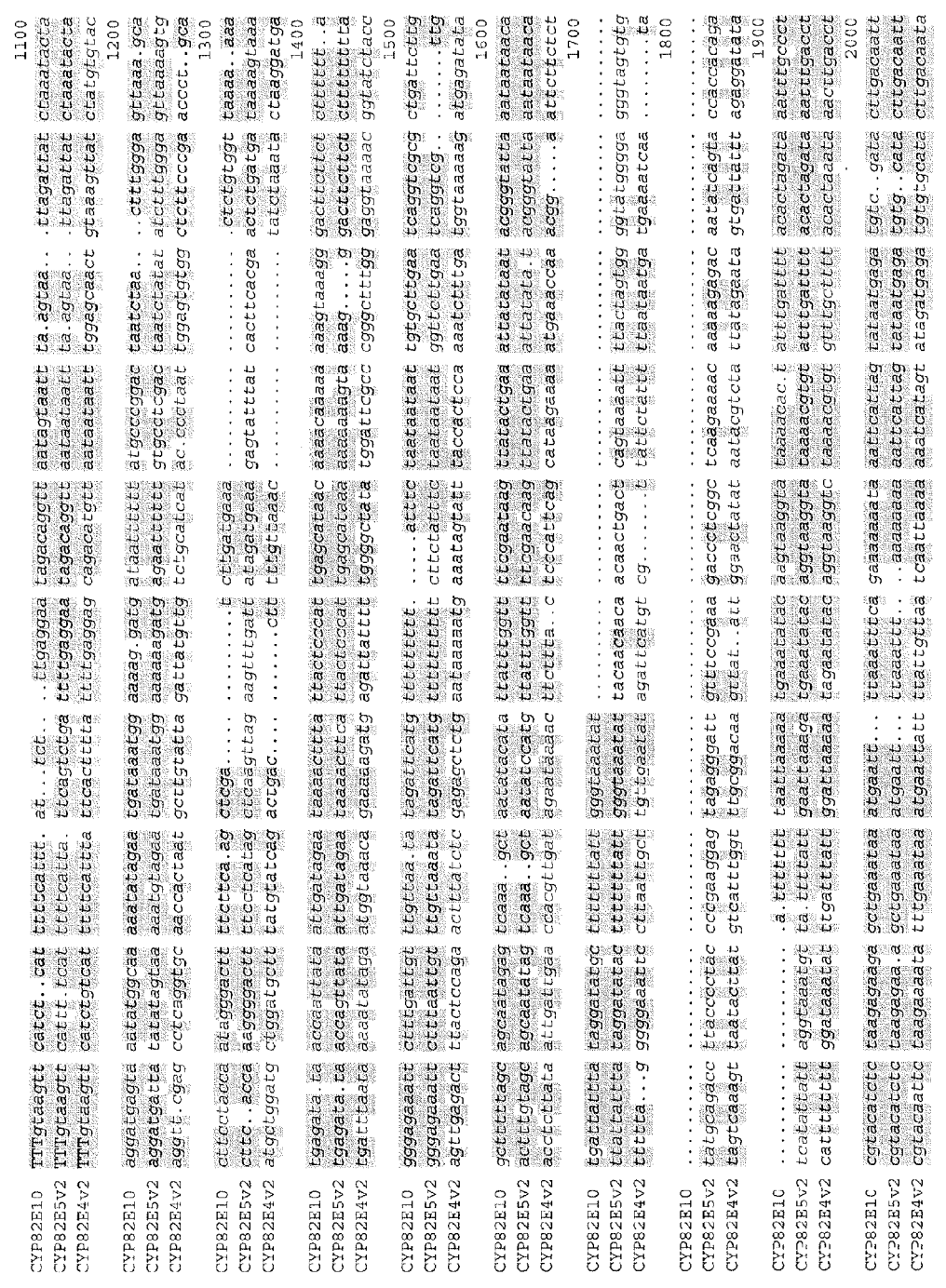

Although the cDNAs of the various CYP82E family members tend to be highly conserved, the genomic versions of these genes show much greater sequence diversity. This is due primarily to the substantial sequence divergence observed within the large, central intron. An alignment of CYP82E4v2, CYP82E5v2, and CYP82E10 genomic sequences is shown in FIG. 2. As calculated using the EMBOSS Pairwise Alignment algorithm (www.ebi.ac.uk/Tools/emboss/align/index.html), the CYP82E4v2 and CYP82E10 genes share 78.3% nucleotide identity, and CYP82E10 is 84.9% identical to the CYP82E5v2 gene as they exist within the tobacco genome (CYP82E4v2 and CYP82E5v2 genomic sequences share 75% identity).

As detailed in several publications, most of the genes of the CYP82E superfamily that are found in the tobacco genome do not encode functional nicotine demethylase enzymes (Siminszky et al., 2005; Chakrabarti et al., 2007; Dewey et al., 2007; Gavilano et al., 2007; Xu et al., 2007a). Therefore, sequence homology alone is not a very accurate indicator of gene function for the CYP82E family. Instead, expression analysis in either transgenic plants (Siminszky et al., 2005) or in yeast (Gavilano and Siminszky, 2007; Xu et al., 2007a) has become the established means for determining whether individual members of this gene family encode nicotine demethylase activity.

To determine whether CYP82E10 functions as a nicotine demethylase gene, its cDNA was cloned into the yeast expression vector pYeDP60 and transformed into yeast strain W(R). Strain W(R) is a yeast cell line that was engineered to overexpress the yeast NADPH-dependent P450 reductase, an enzyme that serves as the direct electron donor to P450s; this system greatly enhances the detection of foreign P450 enzyme activities that are expressed in yeast (Pompon et al., 1995). Nicotine demethylase assays were conducted by incubating yeast microsomal membrane preparations with [$^{14}$C]-nicotine, and resolving the products by thin layer chromatography as described in Siminszky et al. (2005).

As shown in FIG. 3, no nicotine demethylase activity could be detected using yeast microsomes from the W(R) strain expressing only the pYeDP60 vector. In contrast, a very robust nicotine demethylase activity could be measures from microsomes derived from yeast cells expressing the CYP82E10 cDNA. By measuring CYP82E10 enzyme activity across a wide range of [$^{14}$C]-nicotine concentrations, a substrate saturation curve was established and an apparent $K_m$ of 3.9 µM nicotine was calculated using the microsomal assay. This kinetic parameter for CYP82E10 is very similar to the $K_m$s reported for the CYP82E4v2 and CYP82E5v2 enzymes when similarly expressed in yeast (Gavilano et al., 2007; Gavilano and Siminszky, 2007; Xu et al., 2007a).

EXAMPLE 2

Identification of Plants Possessing Mutant Alleles of CYP82E10

In order to accurately assess the specific contribution of CYP82E10 toward the total nornicotine content of the tobacco plant, it was necessary to: (1) identify a tobacco plant with a knockout mutation within this gene; and (2) combine this mutation with the cyp82e4v2 and cyp82e5v2 mutations originating from plants 775 and 1013, respectively. To identify potentially debilitating mutations in CYP82E10, the EMS-mutagenized DH98-325-6 population was screened by high-throughput DNA sequence analysis using primers that specifically amplify portions of CYP82E10 (without simultaneously amplifying other members of the CYP82E superfamily). To specifically amplify exon 1 of CYP82E10, the following PCR primers were used: 5'-GTGATAGTTTGAT-TCCCAAGTGC-3' (forward) and 5'-CTCCCAAAGTTA-GATTAGTCCG-3' (reverse); specific amplification of exon 2 was achieved using the primers 5'-AGGTCGCGCTGAT-TCTTG-3' (forward) and 5'-AGATGAATACCCATC-TATCTAGGAGT-3' (reverse). To ensure maximal specificity, the reverse primer for exon 1 and the forward primer for exon 2 correspond to sequences within the CYP82E10 intron (FIG. 1). PCR amplification and sequence analysis of the mutagenized plants was conducted using a 96-well format as described in Dewey et al. (2007).

High-throughput sequence analysis of over 1,200 individuals from the mutagenized tobacco population resulted in the identification of 15 individuals with mutations in CYP82E10. The most notable of these are shown in Table 2. The nucleotide and amino acid residues mutated in these plants are also highlighted in FIG. 1. Although no truncation mutations were observed among these individuals, in several cases, mutations were identified that altered an amino acid residue within a highly conserved region of the enzyme. To determine the effects of a particular mutation on CYP82E10 enzyme activity, site-directed mutagenesis was used to introduce the specific mutations corresponding to seven of the nine mutations shown in Table 2 into the CYP82E10 cDNA within the pYeDP60 yeast expression vector. Microsomal preparations from yeast strains expressing each of the seven CYP82E10 variants were assayed in vitro for nicotine demethylase activity using both non-saturating (2.45 µM) and saturating (50 µM) concentrations of [$^{14}$C]-nicotine. The results from the yeast expression assays showed that mutations found plants 693, 817 and 1035 did not alter enzyme activity, whereas the mutations found in plants 1041, 1512 and 2476 lead to complete enzyme inactivation. The mutation observed in plant 1442 resulted in a 75% reduction in activity compared to the wild type CYP82E10 enzyme.

The thin layer chromatographic data for the in vitro yeast expression assays corresponding to the plant 1041 mutation are shown in FIG. 3. This particular mutation was selected for more extensive investigation. To provide additional confirmation that the Pro to Ser substitution at amino acid position 381 that defines the plant 1041 mutation is incompatible with nicotine demethylation function, this same mutation was introduced into a CYP82E4v2 cDNA that had been similarly cloned into the pYeDP60 vector. The results of these yeast assays are displayed in Table 3. Whether introduced into the CYP82E10 or CYP82E4v2 enzymes, a Ser substitution for Pro at position 381 leads to the complete ablation of nicotine demethylase activity in this assay. Interestingly, although the activities of the wild type CYP82E10 and CYP82E4v2 enzymes were comparable at the non saturating [$^{14}$C]-nicotine concentration (2.45 µM), at the 25 µM substrate level, the rate of [$^{14}$C]-nornicotine synthesis was nearly three times greater in microsomal preparations possessing the CYP82E10 enzyme than preparations containing CYP82E4v2.

TABLE 2

EMS treated lines of DH98-325-6 with mutations in the CYP82E10 gene.

| Plant Number | Mutation[a] | Amino Acid Change | Activity of Mutant Enzyme[b] |
|---|---|---|---|
| 2476 | G235A | G79S | Not detected |
| 1512 | C319T | P107S | Not detected |
| 319 | C442T | L148F | Not tested |
| 634 | G514A | G172R | Not tested |
| 1035 | G1030A | A344T | 100% |
| 1041 | C1141T | P382S | Not detected |
| 817 | G1228A | A410T | 100% |
| 693 | G1250A | R417H | 100% |
| 1442 | C1255T | P419S | 25% |

[a]In reference to the start codon of the CYP82E10 cDNA sequence.
[b]Relative to the wild type enzyme when expressed in yeast.

TABLE 3

Nicotine demthylase activity of CYP82E4v2 and CYP82E10 enzymes possessing the 1041 mutation (Pro382Ser).

| Vector | CPM nornicotine at 2.45 μM [$^{14}$C]-nicotine substrate[a] | CPM nornicotine at 50.0 μM [$^{14}$C]-nicotine substrate |
|---|---|---|
| pYeDP60-CYPE4v2 | 1,813 ± 623[b] | 5,383 ± 505 |
| pYeDP60-CYPE4v2/1041 | Not detected | Not detected |
| pYeDP60-CYPE10 | 2,296 ± 99 | 15,253 ± 465 |
| pYeDP60-CYPE10/1041 | Not detected | Not detected |

[a]Counts per minute of [$^{14}$C]-nornicotine/mg microsomal protein.
[b]Standard deviation of two technical replications.

Nicotine demethylase activities of wild type and 1041 mutant CYP82E10-expressing yeast cells was also assayed in vivo. Yeast cultures were shaken overnight in the presence of 55 μM [$^{14}$C]-nicotine, extracted with methanol and analyzed by thin layer chromatography. [$^{14}$C]-nornicotine could be detected in the extracts of yeast expressing wild type CYP82E10, but not the 1041 mutant version of the gene (data not shown). Cumulatively, the yeast expression assays strongly suggest that CYP82E10 enzyme function is completely abolished by the introduction of the 1041 mutation.

EXAMPLE 3

Combining Mutant Alleles of cyp82e10, cyp82e4v2 and cyp82e5v2

Given that the original 1041 mutation is in a genetic background (DH98-325-6) that contains both a strong converter CYP82E4v2 allele as well as a wild type CYP82E5v2 gene, the only way to accurately assess the specific contribution of CYP82E10 toward total plant nornicotine content is to introduce the 1041 mutation into tobacco plants possessing knockout CYP82E4v2 and CYP82E5v2 mutations as well. To accomplish this, plants heterozygous for the 1041 mutation (e10E10) were crossed with plants heterozygous for both the 775 and 1013 mutations described above (e4E4/e5E5). The latter plants represent progeny of from the cross 775/1013//TN90/3/TN90/4/TN90. F$_1$ plants heterozygous for all three nicotine demethylase mutations (e4E4/e5E5/e10E10) were identified by molecular genotyping, and allowed to self-pollinate. Molecular genotyping was also used to screen over 400 F$_2$ progeny and subsequently group them into the following genotypic classes: E4E4/E5E5/e10e10 (3 plants total); e4e4/E5E5/e10e10 (4 plants total); E4E4/e5e5/e10e10 (5 plants total); and e4e4/e5e5/e10e10 (5 plants total).

All of the plants described above were transplanted and grown in the field at the Upper Coastal Plains research station in Rocky Mount, N.C. in the summer of 2009. Also included in this study were two of the genotypes tested in the 2008 field trial shown in Table 1. Specifically, ten DH98-325-6 plants homozygous for only the cyp82e4v2 mutation (e4e4/E5E5/E10E10) and eleven DH98-325-6 plants possessing the double homozygous e4e4/e5e5/E10E10 genotype were included for comparison. As controls, individual plants randomly selected from a commercial "low converter" seedlot (TN90LC), wild type DH98-325-6 individuals, and plants from one of the best CYP82E4v2 RNAi-suppressed transgenic lines was also included in the study. After the plants were about an average of 30 cm tall (35 days after transplanting) leaves from similar stalk positions where collected, treated with ethephon and air-cured according to the protocol established by Jack et al. (2007). Alkaloid content of the cured leaf materials was determined by gas chromatography as described in the same protocol.

Table 4 and FIG. 4 shows the results of the alkaloid analyses for the 2009 field trial. Consistent with previous observations, the cyp82e4v2 knockout mutation alone negates the strong converter phenotype of line DH98-325-6, and also confers a substantially lower nornicotine accumulation phenotype than plants from the commercial TN90LC seed (2.2% conversion versus 7.1%, respectively). As observed in the 2008 field trial (Table 1), combining the cyp82e5v2 mutation with cyp82e4v2 did not lead to further reductions in nornicotine content. In fact, the mean nicotine conversion for the e4e4/E5E5/E10E10 plants was actually lower than that observed for e4e4/e5e5/E10E10 individuals (2.2% versus 2.3%), though this slight difference was not statistically significant. As expected, the cyp82e10 mutation had no impact on the high nornicotine levels conferred by an active CYP82E4v2 gene, either alone (E4E4/e5e5/e10e10 genotypes), or when combined with a mutant cyp82e5v2 allele (E4E4/e5e5/e10e10 genotypes) (FIG. 4A). Similar to the cyp82e4v2 and cyp82e5v2 double mutant results (Tables 1 and 4), introducing cyp82e10 into a cyp82e4v2 background was not effective in reducing nornicotine levels below than that which could be achieved by the cyp82e4v2 mutation alone (FIG. 4B). The e4e4/E5E5/e10e10 genotypes averaged 1.85% conversion which was not significantly different than the 2.2% mean conversion levels observed for e4e4/E5E5/E10E10 individuals (P=0.235).

TABLE 4

Alkaloid profiles for experimental materials evaluated in 2009 field experiment. Measurements taken from leaves harvested 35 days after transplanting. Percentage values represent an average.

| Genotype | Gene Targeted | Mutation[b] | Amino Acid Change | % Nicotine[c] | % Nornicotine | % Anabasine | % Anatabine | % Conversion[d] |
|---|---|---|---|---|---|---|---|---|
| DH98-325-6 control (8)[a] | Control | — | — | 0.133 | 1.553 | 0.009 | 0.085 | 92.21 |
| TN90LC (11) | Control | — | — | 1.519 | 0.104 | 0.002 | 0.065 | 7.15 |
| DH98-325-6 RNAi 300-02 #1 (10) | CYP82E4v2 and related | — | — | 1.747 | 0.009 | 0.003 | 0.063 | 0.54 |
| DH98-325-6 #775 Homo. (10) | CYP82E4v2 | G986A | W329Stop | 1.375 | 0.030 | 0.002 | 0.057 | 2.20 |
| DH98-325-6 Double Homo. Mutant (11) | CYP82E4v2 CYP82E5v2 | Double | Double | 1.524 | 0.036 | 0.003 | 0.084 | 2.34 |
| DH980325-6 #1041 Homo. (3) | CYP82E10 | C1141T | P382S | 0.082 | 1.302 | 0.007 | 0.073 | 93.87 |
| DH98-325-6 Double Homo. Mutant (5) | CYP82E5v2 CYP82E10 | Double | Double | 0.081 | 1.345 | 0.010 | 0.068 | 94.31 |
| DH98-325-6 Double Homo. Mutant (4) | CYP82E4v2 CYP82E10 | Double | Double | 2.168 | 0.045 | 0.004 | 0.087 | 1.85 |

TABLE 4-continued

Alkaloid profiles for experimental materials evaluated in 2009 field experiment. Measurements taken from leaves harvested 35 days after transplanting. Percentage values represent an average.

| Genotype | Gene Targeted | Mutation[b] | Amino Acid Change | % Nicotine[c] | % Nornicotine | % Anabasine | % Anatabine | % Conversion[d] |
|---|---|---|---|---|---|---|---|---|
| DH98-325-6 Triple Homo. Mutant (5) | CYP82E4v2 CYP82E5v2 CYP82E10 | Triple | Triple | 1.793 | 0.012 | 0.003 | 0.056 | 0.55 |

[a]Number in parentheses indicates total number of plants analyzed.
[b]Numbering relative to start codon of cDNA sequence.
[c]Percentages were calculated on a dry tobacco weight basis.
[d]Percentage nicotine conversion equals [% nornicotine/(% nornicotine + % nicotine)] × 100.

Although the cyp82e5v2 and cyp82e10 mutations did not serve to significantly decrease the nornicotine content of cyp82e4v2 plants when combined individually, pyramiding all three nicotine demethylase mutations had a very notable effect. Nicotine to nornicotine conversion in triple mutant plants (e4e4/e5e5/e10e10) averaged only 0.55%, a percentage virtually identical to the 0.54% observed in the RNAi-suppressed transgenic line ($P=0.893$; FIG. 4B). This represents over a 3-fold reduction in nicotine conversion beyond that which was mediated by the cyp82e4v2 mutation alone. Statistically, the differences in percent nicotine conversion (and nornicotine accumulation as a percentage of total dry weight) between e4e4/E5E5/E10E10 and e4e4/e5e5/e10e10 genotypes was highly significant ($P<0.0001$). Similar to the investigation of RNAi-mediated suppression of nicotine conversion (Lewis et al., 2008), the present nontransgenic alteration of nicotine demethylase activities in the tobacco plant did not appear to significantly alter the content of the minor alkaloid species anatabine and anabasine.

The effects of pyramiding the three independent nicotine demethylase gene mutations were also tested in a field trial conducted during the 2010 growing season. For this study, the crosses were conducted entirely within the DH98-325-6 genetic background (in contrast to the 2009 study where a TN90 parent was also used). Molecular genotyping was again used to create every possible combination needed to determine the respective contributions of each CYP82E locus on the nornicotine phenotype. Alkaloid data were collected on tobacco plants that were grown to maturity and cured according to standard industry practice. As shown in Table 5, a high level of nicotine conversion (ranging from 52.4-65.59%) was observed in all genotypes homozygous for a wild type CYP82E4v2 gene (genotypes E4E4/E5E5/E10E10, E4E4/e5e5/E10E10, E4E4/E5E5/e10e10, and E4E4/e5e5/e10e10). Plants homozygous for just the cyp82e4v2 mutation (e4e4/E5E5/E10E10) averaged 2.91% nicotine to nornicotine conversion. Similar to the 2009 results, the effects of the cyp82E5v2 and cyp82E10 mutations were not additive, and were only manifest when all three mutant loci were pyramided together. DH98-325-6 (e4e4/E5E5/e10e10) plants averaged 2.89% conversion and DH98-325-6 (e4e4/e5e5/E10E10) individuals averaged 2.52%, values that were not statistically different than that observed with the cyp82e4v2 mutation alone. In contrast, the reduction in nornicotine observed in the triple mutant DH98-325-6 (e4e4/e5e5/e10e10) genotype (1.11% nicotine conversion) was 2.6-fold lower than that attained via the cyp82e4v2 mutation alone. The reduction in nicotine conversion attributable to the triple mutant combination was highly significant ($P<0.001$) compared with either cyp82e4v2 alone or any double mutant combination.

TABLE 5

Alkaloid profiles for DH98-325-6 genotypes possessing different mutation combinations at the CYP82E4v2 (E4), CYP82Ev25 (E5), and CYP82E10 (E10) loci. Data are averaged over five replications and generated from analysis of composite ground samples of the fourth and fifth leaves from the top of the plant.

| Genotype | Nicotine (%) | Nornicotine (%) | Anabasine (%) | Anatabine (%) | Nicotine Conversion (%) |
|---|---|---|---|---|---|
| DH98-325-6 E4E4 E5E5 E10E10 | 1.76 | 2.46 | 0.02 | 0.17 | 58.66 |
| DH98-325-6 e4e4 E5E5 E10E10 | 2.61 | 0.08 | 0.01 | 0.09 | 2.91 |
| DH98-325-6 E4E4 e5e5 E10E10 | 1.08 | 2.06 | 0.02 | 0.14 | 65.59 |
| DH98-325-6 E4E4 E5E5 e10e10 | 1.40 | 1.96 | 0.01 | 0.13 | 59.30 |
| DH98-325-6 e4e4 e5e5 E10E10 | 3.25 | 0.09 | 0.02 | 0.16 | 2.89 |
| DH98-325-6 e4e4 E5E5 e10e10 | 3.59 | 0.09 | 0.01 | 0.12 | 2.52 |
| DH98-325-6 E4E4 e5e5 e10e10 | 1.59 | 1.72 | 0.01 | 0.09 | 52.40 |
| DH98-325-6 e4e4 e5e5 e10e10 | 4.18 | 0.05 | 0.02 | 0.13 | 1.11 |

Alkaloid percentages were calculated on a dry weight basis
Percentage nicotine conversion equals [% nornicotine/(% nornicotine + % nicotine)] × 100

CONCLUSIONS

Through the present discovery and characterization of a new nicotine demethylase gene, CYP82E10, it has been possible to develop a strategy for reducing the nicotine conversion rates (and thus nornicotine levels) in commercial grade air-cured tobacco plants to levels that have previously only been possible using transgenic approaches. This non-GMO based technology can reduce the levels of nornicotine to a degree similar to that which has been achieved using transgenic strategies, yet offers the tremendous advantage of serving as a means for developing ultra-low nornicotine tobacco varieties while bypassing the substantial hurdles associated with the commercialization of transgenic crops, such as: (1) negotiating and paying licensing fees for the several enabling technologies required for generating transgenic plants; (2) avoiding the lengthy time and onerous costs associated with the deregulation of a transgenic event; and (3) encountering the possibility of product rejection by end users philosophically opposed to GMOs. The discovery reported here represents a major advancement in our ability to lower the levels of one of the most well documented strong carcinogens found in tobacco products, in comparison with the previously described non-GMO strategies that only targeted mutations in the CYP82E4v2 nicotine demethylase gene (Julio et al., 2008; Xu et al., 2007b) or combined CYP82E4v2 and CYP82E5v2 mutations (Dewey et al., 2007). Using transgenic technologies, it was previously demonstrated that lowering nicotine conversion levels from ~2.6% to ~0.5% in the cured leaf lead to a commensurate reduction in the NNN content of the leaf as well (Lewis et al., 2008). One would expect to see similar reductions in the NNN content from tobacco leaves containing the triple mutant combination (e4e4/e5e5/e10e10) described in this report. Although originally targeted for air-cured tobaccos, this technology will be of benefit to flue-cured varieties as well. As heat exchangers age, their ability to remove $NO_x$ gases during flue-curing can decrease. Furthermore, recent studies have shown that a considerable amount of TSNA formation can occur during the storage of the cured leaf. Minimizing nornicotine levels through the introduction of the triple mutant combination in flue-cured varieties can act as a safeguard against NNN formation either during storage or as a consequence of inefficient heat exchange during the curing process.

REFERENCES

Altschul, S. F., Gish, W., Miller, W., Myers, E. W. and Lipman, D. J. 1990. Basic local alignment search tool. *J. Mol. Biol.* 215: 403-410.

Altschul, S. F., Madden, T. L., Schaffer, A. A., Zhang, J., Zhang, Z., Miller, W. and Lipman, D. J. 1997. Gapped BLAST and PSI-BLAST: a new generation of protein database search programs. *Nucleic Acids Res* 25: 3389-3402.

Brogan, A. P., Dickerson, T. J., Boldt, G. E. and Janda, K. D. 2005. Altered retinoid homeostasis catalyzed by nicotine metabolite: implications in macular degeneration and normal development. *Proc. Natl. Acad. Sci. USA* 102: 10433-10438.

Boyette, M. D. and Hamm, L. A. 2001. Results of year 2000 TSNA sampling program in flue-cured tobacco. *Rec. Adv. Tob. Sci.* 27: 17-22.

Bush, L. P., Cui, M., Shi, H., Burton, H. R., Fannin, F. F., Lei, L. and Dye, N. 2001. Formation of tobacco-specific nitrosamines in air-cured tobacco. *Rec. Adv. Tob. Sci.* 27: 23-46.

Chakrabarti, M., Meekins, K. M., Gavilano, L. B. and Siminszky, B. 2007. Inactivation of the cytochrome P450 gene CYP82E2 by degenerative mutations was a key event in the evolution of the alkaloid profile of modern tobacco. *New Phytol.* 175: 565-574.

Dewey, R. E., Siminszky, B., Bowen, S. W. and Gavilano, L. 2007. Alteration of tobacco alkaloid content through modification of specific cytochrome P450 genes. U.S. Patent Application 60/987,243.

Dickerson, T. J. and Janda, K. D. 2002. A previously undescribed chemical link between smoking and metabolic disease. *Proc. Natl. Acad. Sci. USA* 99: 15084-15088.

Gavilano, L. B., Coleman, N. P., Bowen, S. W. and Siminszky, B. 2007. Functional analysis of nicotine demethylase genes reveals insights into the evolution of modern tobacco. *J. Biol. Chem.* 282: 249-256.

Gavilano, L. B. and Siminszky, B. 2007. Isolation and characterization of the cytochrome P450 gene CYP82E5v2 that mediates nicotine to nornicotine conversion in the green leaves of tobacco. *Plant Cell Physiol.* 48: 1567-1574.

Hecht, S. S. 1998. Biochemistry, biology and carcinogenicity of tobacco-specific N-nitrosamines. *Chem. Res. Toxicol.* 11: 559-603.

Hecht, S. S. 2003. Tobacco carcinogens, their biomarkers and tobacco-induced cancer. *Nature Rev.* 3: 733-744.

Hecht, S. S. and Hoffmann, D. 1990. The relevance of tobacco specific nitrosamines to human cancer. *Cancer Surveys* 8: 273-294.

Hoffmann, D., Brunnemann, K. D., Prokopczyk, B. and Djordjevic, M. V. 1994. Tobacco-specific N-nitrosamines and Areca-derived N-nitrosamine chemistry, biochemistry, carcinogenicity and relevance to humans. *J. Toxicol. Environ. Health* 41: 1-52.

Jack, A., Fannin, N. and Bush, L. P. 2007. Implications of reducing nornicotine accumulation in burley tobacco: Appendix A—The LC Protocol. *Rec. Adv. Tob. Sci.* 33: 58-79.

Julio, E., Laporte, F., Reis, S., Rothan, C. and Dorlhac de Borne, F. 2008. Reducing the content of nornicotine in tobacco via targeted mutation breeding. *Mol. Breed.* 21: 369-381.

Katz, J., Caudle, R. M., Bhattacharyya, I., Stewart, C. M. and Cohen, D. M. 2005. Receptor for advanced glycation end product (RAGE) upregulation in human gingival fibroblasts incubated with nornicotine. *J. Periodontol.* 76: 1171-1174.

Lewis, R. S., Jack, A. M., Morris, J. W., Robert, V. J. M., Gavilano, L., Siminszky, B., Bush, L. P., Hayes, A. J. and Dewey, R. E. 2008. RNAi-induced suppression of nicotine demethylase activity reduces levels of a key carcinogen in cured tobacco leaves. *Plant Biotech. J.* 6: 346-354.

Peele, D. M. and Gentry, J. S. 1999. Formation of tobacco-specific nitrosamines in flue-cured tobacco. CORESTA Meeting, Agro-Phyto Groups, Suzhou, China.

Pompon, D., Louerat, B., Bronne, A. and Urban, P. 1995. Yeast expression of animal and plant P450s in optimized redox environments. *Methods Enzymol.* 272: 51-64.

Siminszky, B., Gavilano, L., Bowen, S. W. and Dewey, R. E. 2005. Conversion of nicotine to nornicotine in *Nicotiana tabacum* is mediated by CYP82E4, a cytochrome P450 monooxygenase. *Proc. Natl. Acad. Sci. USA* 102: 14919-14924.

Wernsman, E. A. and Matzinger, D. F. 1968. Time and site of nicotine conversion in tobacco. *Tob. Sci.* 12: 226-228.

Xu, D., Shen, Y., Chappell, J., Cui, M. and Nielsen, M. 2007a. Biochemical and molecular characterization of nicotine demethylase in tobacco. *Physiol. Plantarum* 129: 307-319.

Xu, D., Nielsen, M. T. and Shen, Y. 2007b. Tobacco plants having a mutation in a nicotine demethylase gene. U.S. Patent Application 20070199097.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the list of embodiments and appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. Cured tobacco material or a tobacco product comprising said cured tobacco material, wherein said cured tobacco material is made from a tobacco plant comprising a first mutation in a CYP82E10 nicotine demethylase, wherein said first mutation results in reduced expression or function of said CYP82E10 nicotine demethylase, and wherein said tobacco plant is a *Nicotiana tabacum* plant.

2. The cured tobacco material or a tobacco product comprising said cured tobacco material, according to claim 1, wherein said tobacco plant further comprises a second mutation in a CYP82E4 nicotine demethylase, wherein said second mutation results in reduced expression or function of said CYP82E4 nicotine demethylase.

3. The cured tobacco material or a tobacco product comprising said cured tobacco material, according to claim 1, wherein said tobacco plant further comprises a second mutation in a CYP82E5v2 nicotine demethylase, wherein said second mutation results in reduced expression or function of said CYP82E5v2 nicotine demethylase.

4. The cured tobacco material or a tobacco product comprising said cured tobacco material, according to claim 2, wherein said tobacco plant further comprises a third mutation in a CYP82E5v2 nicotine demethylase, wherein said third mutation results in reduced expression or function of said CYP82E5v2 nicotine demethylase.

5. The tobacco product according to claim 4.

6. The tobacco product according to claim 4, wherein said first mutation results in a Proline to Serine substitution at amino acid position 381 of CYP82E10 and said CYP82E10 numbering is according to SEQ ID NO:2; wherein said second mutation results in a Tryptophan to stop codon substitution at amino acid position 329 of CYP82E4 and said CYP82E4 numbering is according to SEQ ID NO:14; and wherein said third mutation results in a Tryptophan to stop codon substitution at amino acid position 422 of CYP82E5v2 and said CYP82E5v2 numbering is according to SEQ ID NO:26.

7. The tobacco product according to claim 4, wherein each of said mutations is homozygous.

8. The tobacco product according to claim 4, wherein said tobacco material is made by a curing process selected from the group consisting of flue curing, air curing, and fire curing.

9. The tobacco product according to claim 4, wherein said tobacco product is selected from the group consisting of a cigar, a cigarette, pipe tobacco, a cigarillo, a non-ventilated or vented recess filter cigarette, a dissolving strip, a gum, a tablet, snuff, and chewing tobacco.

10. The tobacco product according to claim 4, wherein said cured tobacco material comprises a lower level of nornicotine or N'-nitrosonornicotine compared to cured tobacco material made from a tobacco plant comprising wild type alleles CYP82E4, CYP82E5v2, and CYP82E10.

11. The tobacco product according to claim 4, wherein the conversion of nicotine to nornicotine in said cured tobacco material is selected from the group consisting of less than 0.3%, less than 0.5%, less than 0.7%, between 0.1%-0.5%, between 0.1%-0.4%, between 0.1%-0.7%, and between 0.1%-1.0%.

12. The tobacco product according to claim 4, wherein said tobacco plant has a non-converter phenotype and reduced nicotine demethylase activity.

13. The tobacco product according to claim 4, wherein said tobacco plant is a hybrid.

14. The tobacco product according to claim 4, wherein said tobacco plant is selected from the group consisting of a Burley type, a dark type, a flue-cured type, and an Oriental type.

15. The tobacco product according to claim 4, wherein said first, second, or third mutation is selected from the group consisting of a point mutation, a deletion, an insertion, and an inversion.

16. The tobacco product according to claim 4, wherein said CYP82E10 mutation comprises a Cytosine to Thymine substitution at nucleic acid position 1141.

17. The tobacco product according to claim 4, wherein said CYP82E10 mutation comprises a Cytosine to Thymine substitution at nucleic acid position 1141; wherein said nucleic acid position numbering is according to SEQ ID NO:1; wherein said second mutation results in a Tryptophan to stop codon substitution at amino acid position 329 of CYP82E4 and said CYP82E4 numbering is according to SEQ ID NO:14; and wherein said third mutation results in a Tryptophan to stop codon substitution at amino acid position 422 of CYP82E5v2 and said CYP82E5v2 numbering is according to SEQ ID NO:26.

18. A tobacco seed, tobacco plant developed therefrom, or plant part thereof, said tobacco plant comprising a CYP82E10 nicotine demethylase having a Cytosine to Thymine mutation at nucleic acid position 1141, and said CYP82E10 position numbering is according to SEQ ID NO:1; said tobacco plant also comprising a CYP82E4 nicotine demethylase having a mutation at amino acid position 329, and said CYP82E4 numbering is according to SEQ ID NO:14; and said tobacco plant further comprising a CYP82E5v2 nicotine demethylase having a mutation at amino acid position 422, wherein said CYP82E5v2 numbering is according to SEQ ID NO:26; and wherein said tobacco plant is a *Nicotiana tabacum* plant.

19. The tobacco seed, tobacco plant developed therefrom, or plant part thereof, according to claim 18, wherein said CYP82E4 mutation at amino acid position 329 and said CYP82E5 mutation at amino acid position 422 both result in a stop codon.

\* \* \* \* \*

SEQUENCE LISTING

```
<160> NUMBER OF SEQ ID NOS: 40

<210> SEQ ID NO 1
<211> LENGTH: 1551
<212> TYPE: DNA
<213> ORGANISM: Nicotiana tabacum
<220> FEATURE:
<221> NAME/KEY: CDS
<222> LOCATION: (1)...(1551)
<223> OTHER INFORMATION: Encodes CYP82E10 nicotine demethylase

<400> SEQUENCE: 1 atg gtt tct ccc gta gaa gcc atc gta gga cta gta act ctt aca ctt     48
Met Val Ser Pro Val Glu Ala Ile Val Gly Leu Val Thr Leu Thr Leu
 1               5                  10                  15 ctc ttc tac ttc ata cgg acc aaa aaa tct caa aaa cct tca aaa cca     96
Leu Phe Tyr Phe Ile Arg Thr Lys Lys Ser Gln Lys Pro Ser Lys Pro
             20                  25                  30 tta cca ccg aaa atc ccc gga ggg tgg ccg gta atc ggc cat ctt ttc    144
Leu Pro Pro Lys Ile Pro Gly Gly Trp Pro Val Ile Gly His Leu Phe
         35                  40                  45 tat ttc gat gac gac agc gac gac cgt cca tta gca cga aaa ctc gga    192
Tyr Phe Asp Asp Asp Ser Asp Asp Arg Pro Leu Ala Arg Lys Leu Gly
     50                  55                  60 gac tta gct gac aaa tac ggc ccg gtt ttc act ttt cgg cta ggc ctt    240
Asp Leu Ala Asp Lys Tyr Gly Pro Val Phe Thr Phe Arg Leu Gly Leu
 65                  70                  75                  80 ccg ctt gtg tta gtt gta agc agt tac gaa gct ata aaa gac tgc ttc    288
Pro Leu Val Leu Val Val Ser Ser Tyr Glu Ala Ile Lys Asp Cys Phe
                 85                  90                  95 tct aca aat gat gcc att ttc tcc aat cgt cca gct ttt ctt tat ggc    336
Ser Thr Asn Asp Ala Ile Phe Ser Asn Arg Pro Ala Phe Leu Tyr Gly
            100                 105                 110 gaa tac ctt ggc tac aat aat gcc atg cta ttt ttg aca aaa tac gga    384
Glu Tyr Leu Gly Tyr Asn Asn Ala Met Leu Phe Leu Thr Lys Tyr Gly
        115                 120                 125 cct tac tgg cga aaa aat aga aaa tta gtc att cag gaa gtt ctc tgt    432
Pro Tyr Trp Arg Lys Asn Arg Lys Leu Val Ile Gln Glu Val Leu Cys
    130                 135                 140 gct agt cgt ctc gaa aaa ttg aag cac gtg aga ttt ggt gaa att cag    480
Ala Ser Arg Leu Glu Lys Leu Lys His Val Arg Phe Gly Glu Ile Gln
145                 150                 155                 160 acg agc att aag aat tta tac act cga att gat gga aat tcg agt acg    528
Thr Ser Ile Lys Asn Leu Tyr Thr Arg Ile Asp Gly Asn Ser Ser Thr
                165                 170                 175 ata aat cta acc gat tgg tta gaa gaa ttg aat ttt ggt ctg atc gtg    576
Ile Asn Leu Thr Asp Trp Leu Glu Glu Leu Asn Phe Gly Leu Ile Val
            180                 185                 190 aaa atg atc gct ggg aaa aat tat gaa tcc ggt aaa gga gat gaa caa    624
Lys Met Ile Ala Gly Lys Asn Tyr Glu Ser Gly Lys Gly Asp Glu Gln
        195                 200                 205 gtg gag aga ttt agg aaa gcg ttt aag gat ttt ata att tta tca atg    672
Val Glu Arg Phe Arg Lys Ala Phe Lys Asp Phe Ile Ile Leu Ser Met
    210                 215                 220
```

```
gag ttt gtg tta tgg gat gct ttt cca att cca ttg ttc aaa tgg gtg        720
Glu Phe Val Leu Trp Asp Ala Phe Pro Ile Pro Leu Phe Lys Trp Val
225                 230                 235                 240 gat ttt caa ggc cat gtt aag gcc atg aaa agg aca ttt aag gat ata        768
Asp Phe Gln Gly His Val Lys Ala Met Lys Arg Thr Phe Lys Asp Ile
            245                 250                 255 gat tct gtt ttt cag aat tgg tta gag gaa cat gtc aag aaa aaa gaa        816
Asp Ser Val Phe Gln Asn Trp Leu Glu Glu His Val Lys Lys Lys Glu
        260                 265                 270 aaa atg gag gtt aat gca gaa gga aat gaa caa gat ttc att gat gtg        864
Lys Met Glu Val Asn Ala Glu Gly Asn Glu Gln Asp Phe Ile Asp Val
    275                 280                 285 gtg ctt tca aaa atg agt aat gaa tat ctt gat gaa ggc tac tct cgt        912
Val Leu Ser Lys Met Ser Asn Glu Tyr Leu Asp Glu Gly Tyr Ser Arg
290                 295                 300 gat act gtc ata aaa gca aca gtg ttt agt tta gtc ttg gat gct gcg        960
Asp Thr Val Ile Lys Ala Thr Val Phe Ser Leu Val Leu Asp Ala Ala
305                 310                 315                 320 gac aca gtt gct ctt cac atg aat tgg gga atg gca tta ttg ata aac       1008
Asp Thr Val Ala Leu His Met Asn Trp Gly Met Ala Leu Leu Ile Asn
            325                 330                 335 aat caa cat gcc ttg aag aaa gcg caa gaa gag ata gat aaa aaa gtt       1056
Asn Gln His Ala Leu Lys Lys Ala Gln Glu Glu Ile Asp Lys Lys Val
        340                 345                 350 ggt aag gat aga tgg gta gaa gag agt gat att aag gat ttg gta tac       1104
Gly Lys Asp Arg Trp Val Glu Glu Ser Asp Ile Lys Asp Leu Val Tyr
    355                 360                 365 ctc caa act att gtt aaa gaa gtg tta cga tta tat cca ccg gga cct       1152
Leu Gln Thr Ile Val Lys Glu Val Leu Arg Leu Tyr Pro Pro Gly Pro
370                 375                 380 tta tta gta ccc cat gaa aat gta gag gat tgt gtt gtt agt gga tat       1200
Leu Leu Val Pro His Glu Asn Val Glu Asp Cys Val Val Ser Gly Tyr
385                 390                 395                 400 cac att cct aaa ggg act aga cta ttc gcg aac gtt atg aaa tta cag       1248
His Ile Pro Lys Gly Thr Arg Leu Phe Ala Asn Val Met Lys Leu Gln
            405                 410                 415 cgc gat cct aaa ctc tgg tca aat cct gat aag ttc gat cca gag aga       1296
Arg Asp Pro Lys Leu Trp Ser Asn Pro Asp Lys Phe Asp Pro Glu Arg
        420                 425                 430 ttt ttc gct gct gat att gac ttt cgt ggt caa cac tat gag ttt atc       1344
Phe Phe Ala Ala Asp Ile Asp Phe Arg Gly Gln His Tyr Glu Phe Ile
    435                 440                 445 cca ttt ggt tct gga aga cga tct tgt ccg ggg atg act tat gca atg       1392
Pro Phe Gly Ser Gly Arg Arg Ser Cys Pro Gly Met Thr Tyr Ala Met
450                 455                 460 caa gtg gaa cac cta aca atc gca cac ttg atc cag ggt ttc aat tac       1440
Gln Val Glu His Leu Thr Ile Ala His Leu Ile Gln Gly Phe Asn Tyr
465                 470                 475                 480 aaa act cca aat gac gag ccc ttg gat atg aag gaa ggt gca gga tta       1488
Lys Thr Pro Asn Asp Glu Pro Leu Asp Met Lys Glu Gly Ala Gly Leu
            485                 490                 495 act ata cgt aag gta aat cct ata gaa gtg gta att acg cct cgc ctg       1536
Thr Ile Arg Lys Val Asn Pro Ile Glu Val Val Ile Thr Pro Arg Leu
        500                 505                 510 aca cct gag ctt tat                                                   1551
Thr Pro Glu Leu Tyr
    515

<210> SEQ ID NO 2
```

<211> LENGTH: 517
<212> TYPE: PRT
<213> ORGANISM: Nicotiana tabacum

<400> SEQUENCE: 2

```
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
```

```
                385                 390                 395                 400
        His Ile Pro Lys Gly Thr Arg Leu Phe Ala Asn Val Met Lys Leu Gln
                        405                 410                 415

Arg Asp Pro Lys Leu Trp Ser Asn Pro Asp Lys Phe Asp Pro Glu Arg
                        420                 425                 430

Phe Phe Ala Ala Asp Ile Asp Phe Arg Gly Gln His Tyr Glu Phe Ile
                        435                 440                 445

Pro Phe Gly Ser Gly Arg Arg Ser Cys Pro Gly Met Thr Tyr Ala Met
                450                 455                 460

Gln Val Glu His Leu Thr Ile Ala His Leu Ile Gln Gly Phe Asn Tyr
        465                 470                 475                 480

Lys Thr Pro Asn Asp Glu Pro Leu Asp Met Lys Glu Gly Ala Gly Leu
                        485                 490                 495

Thr Ile Arg Lys Val Asn Pro Ile Glu Val Val Ile Thr Pro Arg Leu
                        500                 505                 510

Thr Pro Glu Leu Tyr
                515

<210> SEQ ID NO 3
<211> LENGTH: 818
<212> TYPE: DNA
<213> ORGANISM: Nictoiana tabacum
<220> FEATURE:
<221> NAME/KEY: intron
<222> LOCATION: (1)...(818)
<223> OTHER INFORMATION: Intron for CYP82E10 gene

<400> SEQUENCE: 3
gtaagttcat ctcatttttc atttattctt tgaggaatag acaggttaat agtaatttaa     60
gtaattagat tatctaaata ctaaggatga gtaaatatgg caaaaatata gaatgataaa    120
tggaaaagga tgataatttt ttatgcccgg actaatctaa ctttgggagt taaagcactt    180
cctaccaata gggactttc ttcaagctcg atcttgatga aactctgtgg ttaaaaaaat    240
gagatatanc caattataat tgatagaata aaactttatt actcccattg agcataacaa    300
aacaaaaaaa agtaaaggga cttcttctct tttttaggga gaaattcttt gattgtttgt    360
taatatagat tcatgttttt tttattttct aataataatt gtgcttgaat caggtcgcgc    420
tgattcttgg cttttttagca gcaatagagt caaagctaat atacatatta tttggttttc    480
gaataagtta tactgaaatt atataatacg ggtattaaat aataacatga ttatttatag    540
gatatgcttt ttttattggg taaatatatt tttttttaatt aaaaatgaaa tatacaagta    600
aggtataaaa cactatttga ttttacacta gataaatttg ccctcgtaca tctctaagag    660
aagagctgaa ataatgaat tttaaatttc agaaaaaaat aaattcatta gtataatgag    720
atgtcgatac ttgacaatta ctatactaac tagaacaagg ttcagcagat agtgacgcta    780
acctattttt gtattgaatt attctaattt gtccacag                           818

<210> SEQ ID NO 4
<211> LENGTH: 2636
<212> TYPE: DNA
<213> ORGANISM: Nicotiana tabacum
<220> FEATURE:
<221> NAME/KEY: 5'UTR
<222> LOCATION: (1)...(114)
<223> OTHER INFORMATION: CYP82E10 5' UTR
<220> FEATURE:
<221> NAME/KEY: exon
<222> LOCATION: (115)...(1053)
<223> OTHER INFORMATION: CYP82E10 exon 1 sequence
```

```
<220> FEATURE:
<221> NAME/KEY: intron
<222> LOCATION: (1054)...(1871)
<223> OTHER INFORMATION: CYP82E10 intron sequence
<220> FEATURE:
<221> NAME/KEY: exon
<222> LOCATION: (1872)...(2483)
<223> OTHER INFORMATION: CYP82E10 exon 2 sequence
<220> FEATURE:
<221> NAME/KEY: 3'UTR
<222> LOCATION: (2484)...(2636)
<223> OTHER INFORMATION: CYP82E10 3' UTR

<400> SEQUENCE: 4
```

| | | | | | |
|---|---|---|---|---|---|
| ttttcaattt | tgttactttt | tgtatttatc | atattattat | gcatagccct | aaattatcta | 60 |
| taaaagggaa | gttggtgata | gtttgattcc | caagtgcttt | tctaaaaatc | cataatggtt | 120 |
| tctcccgtag | aagccatcgt | aggactagta | actcttacac | ttctcttcta | cttcatacgg | 180 |
| accaaaaaat | ctcaaaaacc | ttcaaaacca | ttaccaccga | aaatccccgg | agggtggccg | 240 |
| gtaatcggcc | atcttttcta | tttcgatgac | gacagcgacg | accgtccatt | agcacgaaaa | 300 |
| ctcggagact | tagctgacaa | atacggcccg | gttttcactt | ttcggctagg | ccttccgctt | 360 |
| gtgttagttg | taagcagtta | cgaagctata | aaagactgct | tctctacaaa | tgatgccatt | 420 |
| ttctccaatc | gtccagcttt | tctttatggc | gaataccttg | gctacaataa | tgccatgcta | 480 |
| tttttgacaa | atacggacc | ttactggcga | aaaatagaa | aattagtcat | tcaggaagtt | 540 |
| ctctgtgcta | gtcgtctcga | aaaattgaag | cacgtgagat | ttggtgaaat | tcagacgagc | 600 |
| attaagaatt | tatacactcg | aattgatgga | aattcgagta | cgataaatct | aaccgattgg | 660 |
| ttagaagaat | tgaattttgg | tctgatcgtg | aaaatgatcg | ctgggaaaaa | ttatgaatcc | 720 |
| ggtaaaggag | atgaacaagt | ggagagattt | aggaaagcgt | ttaaggattt | tataatttta | 780 |
| tcaatggagt | ttgtgttatg | ggatgctttt | ccaattccat | tgttcaaatg | ggtggatttt | 840 |
| caaggccatg | ttaaggccat | gaaaaggaca | tttaaggata | tagattctgt | ttttcagaat | 900 |
| tggttagagg | aacatgtcaa | gaaaaagaa | aaaatggagg | ttaatgcaga | aggaaatgaa | 960 |
| caagatttca | ttgatgtggt | gctttcaaaa | atgagtaatg | aatatcttga | tgaaggctac | 1020 |
| tctcgtgata | ctgtcataaa | agcaacagtg | tttgtaagtt | catctcatt | ttcatttatt | 1080 |
| ctttgaggaa | tagacaggtt | aatagtaatt | taagtaatta | gattatctaa | atactaagga | 1140 |
| tgagtaaata | tggcaaaaat | atagaatgat | aaatggaaaa | ggatgataat | ttttatgcc | 1200 |
| cggactaatc | taactttggg | agttaaagca | cttcctacca | atagggactt | ttcttcaagc | 1260 |
| tcgatcttga | tgaaactctg | tggttaaaaa | aatgagatat | anccaattat | aattgataga | 1320 |
| ataaaacttt | attactccca | ttgagcataa | caaaacaaaa | aaagtaaag | ggacttcttc | 1380 |
| tctttttag | ggagaaattc | tttgattgtt | tgttaatata | gattcatgtt | ttttttatt | 1440 |
| tctaataata | attgtgcttg | aatcaggtcg | cgctgattct | tggcttttta | gcagcaatag | 1500 |
| agtcaaagct | aatatacata | ttatttggtt | ttcgaataag | ttatactgaa | attatataat | 1560 |
| acgggtatta | ataataaca | tgattatta | taggatatgc | tttttttatt | gggtaaatat | 1620 |
| atttttttta | attaaaaatg | aaatatacaa | gtaaggtata | aaacactatt | tgattttaca | 1680 |
| ctagataaat | ttgccctcgt | acatctctaa | gagaagagct | gaaataaatg | aattttaaat | 1740 |
| ttcagaaaaa | aataaattca | ttagtataat | gagatgtcga | tacttgacaa | ttactatact | 1800 |
| aactagaaca | aggttcagca | gatagtgacg | ctaacctatt | tttgtattga | attattctaa | 1860 |
| tttgtccaca | gagtttagtc | ttggatgctg | cggacacagt | tgctcttcac | atgaatttggg | 1920 |

-continued

```
gaatggcatt attgataaac aatcaacatg ccttgaagaa agcgcaagaa gagatagata    1980
aaaaagttgg taaggataga tgggtagaag agagtgatat taaggatttg gtatacctcc    2040
aaactattgt taaagaagtg ttacgattat atccaccggg acctttatta gtaccccatg    2100
aaaatgtaga ggattgtgtt gttagtggat atcacattcc taagggact  agactattcg    2160 cgaacgttat gaaattacag cgcgatccta aactctggtc aaatcctgat aagttcgatc    2220
cagagagatt tttcgctgct gatattgact ttcgtggtca acactatgag tttatcccat    2280
ttggttctgg aagacgatct tgtccgggga tgacttatgc aatgcaagtg gaacacctaa    2340
caatcgcaca cttgatccag ggtttcaatt acaaaactcc aaatgacgag cccttggata    2400
tgaaggaagg tgcaggatta actatacgta aggtaaatcc tatagaagtg gtaattacgc    2460
ctcgcctgac acctgagctt tattaaaatc taagatgttt tatcttggtt gatcattgtt    2520
taatactcct agatagatgg gtattcatct atctttttaa aattaattgt cagtacgagt    2580
gtttctaatt tggtaagttt gtaacaacaa gtaagaaggg attgtgctag tatgta        2636
```

<210> SEQ ID NO 5
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E10 L148F variant

<400> SEQUENCE: 5

```
Met Val Ser Pro Val Glu Ala Ile Val Gly Leu Val Thr Leu Thr Leu
 1               5                  10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Asp Ser Asp Asp Arg Pro Leu Ala Arg Lys Leu Gly
        50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Ile Lys Asp Cys Phe
                 85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Phe Glu Lys Leu Lys His Val Arg Phe Gly Glu Ile Gln
145                 150                 155                 160

Thr Ser Ile Lys Asn Leu Tyr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
```

```
                225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Lys Glu
                260                 265                 270
Lys Met Glu Val Asn Ala Glu Gly Asn Glu Gln Asp Phe Ile Asp Val
                275                 280                 285
Val Leu Ser Lys Met Ser Asn Glu Tyr Leu Asp Glu Gly Tyr Ser Arg
                290                 295                 300
Asp Thr Val Ile Lys Ala Thr Val Phe Ser Leu Val Leu Asp Ala Ala
305                 310                 315                 320
Asp Thr Val Ala Leu His Met Asn Trp Gly Met Ala Leu Leu Ile Asn
                325                 330                 335
Asn Gln His Ala Leu Lys Lys Ala Gln Glu Glu Ile Asp Lys Lys Val
                340                 345                 350
Gly Lys Asp Arg Trp Val Glu Glu Ser Asp Ile Lys Asp Leu Val Tyr
                355                 360                 365
Leu Gln Thr Ile Val Lys Glu Val Leu Arg Leu Tyr Pro Pro Gly Pro
                370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asn Pro Asp Lys Phe Asp Pro Glu Arg
                420                 425                 430
Phe Phe Ala Ala Asp Ile Asp Phe Arg Gly Gln His Tyr Glu Phe Ile
                435                 440                 445
Pro Phe Gly Ser Gly Arg Arg Ser Cys Pro Gly Met Thr Tyr Ala Met
                450                 455                 460
Gln Val Glu His Leu Thr Ile Ala His Leu Ile Gln Gly Phe Asn Tyr
465                 470                 475                 480
Lys Thr Pro Asn Asp Glu Pro Leu Asp Met Lys Glu Gly Ala Gly Leu
                485                 490                 495
Thr Ile Arg Lys Val Asn Pro Ile Glu Val Ile Thr Pro Arg Leu
                500                 505                 510
Thr Pro Glu Leu Tyr
        515

<210> SEQ ID NO 6
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E10 G172R Variant

<400> SEQUENCE: 6

Met Val Ser Pro Val Glu Ala Ile Val Gly Leu Val Thr Leu Thr Leu
1               5                   10                  15
Leu Phe Tyr Phe Ile Arg Thr Lys Lys Ser Gln Lys Pro Ser Lys Pro
                20                  25                  30
Leu Pro Pro Lys Ile Pro Gly Gly Trp Pro Val Ile Gly His Leu Phe
                35                  40                  45
Tyr Phe Asp Asp Asp Ser Asp Asp Arg Pro Leu Ala Arg Lys Leu Gly
                50                  55                  60
```

```
Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Ile Lys Asp Cys Phe
                 85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
        130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Arg Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480
```

```
Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
            515

<210> SEQ ID NO 7
<211> LENGTH: 517
<212> TYPE: PRT
<213> ORGANISM: Nicotiana tabacum
<220> FEATURE:
<221> NAME/KEY: VARIANT
<222> LOCATION: (1)...(7)
<223> OTHER INFORMATION: CYP82E10 A344T Variant

<400> SEQUENCE: 7

Met Val Ser Pro Val Glu Ala Ile Val Gly Leu Val Thr Leu Thr Leu
 1               5                  10                  15

Leu Phe Tyr Phe Ile Arg Thr Lys Lys Ser Gln Lys Pro Ser Lys Pro
             20                  25                  30

Leu Pro Pro Lys Ile Pro Gly Gly Trp Pro Val Ile Gly His Leu Phe
         35                  40                  45

Tyr Phe Asp Asp Asp Ser Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Ile Lys Asp Cys Phe
                 85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
        130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
```

```
                305                 310                 315                 320
        Asp Thr Val Ala Leu His Met Asn Trp Gly Met Ala Leu Leu Ile Asn
                        325                 330                 335

Asn Gln His Ala Leu Lys Lys Thr Gln Glu Glu Ile Asp Lys Lys Val
                        340                 345                 350

Gly Lys Asp Arg Trp Val Glu Glu Ser Asp Ile Lys Asp Leu Val Tyr
                        355                 360                 365

Leu Gln Thr Ile Val Lys Glu Val Leu Arg Leu Tyr Pro Pro Gly Pro
                370                 375                 380

Leu Leu Val Pro His Glu Asn Val Glu Asp Cys Val Val Ser Gly Tyr
        385                 390                 395                 400

His Ile Pro Lys Gly Thr Arg Leu Phe Ala Asn Val Met Lys Leu Gln
                        405                 410                 415

Arg Asp Pro Lys Leu Trp Ser Asn Pro Asp Lys Phe Asp Pro Glu Arg
                        420                 425                 430

Phe Phe Ala Ala Asp Ile Asp Phe Arg Gly Gln His Tyr Glu Phe Ile
                        435                 440                 445

Pro Phe Gly Ser Gly Arg Arg Ser Cys Pro Gly Met Thr Tyr Ala Met
                450                 455                 460

Gln Val Glu His Leu Thr Ile Ala His Leu Ile Gln Gly Phe Asn Tyr
        465                 470                 475                 480

Lys Thr Pro Asn Asp Glu Pro Leu Asp Met Lys Glu Gly Ala Gly Leu
                        485                 490                 495

Thr Ile Arg Lys Val Asn Pro Ile Glu Val Val Ile Thr Pro Arg Leu
                        500                 505                 510

Thr Pro Glu Leu Tyr
                515

<210> SEQ ID NO 8
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E10 A410T

<400> SEQUENCE: 8

Met Val Ser Pro Val Glu Ala Ile Val Gly Leu Val Thr Leu Thr Leu
        1               5                   10                  15

Leu Phe Tyr Phe Ile Arg Thr Lys Lys Ser Gln Lys Pro Ser Lys Pro
                        20                  25                  30

Leu Pro Pro Lys Ile Pro Gly Gly Trp Pro Val Ile Gly His Leu Phe
                        35                  40                  45

Tyr Phe Asp Asp Asp Ser Asp Asp Arg Pro Leu Ala Arg Lys Leu Gly
                50                  55                  60

Asp Leu Ala Asp Lys Tyr Gly Pro Val Phe Thr Phe Arg Leu Gly Leu
        65                  70                  75                  80

Pro Leu Val Leu Val Val Ser Ser Tyr Glu Ala Ile Lys Asp Cys Phe
                        85                  90                  95

Ser Thr Asn Asp Ala Ile Phe Ser Asn Arg Pro Ala Phe Leu Tyr Gly
                        100                 105                 110

Glu Tyr Leu Gly Tyr Asn Asn Ala Met Leu Phe Leu Thr Lys Tyr Gly
                        115                 120                 125

Pro Tyr Trp Arg Lys Asn Arg Lys Leu Val Ile Gln Glu Val Leu Cys
                130                 135                 140
```

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
        180                 185                 190

Lys Met Ile Ala Gly Lys Asn Tyr Glu Ser Gly Lys Gly Asp Glu Gln
    195                 200                 205

Val Glu Arg Phe Arg Lys Ala Phe Lys Asp Phe Ile Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
    275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Thr Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 9
<211> LENGTH: 517
<212> TYPE: PRT
<213> ORGANISM: Nicotiana tabacum
<220> FEATURE:

<220> NAME/KEY: VARIANT
<222> LOCATION: (1)...(517)
<223> OTHER INFORMATION: CYP82E10 R417H Variant

<400> SEQUENCE: 9

```
Met Val Ser Pro Val Glu Ala Ile Val Gly Leu Val Thr Leu Thr Leu
 1               5                  10                  15

Leu Phe Tyr Phe Ile Arg Thr Lys Lys Ser Gln Lys Pro Ser Lys Pro
             20                  25                  30

Leu Pro Pro Lys Ile Pro Gly Gly Trp Pro Val Ile Gly His Leu Phe
         35                  40                  45

Tyr Phe Asp Asp Asp Ser Asp Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Ile Lys Asp Cys Phe
                 85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
```

```
                385                 390                 395                 400
His Ile Pro Lys Gly Thr Arg Leu Phe Ala Asn Val Met Lys Leu Gln
            405                 410                 415

His Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
                500                 505                 510

Thr Pro Glu Leu Tyr
            515

<210> SEQ ID NO 10
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E10 P419S Variant

<400> SEQUENCE: 10

Met Val Ser Pro Val Glu Ala Ile Val Gly Leu Val Thr Leu Thr Leu
 1               5                  10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220
```

```
Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Lys Glu
        260                 265                 270

Lys Met Glu Val Asn Ala Glu Gly Asn Glu Gln Asp Phe Ile Asp Val
    275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Ser Asp Ile Lys Asp Leu Val Tyr
        355                 360                 365

Leu Gln Thr Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Ser Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
        450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 11
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E10 G79S Variant

<400> SEQUENCE: 11

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45
```

-continued

```
Tyr Phe Asp Asp Asp Ser Asp Arg Pro Leu Ala Arg Lys Leu Gly
    50              55              60

Asp Leu Ala Asp Lys Tyr Gly Pro Val Phe Thr Phe Arg Leu Ser Leu
65              70              75                          80

Pro Leu Val Leu Val Ser Ser Tyr Glu Ala Ile Lys Asp Cys Phe
                85              90              95

Ser Thr Asn Asp Ala Ile Phe Ser Asn Arg Pro Ala Phe Leu Tyr Gly
            100             105             110

Glu Tyr Leu Gly Tyr Asn Asn Ala Met Leu Phe Leu Thr Lys Tyr Gly
                115             120             125

Pro Tyr Trp Arg Lys Asn Arg Lys Leu Val Ile Gln Glu Val Leu Cys
    130             135             140

Ala Ser Arg Leu Glu Lys Leu Lys His Val Arg Phe Gly Glu Ile Gln
145             150             155             160

Thr Ser Ile Lys Asn Leu Tyr Thr Arg Ile Asp Gly Asn Ser Ser Thr
                165             170             175

Ile Asn Leu Thr Asp Trp Leu Glu Glu Leu Asn Phe Gly Leu Ile Val
            180             185             190

Lys Met Ile Ala Gly Lys Asn Tyr Glu Ser Gly Lys Gly Asp Glu Gln
                195             200             205

Val Glu Arg Phe Arg Lys Ala Phe Lys Asp Phe Ile Ile Leu Ser Met
    210             215             220

Glu Phe Val Leu Trp Asp Ala Phe Pro Ile Pro Leu Phe Lys Trp Val
225             230             235             240

Asp Phe Gln Gly His Val Lys Ala Met Lys Arg Thr Phe Lys Asp Ile
                245             250             255

Asp Ser Val Phe Gln Asn Trp Leu Glu Glu His Val Lys Lys Lys Glu
            260             265             270

Lys Met Glu Val Asn Ala Glu Gly Asn Glu Gln Asp Phe Ile Asp Val
                275             280             285

Val Leu Ser Lys Met Ser Asn Glu Tyr Leu Asp Glu Gly Tyr Ser Arg
    290             295             300

Asp Thr Val Ile Lys Ala Thr Val Phe Ser Leu Val Leu Asp Ala Ala
305             310             315             320

Asp Thr Val Ala Leu His Met Asn Trp Gly Met Ala Leu Leu Ile Asn
                325             330             335

Asn Gln His Ala Leu Lys Lys Ala Gln Glu Glu Ile Asp Lys Lys Val
            340             345             350

Gly Lys Asp Arg Trp Val Glu Glu Ser Asp Ile Lys Asp Leu Val Tyr
                355             360             365

Leu Gln Thr Ile Val Lys Glu Val Leu Arg Leu Tyr Pro Pro Gly Pro
    370             375             380

Leu Leu Val Pro His Glu Asn Val Glu Asp Cys Val Val Ser Gly Tyr
385             390             395             400

His Ile Pro Lys Gly Thr Arg Leu Phe Ala Asn Val Met Lys Leu Gln
                405             410             415

Arg Asp Pro Lys Leu Trp Ser Asn Pro Asp Lys Phe Asp Pro Glu Arg
    420             425             430

Phe Phe Ala Ala Asp Ile Asp Phe Arg Gly Gln His Tyr Glu Phe Ile
                435             440             445

Pro Phe Gly Ser Gly Arg Arg Ser Cys Pro Gly Met Thr Tyr Ala Met
    450             455             460

Gln Val Glu His Leu Thr Ile Ala His Leu Ile Gln Gly Phe Asn Tyr
```

```
                    465                 470                 475                 480
Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
                500                 505                 510

Thr Pro Glu Leu Tyr
                515

<210> SEQ ID NO 12
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E10 P107S Variant

<400> SEQUENCE: 12

Met Val Ser Pro Val Glu Ala Ile Val Gly Leu Val Thr Leu Thr Leu
  1               5                  10                  15

Leu Phe Tyr Phe Ile Arg Thr Lys Lys Ser Gln Lys Pro Ser Lys Pro
                 20                  25                  30

Leu Pro Pro Lys Ile Pro Gly Gly Trp Pro Val Ile Gly His Leu Phe
             35                  40                  45

Tyr Phe Asp Asp Ser Asp Asp Arg Pro Leu Ala Arg Lys Leu Gly
     50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Ile Lys Asp Cys Phe
                 85                  90                  95

Ser Thr Asn Asp Ala Ile Phe Ser Asn Arg Ser Ala Phe Leu Tyr Gly
                100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
        130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300
```

-continued

```
Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
            340                 345                 350

Gly Lys Asp Arg Trp Val Glu Glu Ser Asp Ile Lys Asp Leu Val Tyr
                355                 360                 365

Leu Gln Thr Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
                435                 440                 445

Pro Phe Gly Ser Gly Arg Arg Ser Cys Pro Gly Met Thr Tyr Ala Met
            450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
            515

<210> SEQ ID NO 13
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E10 P381S Variant

<400> SEQUENCE: 13

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Ser Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125
```

Pro Tyr Trp Arg Lys Asn Arg Lys Leu Val Ile Gln Glu Val Leu Cys
            130                 135                 140
Ala Ser Arg Leu Glu Lys Leu Lys His Val Arg Phe Gly Glu Ile Gln
145                 150                 155                 160
Thr Ser Ile Lys Asn Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Arg Lys Ala Phe Lys Asp Phe Ile Ile Leu Ser Met
210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Lys Glu
            260                 265                 270
Lys Met Glu Val Asn Ala Glu Gly Asn Glu Gln Asp Phe Ile Asp Val
        275                 280                 285
Val Leu Ser Lys Met Ser Asn Glu Tyr Leu Asp Glu Gly Tyr Ser Arg
290                 295                 300
Asp Thr Val Ile Lys Ala Thr Val Phe Ser Leu Val Leu Asp Ala Ala
305                 310                 315                 320
Asp Thr Val Ala Leu His Met Asn Trp Gly Met Ala Leu Leu Ile Asn
                325                 330                 335
Asn Gln His Ala Leu Lys Lys Ala Gln Glu Glu Ile Asp Lys Lys Val
            340                 345                 350
Gly Lys Asp Arg Trp Val Glu Glu Ser Asp Ile Lys Asp Leu Val Tyr
        355                 360                 365
Leu Gln Thr Ile Val Lys Glu Val Leu Arg Leu Tyr Ser Pro Gly Pro
370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asn Pro Asp Lys Phe Asp Pro Glu Arg
            420                 425                 430
Phe Phe Ala Ala Asp Ile Asp Phe Arg Gly Gln His Tyr Glu Phe Ile
        435                 440                 445
Pro Phe Gly Ser Gly Arg Arg Ser Cys Pro Gly Met Thr Tyr Ala Met
450                 455                 460
Gln Val Glu His Leu Thr Ile Ala His Leu Ile Gln Gly Phe Asn Tyr
465                 470                 475                 480
Lys Thr Pro Asn Asp Glu Pro Leu Asp Met Lys Glu Gly Ala Gly Leu
                485                 490                 495
Thr Ile Arg Lys Val Asn Pro Ile Glu Val Val Ile Thr Pro Arg Leu
            500                 505                 510
Thr Pro Glu Leu Tyr
        515

<210> SEQ ID NO 14
<211> LENGTH: 517
<212> TYPE: PRT

<213> ORGANISM: Nicotiana tabacum

<400> SEQUENCE: 14

```
Met Leu Ser Pro Ile Glu Ala Ile Val Gly Leu Val Thr Phe Thr Phe
  1               5                  10                  15
Leu Phe Phe Phe Leu Trp Thr Lys Lys Ser Gln Lys Pro Ser Lys Pro
             20                  25                  30
Leu Pro Pro Lys Ile Pro Gly Gly Trp Pro Val Ile Gly His Leu Phe
         35                  40                  45
His Phe Asn Asp Asp Gly Asp Asp Arg Pro Leu Ala Arg Lys Leu Gly
     50                  55                  60
Asp Leu Ala Asp Lys Tyr Gly Pro Val Phe Thr Phe Arg Leu Gly Leu
 65                  70                  75                  80
Pro Leu Val Leu Val Val Ser Ser Tyr Glu Ala Val Lys Asp Cys Phe
                 85                  90                  95
Ser Thr Asn Asp Ala Ile Phe Ser Asn Arg Pro Ala Phe Leu Tyr Gly
            100                 105                 110
Asp Tyr Leu Gly Tyr Asn Asn Ala Met Leu Phe Leu Ala Asn Tyr Gly
        115                 120                 125
Pro Tyr Trp Arg Lys Asn Arg Lys Leu Val Ile Gln Glu Val Leu Ser
    130                 135                 140
Ala Ser Arg Leu Glu Lys Phe Lys His Val Arg Phe Ala Arg Ile Gln
145                 150                 155                 160
Ala Ser Ile Lys Asn Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Lys Lys Ala Phe Lys Asp Phe Met Ile Leu Ser Met
    210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Ile Asn Lys Arg Glu
            260                 265                 270
Lys Met Glu Val Asn Ala Glu Gly Asn Glu Gln Asp Phe Ile Asp Val
        275                 280                 285
Val Leu Ser Lys Met Ser Asn Glu Tyr Leu Gly Glu Gly Tyr Ser Arg
    290                 295                 300
Asp Thr Val Ile Lys Ala Thr Val Phe Ser Leu Val Leu Asp Ala Ala
305                 310                 315                 320
Asp Thr Val Ala Leu His Ile Asn Trp Gly Met Ala Leu Leu Ile Asn
                325                 330                 335
Asn Gln Lys Ala Leu Thr Lys Ala Gln Glu Glu Ile Asp Thr Lys Val
            340                 345                 350
Gly Lys Asp Arg Trp Val Glu Glu Ser Asp Ile Lys Asp Leu Val Tyr
        355                 360                 365
Leu Gln Ala Ile Val Lys Glu Val Leu Arg Leu Tyr Pro Pro Gly Pro
    370                 375                 380
Leu Leu Val Pro His Glu Asn Val Glu Asp Cys Val Val Ser Gly Tyr
385                 390                 395                 400
```

```
His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Arg Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 15
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E4 P38L Variant

<400> SEQUENCE: 15

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Leu Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
```

```
                225                 230                 235                 240
Asp Phe Gln Gly His Val Lys Ala Met Lys Arg Thr Phe Lys Asp Ile
            245                 250                 255
Asp Ser Val Phe Gln Asn Trp Leu Glu Glu His Ile Asn Lys Arg Glu
            260                 265                 270
Lys Met Glu Val Asn Ala Glu Gly Asn Glu Gln Asp Phe Ile Asp Val
            275                 280                 285
Val Leu Ser Lys Met Ser Asn Glu Tyr Leu Gly Glu Gly Tyr Ser Arg
290                 295                 300
Asp Thr Val Ile Lys Ala Thr Val Phe Ser Leu Val Leu Asp Ala Ala
305                 310                 315                 320
Asp Thr Val Ala Leu His Ile Asn Trp Gly Met Ala Leu Leu Ile Asn
            325                 330                 335
Asn Gln Lys Ala Leu Thr Lys Ala Gln Glu Glu Ile Asp Thr Lys Val
            340                 345                 350
Gly Lys Asp Arg Trp Val Glu Glu Ser Asp Ile Lys Asp Leu Val Tyr
            355                 360                 365
Leu Gln Ala Ile Val Lys Glu Val Leu Arg Leu Tyr Pro Pro Gly Pro
370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
            405                 410                 415
Arg Asp Pro Lys Leu Trp Ser Asp Pro Asp Thr Phe Asp Pro Glu Arg
            420                 425                 430
Phe Ile Ala Thr Asp Ile Asp Phe Arg Gly Gln Tyr Tyr Lys Tyr Ile
            435                 440                 445
Pro Phe Gly Ser Gly Arg Arg Ser Cys Pro Gly Met Thr Tyr Ala Leu
            450                 455                 460
Gln Val Glu His Leu Thr Met Ala His Leu Ile Gln Gly Phe Asn Tyr
465                 470                 475                 480
Arg Thr Pro Asn Asp Glu Pro Leu Asp Met Lys Glu Gly Ala Gly Ile
            485                 490                 495
Thr Ile Arg Lys Val Asn Pro Val Glu Leu Ile Ile Ala Pro Arg Leu
            500                 505                 510
Ala Pro Glu Leu Tyr
            515

<210> SEQ ID NO 16
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E4 D171N Variant

<400> SEQUENCE: 16

Met Leu Ser Pro Ile Glu Ala Ile Val Gly Leu Val Thr Phe Thr Phe
1               5                   10                  15
Leu Phe Phe Phe Leu Trp Thr Lys Lys Ser Gln Lys Pro Ser Lys Pro
            20                  25                  30
Leu Pro Pro Lys Ile Pro Gly Gly Trp Pro Val Ile Gly His Leu Phe
            35                  40                  45
His Phe Asn Asp Asp Gly Asp Asp Arg Pro Leu Ala Arg Lys Leu Gly
        50                  55                  60
```

```
Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Val Lys Asp Cys Phe
             85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asn Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
            325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480
```

```
Arg Thr Pro Asn Asp Glu Pro Leu Asp Met Lys Glu Gly Ala Gly Ile
                485             490             495

Thr Ile Arg Lys Val Asn Pro Val Glu Leu Ile Ile Ala Pro Arg Leu
        500             505             510

Ala Pro Glu Leu Tyr
        515

<210> SEQ ID NO 17
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E4 E201K Variant

<400> SEQUENCE: 17

Met Leu Ser Pro Ile Glu Ala Ile Val Gly Leu Val Thr Phe Thr Phe
 1               5                  10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
     50                  55                  60

Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Lys Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
        290                 295                 300

Asp Thr Val Ile Lys Ala Thr Val Phe Ser Leu Val Leu Asp Ala Ala
```

```
                305                 310                 315                 320
Asp Thr Val Ala Leu His Ile Asn Trp Gly Met Ala Leu Leu Ile Asn
                    325                 330                 335

Asn Gln Lys Ala Leu Thr Lys Ala Gln Glu Glu Ile Asp Thr Lys Val
                340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Leu Ile Ile Ala Pro Arg Leu
            500                 505                 510

Ala Pro Glu Leu Tyr
        515

<210> SEQ ID NO 18
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E4 R169Q Variant

<400> SEQUENCE: 18

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140
```

```
Ala Ser Arg Leu Glu Lys Phe Lys His Val Arg Phe Ala Arg Ile Gln
145                 150                 155                 160

Ala Ser Ile Lys Asn Leu Tyr Thr Gln Ile Asp Gly Asn Ser Ser Thr
            165                 170                 175

Ile Asn Leu Thr Asp Trp Leu Glu Glu Leu Asn Phe Gly Leu Ile Val
        180                 185                 190

Lys Met Ile Ala Gly Lys Asn Tyr Glu Ser Gly Lys Gly Asp Glu Gln
    195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
        260                 265                 270

Lys Met Glu Val Asn Ala Glu Gly Asn Glu Gln Asp Phe Ile Asp Val
    275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
            325                 330                 335

Asn Gln Lys Ala Leu Thr Lys Ala Gln Glu Glu Ile Asp Thr Lys Val
        340                 345                 350

Gly Lys Asp Arg Trp Val Glu Glu Ser Asp Ile Lys Asp Leu Val Tyr
    355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg
        420                 425                 430

Phe Ile Ala Thr Asp Ile Asp Phe Arg Gly Gln Tyr Tyr Lys Tyr Ile
    435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
        500                 505                 510

Ala Pro Glu Leu Tyr
        515

<210> SEQ ID NO 19
<211> LENGTH: 517
<212> TYPE: PRT
<213> ORGANISM: Nicotiana tabacum
<220> FEATURE:
```

-continued

```
<221> NAME/KEY: VARIANT
<222> LOCATION: (1)...(517)
<223> OTHER INFORMATION: CYP82E4 G459R Variant

<400> SEQUENCE: 19
```

| | | | | | | | | | | | | | | | |
|---|---|---|---|---|---|---|---|---|---|---|---|---|---|---|---|
| Met | Leu | Ser | Pro | Ile | Glu | Ala | Ile | Val | Gly | Leu | Val | Thr | Phe | Thr | Phe |
| 1 | | | | 5 | | | | | 10 | | | | | 15 | |
| Leu | Phe | Phe | Phe | Leu | Trp | Thr | Lys | Lys | Ser | Gln | Lys | Pro | Ser | Lys | Pro |
| | | | 20 | | | | | 25 | | | | | 30 | | |
| Leu | Pro | Pro | Lys | Ile | Pro | Gly | Gly | Trp | Pro | Val | Ile | Gly | His | Leu | Phe |
| | | 35 | | | | | 40 | | | | | 45 | | | |
| His | Phe | Asn | Asp | Asp | Gly | Asp | Asp | Arg | Pro | Leu | Ala | Arg | Lys | Leu | Gly |
| | 50 | | | | | 55 | | | | | 60 | | | | |
| Asp | Leu | Ala | Asp | Lys | Tyr | Gly | Pro | Val | Phe | Thr | Phe | Arg | Leu | Gly | Leu |
| 65 | | | | | 70 | | | | | 75 | | | | | 80 |
| Pro | Leu | Val | Leu | Val | Val | Ser | Ser | Tyr | Glu | Ala | Val | Lys | Asp | Cys | Phe |
| | | | | 85 | | | | | 90 | | | | | 95 | |
| Ser | Thr | Asn | Asp | Ala | Ile | Phe | Ser | Asn | Arg | Pro | Ala | Phe | Leu | Tyr | Gly |
| | | | 100 | | | | | 105 | | | | | 110 | | |
| Asp | Tyr | Leu | Gly | Tyr | Asn | Asn | Ala | Met | Leu | Phe | Leu | Ala | Asn | Tyr | Gly |
| | | | 115 | | | | | 120 | | | | | 125 | | |
| Pro | Tyr | Trp | Arg | Lys | Asn | Arg | Lys | Leu | Val | Ile | Gln | Glu | Val | Leu | Ser |
| | | 130 | | | | | 135 | | | | | 140 | | | |
| Ala | Ser | Arg | Leu | Glu | Lys | Phe | Lys | His | Val | Arg | Phe | Ala | Arg | Ile | Gln |
| 145 | | | | | 150 | | | | | 155 | | | | | 160 |
| Ala | Ser | Ile | Lys | Asn | Leu | Tyr | Thr | Arg | Ile | Asp | Gly | Asn | Ser | Ser | Thr |
| | | | | 165 | | | | | 170 | | | | | 175 | |
| Ile | Asn | Leu | Thr | Asp | Trp | Leu | Glu | Glu | Leu | Asn | Phe | Gly | Leu | Ile | Val |
| | | | 180 | | | | | 185 | | | | | 190 | | |
| Lys | Met | Ile | Ala | Gly | Lys | Asn | Tyr | Glu | Ser | Gly | Lys | Gly | Asp | Glu | Gln |
| | | 195 | | | | | 200 | | | | | 205 | | | |
| Val | Glu | Arg | Phe | Lys | Lys | Ala | Phe | Lys | Asp | Phe | Met | Ile | Leu | Ser | Met |
| | 210 | | | | | 215 | | | | | 220 | | | | |
| Glu | Phe | Val | Leu | Trp | Asp | Ala | Phe | Pro | Ile | Pro | Leu | Phe | Lys | Trp | Val |
| 225 | | | | | 230 | | | | | 235 | | | | | 240 |
| Asp | Phe | Gln | Gly | His | Val | Lys | Ala | Met | Lys | Arg | Thr | Phe | Lys | Asp | Ile |
| | | | | 245 | | | | | 250 | | | | | 255 | |
| Asp | Ser | Val | Phe | Gln | Asn | Trp | Leu | Glu | Glu | His | Ile | Asn | Lys | Arg | Glu |
| | | | 260 | | | | | 265 | | | | | 270 | | |
| Lys | Met | Glu | Val | Asn | Ala | Glu | Gly | Asn | Glu | Gln | Asp | Phe | Ile | Asp | Val |
| | | 275 | | | | | 280 | | | | | 285 | | | |
| Val | Leu | Ser | Lys | Met | Ser | Asn | Glu | Tyr | Leu | Gly | Glu | Gly | Tyr | Ser | Arg |
| | 290 | | | | | 295 | | | | | 300 | | | | |
| Asp | Thr | Val | Ile | Lys | Ala | Thr | Val | Phe | Ser | Leu | Val | Leu | Asp | Ala | Ala |
| 305 | | | | | 310 | | | | | 315 | | | | | 320 |
| Asp | Thr | Val | Ala | Leu | His | Ile | Asn | Trp | Gly | Met | Ala | Leu | Leu | Ile | Asn |
| | | | | 325 | | | | | 330 | | | | | 335 | |
| Asn | Gln | Lys | Ala | Leu | Thr | Lys | Ala | Gln | Glu | Glu | Ile | Asp | Thr | Lys | Val |
| | | | 340 | | | | | 345 | | | | | 350 | | |
| Gly | Lys | Asp | Arg | Trp | Val | Glu | Ser | Asp | Ile | Lys | Asp | Leu | Val | Tyr | |
| | | 355 | | | | | 360 | | | | | 365 | | | |
| Leu | Gln | Ala | Ile | Val | Lys | Glu | Val | Leu | Arg | Leu | Tyr | Pro | Pro | Gly | Pro |
| | 370 | | | | | 375 | | | | | 380 | | | | |
| Leu | Leu | Val | Pro | His | Glu | Asn | Val | Glu | Asp | Cys | Val | Val | Ser | Gly | Tyr |

```
385                 390                 395                 400
His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Arg Met Thr Tyr Ala Leu
            450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
            500                 505                 510

Ala Pro Glu Leu Tyr
            515

<210> SEQ ID NO 20
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E4 T427I Variant

<400> SEQUENCE: 20

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
            85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220
```

```
Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
        260                 265                 270

Lys Met Glu Val Asn Ala Glu Gly Asn Glu Gln Asp Phe Ile Asp Val
    275                 280                 285

Val Leu Ser Lys Met Ser Asn Glu Tyr Leu Gly Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Ile Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
            515

<210> SEQ ID NO 21
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E4 V376M Variant

<400> SEQUENCE: 21

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45
```

```
His Phe Asn Asp Asp Gly Asp Asp Arg Pro Leu Ala Arg Lys Leu Gly
    50              55                  60
Asp Leu Ala Asp Lys Tyr Gly Pro Val Phe Thr Phe Arg Leu Gly Leu
65              70                  75                  80
Pro Leu Val Leu Val Val Ser Ser Tyr Glu Ala Val Lys Asp Cys Phe
                85                  90                  95
Ser Thr Asn Asp Ala Ile Phe Ser Asn Arg Pro Ala Phe Leu Tyr Gly
            100                 105                 110
Asp Tyr Leu Gly Tyr Asn Asn Ala Met Leu Phe Leu Ala Asn Tyr Gly
                115                 120                 125
Pro Tyr Trp Arg Lys Asn Arg Lys Leu Val Ile Gln Glu Val Leu Ser
    130                 135                 140
Ala Ser Arg Leu Glu Lys Phe Lys His Val Arg Phe Ala Arg Ile Gln
145                 150                 155                 160
Ala Ser Ile Lys Asn Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
                180                 185                 190
Lys Met Ile Ala Gly Lys Asn Tyr Glu Ser Gly Lys Gly Asp Glu Gln
            195                 200                 205
Val Glu Arg Phe Lys Lys Ala Phe Lys Asp Phe Met Ile Leu Ser Met
    210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
            245                 250                 255
Asp Ser Val Phe Gln Asn Trp Leu Glu Glu His Ile Asn Lys Arg Glu
            260                 265                 270
Lys Met Glu Val Asn Ala Glu Gly Asn Glu Gln Asp Phe Ile Asp Val
            275                 280                 285
Val Leu Ser Lys Met Ser Asn Glu Tyr Leu Gly Glu Gly Tyr Ser Arg
            290                 295                 300
Asp Thr Val Ile Lys Ala Thr Val Phe Ser Leu Val Leu Asp Ala Ala
305                 310                 315                 320
Asp Thr Val Ala Leu His Ile Asn Trp Gly Met Ala Leu Leu Ile Asn
                325                 330                 335
Asn Gln Lys Ala Leu Thr Lys Ala Gln Glu Ile Asp Thr Lys Val
            340                 345                 350
Gly Lys Asp Arg Trp Val Glu Glu Ser Asp Ile Lys Asp Leu Val Tyr
            355                 360                 365
Leu Gln Ala Ile Val Lys Glu Met Leu Arg Leu Tyr Pro Pro Gly Pro
    370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asp Pro Asp Thr Phe Asp Pro Glu Arg
            420                 425                 430
Phe Ile Ala Thr Asp Ile Asp Phe Arg Gly Gln Tyr Tyr Lys Tyr Ile
                435                 440                 445
Pro Phe Gly Ser Gly Arg Arg Ser Cys Pro Gly Met Thr Tyr Ala Leu
450                 455                 460
Gln Val Glu His Leu Thr Met Ala His Leu Ile Gln Gly Phe Asn Tyr
```

```
                 465                 470                 475                 480
Arg Thr Pro Asn Asp Glu Pro Leu Asp Met Lys Glu Gly Ala Gly Ile
                    485                 490                 495

Thr Ile Arg Lys Val Asn Pro Val Glu Leu Ile Ile Ala Pro Arg Leu
                500                 505                 510

Ala Pro Glu Leu Tyr
            515

<210> SEQ ID NO 22
<211> LENGTH: 328
<212> TYPE: PRT
<213> ORGANISM: Nicotiana tabacum
<220> FEATURE:
<221> NAME/KEY: VARIANT
<222> LOCATION: (1)...(328)
<223> OTHER INFORMATION: CYP82E4 W329Stop Variant

<400> SEQUENCE: 22

Met Leu Ser Pro Ile Glu Ala Ile Val Gly Leu Val Thr Phe Thr Phe
  1               5                  10                  15

Leu Phe Phe Phe Leu Trp Thr Lys Lys Ser Gln Lys Pro Ser Lys Pro
                 20                  25                  30

Leu Pro Pro Lys Ile Pro Gly Gly Trp Pro Val Ile Gly His Leu Phe
             35                  40                  45

His Phe Asn Asp Asp Gly Asp Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
        290                 295                 300
```

```
Asp Thr Val Ile Lys Ala Thr Val Phe Ser Leu Val Leu Asp Ala Ala
305                 310                 315                 320

Asp Thr Val Ala Leu His Ile Asn
                325

<210> SEQ ID NO 23
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E4 K364N Variant

<400> SEQUENCE: 23

Met Leu Ser Pro Ile Glu Ala Ile Val Gly Leu Val Thr Phe Thr Phe
  1               5                  10                  15

Leu Phe Phe Phe Leu Trp Thr Lys Lys Ser Gln Lys Pro Ser Lys Pro
                 20                  25                  30

Leu Pro Pro Lys Ile Pro Gly Gly Trp Pro Val Ile Gly His Leu Phe
             35                  40                  45

His Phe Asn Asp Asp Gly Asp Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
                115                 120                 125

Pro Tyr Trp Arg Lys Asn Arg Lys Leu Val Ile Gln Glu Val Leu Ser
                130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
                195                 200                 205

Val Glu Arg Phe Lys Lys Ala Phe Lys Asp Phe Met Ile Leu Ser Met
                210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
                260                 265                 270

Lys Met Glu Val Asn Ala Glu Gly Asn Glu Gln Asp Phe Ile Asp Val
                275                 280                 285

Val Leu Ser Lys Met Ser Asn Glu Tyr Leu Gly Glu Gly Tyr Ser Arg
                290                 295                 300

Asp Thr Val Ile Lys Ala Thr Val Phe Ser Leu Val Leu Asp Ala Ala
305                 310                 315                 320
```

```
Asp Thr Val Ala Leu His Ile Asn Trp Gly Met Ala Leu Leu Ile Asn
                    325                 330                 335

Asn Gln Lys Ala Leu Thr Lys Ala Gln Glu Ile Asp Thr Lys Val
            340                 345                 350

Gly Lys Asp Arg Trp Val Glu Glu Ser Asp Ile Asn Asp Leu Val Tyr
            355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
            515

<210> SEQ ID NO 24
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E4 P381S Variant

<400> SEQUENCE: 24

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
    115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
```

```
                145                 150                 155                 160
        Ala Ser Ile Lys Asn Leu Tyr Thr Arg Ile Asp Gly Asn Ser Ser Thr
                        165                 170                 175

Ile Asn Leu Thr Asp Trp Leu Glu Glu Leu Asn Phe Gly Leu Ile Val
                        180                 185                 190

Lys Met Ile Ala Gly Lys Asn Tyr Glu Ser Gly Lys Gly Asp Glu Gln
                        195                 200                 205

Val Glu Arg Phe Lys Lys Ala Phe Lys Asp Phe Met Ile Leu Ser Met
                210                 215                 220

Glu Phe Val Leu Trp Asp Ala Phe Pro Ile Pro Leu Phe Lys Trp Val
        225                 230                 235                 240

Asp Phe Gln Gly His Val Lys Ala Met Lys Arg Thr Phe Lys Asp Ile
                        245                 250                 255

Asp Ser Val Phe Gln Asn Trp Leu Glu Glu His Ile Asn Lys Arg Glu
                        260                 265                 270

Lys Met Glu Val Asn Ala Glu Gly Asn Glu Gln Asp Phe Ile Asp Val
                        275                 280                 285

Val Leu Ser Lys Met Ser Asn Glu Tyr Leu Gly Glu Gly Tyr Ser Arg
                290                 295                 300

Asp Thr Val Ile Lys Ala Thr Val Phe Ser Leu Val Leu Asp Ala Ala
        305                 310                 315                 320

Asp Thr Val Ala Leu His Ile Asn Trp Gly Met Ala Leu Leu Ile Asn
                        325                 330                 335

Asn Gln Lys Ala Leu Thr Lys Ala Gln Glu Glu Ile Asp Thr Lys Val
                        340                 345                 350

Gly Lys Asp Arg Trp Val Glu Glu Ser Asp Ile Lys Asp Leu Val Tyr
                        355                 360                 365

Leu Gln Ala Ile Val Lys Glu Val Leu Arg Leu Tyr Ser Pro Gly Pro
                370                 375                 380

Leu Leu Val Pro His Glu Asn Val Glu Asp Cys Val Val Ser Gly Tyr
        385                 390                 395                 400

His Ile Pro Lys Gly Thr Arg Leu Phe Ala Asn Val Met Lys Leu Gln
                        405                 410                 415

Arg Asp Pro Lys Leu Trp Ser Asp Pro Asp Thr Phe Asp Pro Glu Arg
                        420                 425                 430

Phe Ile Ala Thr Asp Ile Asp Phe Arg Gly Gln Tyr Tyr Lys Tyr Ile
                        435                 440                 445

Pro Phe Gly Ser Gly Arg Arg Ser Cys Pro Gly Met Thr Tyr Ala Leu
                450                 455                 460

Gln Val Glu His Leu Thr Met Ala His Leu Ile Gln Gly Phe Asn Tyr
        465                 470                 475                 480

Arg Thr Pro Asn Asp Glu Pro Leu Asp Met Lys Glu Gly Ala Gly Ile
                        485                 490                 495

Thr Ile Arg Lys Val Asn Pro Val Glu Leu Ile Ile Ala Pro Arg Leu
                        500                 505                 510

Ala Pro Glu Leu Tyr
                515

<210> SEQ ID NO 25
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
```

<223> OTHER INFORMATION: CYP82E4 P458S Variant

<400> SEQUENCE: 25

```
Met Leu Ser Pro Ile Glu Ala Ile Val Gly Leu Val Thr Phe Thr Phe
 1               5                  10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400
```

```
His Ile Pro Lys Gly Thr Arg Leu Phe Ala Asn Val Met Lys Leu Gln
                405                 410                 415
Arg Asp Pro Lys Leu Trp Ser Asp Pro Asp Thr Phe Asp Pro Glu Arg
            420                 425                 430
Phe Ile Ala Thr Asp Ile Asp Phe Arg Gly Gln Tyr Tyr Lys Tyr Ile
        435                 440                 445
Pro Phe Gly Ser Gly Arg Arg Ser Cys Ser Gly Met Thr Tyr Ala Leu
    450                 455                 460
Gln Val Glu His Leu Thr Met Ala His Leu Ile Gln Gly Phe Asn Tyr
465                 470                 475                 480
Arg Thr Pro Asn Asp Glu Pro Leu Asp Met Lys Glu Gly Ala Gly Ile
                485                 490                 495
Thr Ile Arg Lys Val Asn Pro Val Glu Leu Ile Ile Ala Pro Arg Leu
            500                 505                 510
Ala Pro Glu Leu Tyr
        515

<210> SEQ ID NO 26
<211> LENGTH: 517
<212> TYPE: PRT
<213> ORGANISM: Nicotiana tabacum

<400> SEQUENCE: 26

Met Val Ser Pro Val Glu Ala Ile Val Gly Leu Val Thr Leu Thr Leu
1               5                   10                  15
Leu Phe Tyr Phe Leu Trp Pro Lys Lys Phe Gln Ile Pro Ser Lys Pro
            20                  25                  30
Leu Pro Pro Lys Ile Pro Gly Gly Trp Pro Val Ile Gly His Leu Phe
        35                  40                  45
Tyr Phe Asp Asp Asp Gly Asp Asp Arg Pro Leu Ala Arg Lys Leu Gly
    50                  55                  60
Asp Leu Ala Asp Lys Tyr Gly Pro Val Phe Thr Phe Arg Leu Gly Leu
65                  70                  75                  80
Pro Leu Val Leu Val Val Ser Ser Tyr Glu Ala Val Lys Asp Cys Phe
                85                  90                  95
Ser Thr Asn Asp Ala Ile Phe Ser Asn Arg Pro Ala Phe Leu Tyr Gly
            100                 105                 110
Glu Tyr Leu Gly Tyr Ser Asn Ala Met Leu Phe Leu Thr Lys Tyr Gly
        115                 120                 125
Pro Tyr Trp Arg Lys Asn Arg Lys Leu Val Ile Gln Glu Val Leu Ser
    130                 135                 140
Ala Ser Arg Leu Glu Lys Leu Lys His Val Arg Phe Gly Lys Ile Gln
145                 150                 155                 160
Thr Ser Ile Lys Ser Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Arg Lys Ala Phe Lys Asp Phe Ile Ile Leu Ser Met
    210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
```

-continued

```
Asp Ser Val Phe Gln Asn Trp Leu Glu Glu His Val Lys Lys Arg Glu
                260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 27
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E5 P72L Variant

<400> SEQUENCE: 27

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Leu Val Phe Thr Phe Arg Leu Gly Leu
65                  70                  75                  80
```

-continued

```
Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
            450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
```

```
                    500                 505                 510
Ala Pro Glu Leu Tyr
        515

<210> SEQ ID NO 28
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E5 L143F Variant

<400> SEQUENCE: 28

Met Val Ser Pro Val Glu Ala Ile Val Gly Leu Val Thr Leu Thr Leu
  1               5                  10                  15

Leu Phe Tyr Phe Leu Trp Pro Lys Lys Phe Gln Ile Pro Ser Lys Pro
             20                  25                  30

Leu Pro Pro Lys Ile Pro Gly Gly Trp Pro Val Ile Gly His Leu Phe
         35                  40                  45

Tyr Phe Asp Asp Asp Gly Asp Asp Arg Pro Leu Ala Arg Lys Leu Gly
     50                  55                  60

Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
             100                 105                 110

Glu Tyr Leu Gly Tyr Ser Asn Ala Met Leu Phe Leu Thr Lys Tyr Gly
         115                 120                 125

Pro Tyr Trp Arg Lys Asn Arg Lys Leu Val Ile Gln Glu Val Phe Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335
```

```
Asn Gln His Ala Leu Lys Lys Ala Gln Glu Ile Asp Lys Lys Val
                340                 345                 350

Gly Lys Glu Arg Trp Val Glu Ser Asp Ile Lys Asp Leu Val Tyr
            355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 29
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E5 S174L Variant

<400> SEQUENCE: 29

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160
```

```
Thr Ser Ile Lys Ser Leu Tyr Thr Arg Ile Asp Gly Asn Leu Ser Thr
            165                 170                 175
Ile Asn Leu Thr Asp Trp Leu Glu Glu Leu Asn Phe Gly Leu Ile Val
        180                 185                 190
Lys Met Ile Ala Gly Lys Asn Tyr Glu Ser Gly Lys Gly Asp Glu Gln
    195                 200                 205
Val Glu Arg Phe Arg Lys Ala Phe Lys Asp Phe Ile Ile Leu Ser Met
210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Arg Glu
            260                 265                 270
Lys Met Glu Val Asn Ala Gln Gly Asn Glu Gln Asp Phe Ile Asp Val
        275                 280                 285
Val Leu Ser Lys Met Ser Asn Glu Tyr Leu Asp Glu Gly Tyr Ser Arg
    290                 295                 300
Asp Thr Val Ile Lys Ala Thr Val Phe Ser Leu Val Leu Asp Ala Ala
305                 310                 315                 320
Asp Thr Val Ala Leu His Met Asn Trp Gly Met Ala Leu Leu Ile Asn
                325                 330                 335
Asn Gln His Ala Leu Lys Lys Ala Gln Glu Ile Asp Lys Lys Val
            340                 345                 350
Gly Lys Glu Arg Trp Val Glu Glu Ser Asp Ile Lys Asp Leu Val Tyr
        355                 360                 365
Leu Gln Ala Ile Val Lys Glu Val Leu Arg Leu Tyr Pro Pro Gly Pro
    370                 375                 380
Leu Leu Val Pro His Glu Asn Val Glu Asp Cys Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asn Pro Asp Lys Phe Asp Pro Glu Arg
            420                 425                 430
Phe Phe Ala Asp Asp Ile Asp Tyr Arg Gly Gln His Tyr Glu Phe Ile
        435                 440                 445
Pro Phe Gly Ser Gly Arg Arg Ser Cys Pro Gly Met Thr Tyr Ala Leu
    450                 455                 460
Gln Ala Glu His Leu Thr Ile Ala His Leu Ile Gln Gly Phe Asn Tyr
465                 470                 475                 480
Lys Thr Pro Asn Asp Glu Pro Leu Asp Met Lys Glu Gly Ala Gly Leu
                485                 490                 495
Thr Ile Arg Lys Val Asn Pro Val Glu Val Thr Ile Thr Ala Arg Leu
            500                 505                 510
Ala Pro Glu Leu Tyr
        515

<210> SEQ ID NO 30
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E5 M224I Variant
```

```
<400> SEQUENCE: 30

Met Val Ser Pro Val Glu Ala Ile Val Gly Leu Val Thr Leu Thr Leu
  1               5                  10                  15

Leu Phe Tyr Phe Leu Trp Pro Lys Lys Phe Gln Ile Pro Ser Lys Pro
             20                  25                  30

Leu Pro Pro Lys Ile Pro Gly Gly Trp Pro Val Ile Gly His Leu Phe
         35                  40                  45

Tyr Phe Asp Asp Asp Gly Asp Asp Arg Pro Leu Ala Arg Lys Leu Gly
     50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Ile
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415
```

-continued

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 31
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E5 P235S Variant

<400> SEQUENCE: 31

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
            85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Pro Ile Ser Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
        260                 265                 270

Lys Met Glu Val Asn Ala Gln Gly Asn Glu Gln Asp Phe Ile Asp Val
    275                 280                 285

Val Leu Ser Lys Met Ser Asn Glu Tyr Leu Asp Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 32
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E5 A410V Variant

<400> SEQUENCE: 32

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu

-continued

```
            65                  70                  75                  80
        Pro Leu Val Leu Val Ser Ser Tyr Glu Ala Val Lys Asp Cys Phe
                        85                  90                  95
        Ser Thr Asn Asp Ala Ile Phe Ser Asn Arg Pro Ala Phe Leu Tyr Gly
                    100                 105                 110
        Glu Tyr Leu Gly Tyr Ser Asn Ala Met Leu Phe Leu Thr Lys Tyr Gly
                    115                 120                 125
        Pro Tyr Trp Arg Lys Asn Arg Lys Leu Val Ile Gln Glu Val Leu Ser
                    130                 135                 140
        Ala Ser Arg Leu Glu Lys Leu Lys His Val Arg Phe Gly Lys Ile Gln
        145                 150                 155                 160
        Thr Ser Ile Lys Ser Leu Tyr Thr Arg Ile Asp Gly Asn Ser Ser Thr
                        165                 170                 175
        Ile Asn Leu Thr Asp Trp Leu Glu Glu Leu Asn Phe Gly Leu Ile Val
                    180                 185                 190
        Lys Met Ile Ala Gly Lys Asn Tyr Glu Ser Gly Lys Gly Asp Glu Gln
                    195                 200                 205
        Val Glu Arg Phe Arg Lys Ala Phe Lys Asp Phe Ile Ile Leu Ser Met
        210                 215                 220
        Glu Phe Val Leu Trp Asp Ala Phe Pro Ile Pro Leu Phe Lys Trp Val
        225                 230                 235                 240
        Asp Phe Gln Gly His Val Lys Ala Met Lys Arg Thr Phe Lys Asp Ile
                        245                 250                 255
        Asp Ser Val Phe Gln Asn Trp Leu Glu Glu His Val Lys Lys Arg Glu
                    260                 265                 270
        Lys Met Glu Val Asn Ala Gln Gly Asn Glu Gln Asp Phe Ile Asp Val
                    275                 280                 285
        Val Leu Ser Lys Met Ser Asn Glu Tyr Leu Asp Glu Gly Tyr Ser Arg
                    290                 295                 300
        Asp Thr Val Ile Lys Ala Thr Val Phe Ser Leu Val Leu Asp Ala Ala
        305                 310                 315                 320
        Asp Thr Val Ala Leu His Met Asn Trp Gly Met Ala Leu Leu Ile Asn
                        325                 330                 335
        Asn Gln His Ala Leu Lys Lys Ala Gln Glu Glu Ile Asp Lys Lys Val
                    340                 345                 350
        Gly Lys Glu Arg Trp Val Glu Glu Ser Asp Ile Lys Asp Leu Val Tyr
                    355                 360                 365
        Leu Gln Ala Ile Val Lys Glu Val Leu Arg Leu Tyr Pro Pro Gly Pro
                    370                 375                 380
        Leu Leu Val Pro His Glu Asn Val Glu Asp Cys Val Val Ser Gly Tyr
        385                 390                 395                 400
        His Ile Pro Lys Gly Thr Arg Leu Phe Val Asn Val Met Lys Leu Gln
                        405                 410                 415
        Arg Asp Pro Lys Leu Trp Ser Asn Pro Asp Lys Phe Asp Pro Glu Arg
                    420                 425                 430
        Phe Phe Ala Asp Asp Ile Asp Tyr Arg Gly Gln His Tyr Glu Phe Ile
                    435                 440                 445
        Pro Phe Gly Ser Gly Arg Arg Ser Cys Pro Gly Met Thr Tyr Ala Leu
                    450                 455                 460
        Gln Ala Glu His Leu Thr Ile Ala His Leu Ile Gln Gly Phe Asn Tyr
        465                 470                 475                 480
        Lys Thr Pro Asn Asp Glu Pro Leu Asp Met Lys Glu Gly Ala Gly Leu
                        485                 490                 495
```

```
Thr Ile Arg Lys Val Asn Pro Val Glu Val Thr Ile Thr Ala Arg Leu
                500                 505                 510

Ala Pro Glu Leu Tyr
        515

<210> SEQ ID NO 33
<211> LENGTH: 421
<212> TYPE: PRT
<213> ORGANISM: Nicotiana tabacum
<220> FEATURE:
<221> NAME/KEY: VARIANT
<222> LOCATION: (1)...(421)
<223> OTHER INFORMATION: CYP82E5 W422Stop Variant

<400> SEQUENCE: 33

Met Val Ser Pro Val Glu Ala Ile Val Gly Leu Val Thr Leu Thr Leu
  1               5                  10                  15

Leu Phe Tyr Phe Leu Trp Pro Lys Lys Phe Gln Ile Pro Ser Lys Pro
             20                  25                  30

Leu Pro Pro Lys Ile Pro Gly Gly Trp Pro Val Ile Gly His Leu Phe
         35                  40                  45

Tyr Phe Asp Asp Asp Gly Asp Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320
```

```
Asp Thr Val Ala Leu His Met Asn Trp Gly Met Ala Leu Leu Ile Asn
                    325                 330                 335
Asn Gln His Ala Leu Lys Lys Ala Gln Glu Glu Ile Asp Lys Lys Val
                340                 345                 350
Gly Lys Glu Arg Trp Val Glu Glu Ser Asp Ile Lys Asp Leu Val Tyr
            355                 360                 365
Leu Gln Ala Ile Val Lys Glu Val Leu Arg Leu Tyr Pro Pro Gly Pro
        370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu
                420

<210> SEQ ID NO 34
<211> LENGTH: 517
<212> TYPE: PRT
<213> ORGANISM: Nicotiana tabacum
<220> FEATURE:
<221> NAME/KEY: VARIANT
<222> LOCATION: (1)...(517)
<223> OTHER INFORMATION: CYP82E5 P449L

<400> SEQUENCE: 34

Met Val Ser Pro Val Glu Ala Ile Val Gly Leu Val Thr Leu Thr Leu
  1               5                  10                  15
Leu Phe Tyr Phe Leu Trp Pro Lys Lys Phe Gln Ile Pro Ser Lys Pro
                 20                  25                  30
Leu Pro Pro Lys Ile Pro Gly Gly Trp Pro Val Ile Gly His Leu Phe
             35                  40                  45
Tyr Phe Asp Asp Asp Gly Asp Asp Arg Pro Leu Ala Arg Lys Leu Gly
         50                  55                  60
Asp Leu Ala Asp Lys Tyr Gly Pro Val Phe Thr Phe Arg Leu Gly Leu
 65                  70                  75                  80
Pro Leu Val Leu Val Val Ser Ser Tyr Glu Ala Val Lys Asp Cys Phe
                 85                  90                  95
Ser Thr Asn Asp Ala Ile Phe Ser Asn Arg Pro Ala Phe Leu Tyr Gly
                100                 105                 110
Glu Tyr Leu Gly Tyr Ser Asn Ala Met Leu Phe Leu Thr Lys Tyr Gly
            115                 120                 125
Pro Tyr Trp Arg Lys Asn Arg Lys Leu Val Ile Gln Glu Val Leu Ser
        130                 135                 140
Ala Ser Arg Leu Glu Lys Leu Lys His Val Arg Phe Gly Lys Ile Gln
145                 150                 155                 160
Thr Ser Ile Lys Ser Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Arg Lys Ala Phe Lys Asp Phe Ile Ile Leu Ser Met
    210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
```

```
                    245                 250                 255
Asp Ser Val Phe Gln Asn Trp Leu Glu Glu His Val Lys Lys Arg Glu
                260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Pro Glu Arg
            420                 425                 430

Phe Phe Ala Asp Asp Ile Asp Tyr Arg Gly Gln His Tyr Glu Phe Ile
        435                 440                 445

Leu Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 35
<211> LENGTH: 23
<212> TYPE: DNA
<213> ORGANISM: Artificial Sequence
<220> FEATURE:
<223> OTHER INFORMATION: forward primer for exon 1 of CYP82E10 gene

<400> SEQUENCE: 35
gtgatagttt gattcccaag tgc                                           23

<210> SEQ ID NO 36
<211> LENGTH: 22
<212> TYPE: DNA
<213> ORGANISM: Artificial Sequence
<220> FEATURE:
<223> OTHER INFORMATION: reverse primer for exon 1 of CYP82E10 gene

<400> SEQUENCE: 36
ctcccaaagt tagattagtc cg                                            22

<210> SEQ ID NO 37
```

```
<211> LENGTH: 18
<212> TYPE: DNA
<213> ORGANISM: Artificial Sequence
<220> FEATURE:
<223> OTHER INFORMATION: forward primer for exon 2 of CYP82E10 gene

<400> SEQUENCE: 37
aggtcgcgct gattcttg                                                   18

<210> SEQ ID NO 38
<211> LENGTH: 26
<212> TYPE: DNA
<213> ORGANISM: Artificial Sequence
<220> FEATURE:
<223> OTHER INFORMATION: reverse primer for exon 2 of CYP82E10 gene

<400> SEQUENCE: 38
agatgaatac ccatctatct aggagt                                          26

<210> SEQ ID NO 39
<211> LENGTH: 2752
<212> TYPE: DNA
<213> ORGANISM: Nicotiana tabacum
<220> FEATURE:
<221> NAME/KEY: 5'UTR
<222> LOCATION: (1)...(50)
<223> OTHER INFORMATION: CYP82E4v2 5' UTR
<220> FEATURE:
<221> NAME/KEY: exon
<222> LOCATION: (51)...(989)
<223> OTHER INFORMATION: CYP82E4v2 exon 1 sequence
<220> FEATURE:
<221> NAME/KEY: intron
<222> LOCATION: (990)...(1990)
<223> OTHER INFORMATION: CYP82E4v2 intron sequence
<220> FEATURE:
<221> NAME/KEY: exon
<222> LOCATION: (1991)...(2602)
<223> OTHER INFORMATION: CYP82E4v2 exon 2 sequence
<220> FEATURE:
<221> NAME/KEY: 3'UTR
<222> LOCATION: (2603)...(2685)
<223> OTHER INFORMATION: CYP82E4v2 3' UTR

<400> SEQUENCE: 39
aaggaagttg ccgatagtta tattctcaac ttcttatcta aaaatccata atgctttctc      60
ccatagaagc cattgtagga ctagtaacct tcacatttct cttcttcttc ctatggacaa     120
aaaaatctca aaaaccttca aaacccttac caccgaaaat ccccggagga tggccggtaa     180
tcggccatct tttccacttc aatgacgacg gcgacgaccg tccattagct cgaaaactcg     240
gagacttagc tgacaaatac ggccccgttt tcacttttcg gctaggcctt cccttgtct      300 tagttgtaag cagttacgaa gctgtaaaag actgttctc tacaaatgac gccatttttt     360
ccaatcgtcc agcttttctt tacggcgatt accttggcta caataatgcc atgctatttt     420
tggccaatta cggaccttac tggcgaaaaa atcgaaaatt agttattcag gaagttctct     480
ccgctagtcg tctcgaaaaa ttcaaacacg tgagatttgc aagaattcaa gcagagcatta    540 agaatttata tactcgaatt gatggaaatt cgagtacgat aaatttaact gattggttag     600
aagaattgaa ttttggtctg atcgtgaaga tgatcgctgg aaaaaattat gaatccggta     660
aaggagatga acaagtggag agatttaaga aagcgtttaa ggatttatg atttatcaa       720 tggagtttgt gttatgggat gcatttccaa ttccattatt taaatgggtg gattttcaag     780
ggcatgttaa ggctatgaaa aggactttta aagatataga ttctgttttt cagaattggt     840
tagaggaaca tattaataaa agagaaaaaa tggaggttaa tgcagaaggg aatgaacaag     900
```

-continued

```
atttcattga tgtggtgctt tcaaaaatga gtaatgaata tcttggtgaa ggttactctc    960
gtgatactgt cattaaagca acggtgtttg taagttcatc tgtcattttt catttattca   1020
cttttatttt gaggagcaga catgttaata ataatttgga gcaactgtaa agttatctat   1080
gtgtacaggt tcgagcctca ggtgcaacca ctaatgcttg tattagatta tgttgtctgc   1140
atcatacccc taattggagt gtggctcttc ccgaaccctg caatgctgga tgctggatgc   1200
tttatgtatc agactgacct tttttgttaaa ctatctaaat actaaggatg atgatttaat   1260
aaaaatatag aatggtaaac agaaaaagat gagattattt ttggggctat atggattcgc   1320
ccgggctttg ggaggtaaaa cggtatctac cagttgagac tttactccag aactttatct   1380
cgagagctct gaataaaaat gaatagtat ttaccactcc aaaatctttg atggtaaaaa    1440
gatgagatat aacctcttat aattgattga accacgttga tagaataaaa cttctttact   1500
cccattcagc ataagaaaaa tgaaaccaaa cggaattctt ctctttttta gggggaaatt   1560
ccttaattgc ttgttgaata tagattcatg tcgttattct attttaata atgatgaaaa    1620
tcaatatagt caaagttaat acttatgtca tttggtttgc ggacaagtta tattggaact   1680
atataatacg tctattatag aatagtgatt atttagagga tatacatttt ttttggataa   1740
atatttgatt tattggatta aaaatagaat atacaggtaa ggtctaaaac gtgtgtttgc   1800
ttttacacta aataaacttg acctcgtaca attctaagaa atatttgaa ataaatgaat    1860
tattttattg ttaatcaatt aaaaaaatca tagtatagat gagatgtgtg catacttgac   1920
aataactata ctaactaaaa caaggtatgt gaataattga tattcctttt ttaattattc   1980
ttttttccag agtttggtct tggatgcagc agacacagtt gctcttcaca taaattgggg   2040
aatggcatta ttgataaaca atcaaaaggc cttgacgaaa gcacaagaag agatagacac   2100
aaaagttggt aaggacagat gggtagaaga gagtgatatt aaggatttgg tatacctcca   2160
agctattgtt aaagaagtgt tacgattata tccaccagga cctttgttag taccacacga   2220
aaatgtagaa gattgtgttg ttagtggata tcacattcct aaagggacaa gattattcgc   2280
aaacgtcatg aaactgcaac gtgatcctaa actctggtct gatcctgata ctttcgatcc   2340
agagagattc attgctactg atattgactt tcgtggtcag tactataagt atatcccgtt   2400
tggttctgga agacgatctt gtccagggat gacttatgca ttgcaagtgg aacacttaac   2460
aatggcacat ttgatccaag gtttcaatta cagaactcca aatgacgagc ccttggatat   2520
gaaggaaggt gcaggcataa ctatacgtaa ggtaaatcct gtggaactga taatagcgcc   2580
tcgcctggca cctgagcttt attaaaacct aagatctttc atcttggttg atcattgtat   2640
aatactccta aatggatatt catttacctt ttatcaatta attgtcagta cgagtttttc   2700
taatttggta catttgtaat aataagtaaa gaataattgt gctaatatat aa           2752
```

```
<210> SEQ ID NO 40
<211> LENGTH: 2685
<212> TYPE: DNA
<213> ORGANISM: Nicotiana tabacum
<220> FEATURE:
<221> NAME/KEY: 5'UTR
<222> LOCATION: (1)...(30)
<223> OTHER INFORMATION: CYP82E5v2 5' UTR
<220> FEATURE:
<221> NAME/KEY: exon
<222> LOCATION: (31)...(969)
<223> OTHER INFORMATION: CYP82E5v2 exon 1 sequence
<220> FEATURE:
<221> NAME/KEY: intron
<222> LOCATION: (970)...(2023)
```

<223> OTHER INFORMATION: CYP82E5v2 intron sequence
<220> FEATURE:
<221> NAME/KEY: exon
<222> LOCATION: (2024)...(2635)
<223> OTHER INFORMATION: CYP82E5v2 exon 2 sequence
<220> FEATURE:
<221> NAME/KEY: 3'UTR
<222> LOCATION: (2636)...(2685)
<223> OTHER INFORMATION: CYP82E5v2 3' UTR

<400> SEQUENCE: 40

```
gattcccaag ttcttttcta aaactccata atggtttctc ccgtagaagc cattgtagga      60
ctagtaaccc ttacacttct cttctacttc ctatggccca aaaaatttca ataccttca     120
aaaccattac caccgaaaat tcccggaggg tggccggtaa tcggccatct tttctacttc    180
gatgatgacg gcgacgaccg tccattagct cgaaaactcg gagacttagc tgacaaatac    240
ggcccggttt tcactttccg gctaggcctt ccgcttgtgt tagttgtaag cagttacgaa    300
gctgtaaaag actgcttctc tacaaatgac gccattttct ccaatcgtcc agcttttctt    360
tacggtgaat accttggcta cagtaatgcc atgctatttt tgacaaaata cggaccttat    420
tggcgaaaaa atagaaaatt agtcattcag gaagttctct ctgctagtcg tctcgaaaaa    480
ttgaagcacg tgagatttgg taaaattcaa acgagcatta agagtttata cactcgaatt    540
gatgaaaatt cgagtacgat aaatctaact gattggttag aagaattgaa ttttggtctg    600
atcgtgaaaa tgatcgctgg gaaaaattat gaatccggta aaggagatga acaagtggag    660
agatttagga aagcgtttaa ggatttttata attttatcaa tggagtttgt gttatgggat    720
gcttttccaa ttccattgtt caaatgggtg gatttttcaag gccatgttaa ggccatgaaa    780
aggacattta aggatataga ttctgttttt cagaattggt tagaggaaca tgtcaagaaa    840
agagaaaaaa tggaggttaa tgcacaaggg aatgaacaag atttcattga tgtggtgctt    900
tcaaaaatga gtaatgaata tcttgatgaa ggttactctc gtgatactgt cataaaagca    960
acagtgtttg taagttcatt ttcatttttc attattcagt ctgatttttga ggaatagaca   1020
ggttaataat aatttaagta attagattat ctaaatacta aggatgatta tatatagtaa   1080
aaatgtagaa tgataaatgg aaaaaagatg agaattttt gtgcctcgac taatctatat   1140
atctttggga gttaaaagtg cttcaccaaa ggggacttttt cctcatagct caagttagaa   1200
gtttgattat agatgaaaga gtattttatca cttcacgaac tctgatgata aaagtaaatg   1260
agatataacc agttataatt gatagaataa aacttcatta ctcccattga gcataaaaaa   1320
aaaagtaaaa gggacttctt ctcttttttt tagggagaaa ttctttaatt gtttgttaaa   1380
tatagattca tgttttttt ttcttctatt tctaataata atggttcttg aatcaggtcg   1440
ttgactttgt agcagcaata tagtcaaagc taatatccat gttatttggt tttcgaacaa   1500
gttatactga aattatatat acgggtatta ataataaca ttattattta taggatatac   1560
tttttttatt gggtaaatat tacaacaaca acaactgact cagtaaaatt ttactagtgg   1620
ggtatgggga gggtagtgtg tatgcagacc ttaccctac cccgaaggag tagagggatt   1680
gtttccgaaa gaccctcggc tcaagaaaac aaaagagac aatatcagta ccaccacaga   1740
tcatattatt aggtaaatgt tatttttattg aattaaagat gaaatataca ggtaaggtat   1800
aaaacgtgta tttgatttta cactagataa atttgacctc gtacatctct aagagaaagc   1860
tgaaataaat gaattttaaa tttaaaaaaa aaattcatta gtataatgag atgtgcatac   1920
ttgacaatta ctatactaaa tagaacaagg ttcggcagat agtgacacta acctactttt   1980
gtattgaatt atccttttta attttattct aatttgtcta cagagtttgg tcttggatgc   2040
```

```
tgcggacaca gttgctcttc acatgaattg gggaatggca ttactgataa acaatcaaca    2100
tgccttgaag aaagcacaag aagagatcga taaaaaagtt ggtaaggaaa gatgggtaga    2160
agagagtgat attaaggatt tggtctacct ccaagctatt gttaaagaag tgttacgatt    2220
atatccacca ggacctttat tagtacctca tgaaaatgta gaggattgtg ttgttagtgg    2280
atatcacatt cctaaaggga ctagactatt cgcgaacgtt atgaaattgc agcgcgatcc    2340
taaactctgg tcaaatcctg ataagtttga tccagagaga ttcttcgctg atgatattga    2400
ctaccgtggt cagcactatg agtttatccc atttggttct ggaagacgat cttgtccggg    2460
gatgacttat gcattacaag tggaacacct aacaatagca catttgatcc agggtttcaa    2520
ttacaaaact ccaaatgacg agcccttgga tatgaaggaa ggtgcaggat taactatacg    2580
taaagtaaat cctgtagaag tgacaattac ggctcgcctg gcacctgagc tttattaaaa    2640
ccttagatgt tttatcttga ttgtactaat atatatagca gaaaa                   2685
```